US012426880B2

(12) United States Patent
Fanelli et al.

(10) Patent No.: US 12,426,880 B2
(45) Date of Patent: Sep. 30, 2025

(54) SURGICAL STAPLER CARTRIDGE HAVING INTERMEDIATE RAISED TISSUE ENGAGEMENT PROTRUSIONS

(71) Applicant: Cilag GmbH international, Zug (CH)

(72) Inventors: Nicholas Fanelli, Morrow, OH (US); Gregory G. Scott, Cincinnati, OH (US); Anthony Nguyen, West Chester, OH (US); Kevin M. Fiebig, Cincinnati, OH (US); Scott A. Jenkins, Mason, OH (US); Frederick E. Shelton, IV, Hillsboro, OH (US); Nicholas A. Wilson, Montgomery, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/588,147

(22) Filed: Feb. 27, 2024

(65) Prior Publication Data

US 2024/0382197 A1    Nov. 21, 2024

Related U.S. Application Data

(60) Provisional application No. 63/467,622, filed on May 19, 2023.

(51) Int. Cl.
*A61B 17/072* (2006.01)

(52) U.S. Cl.
CPC .. *A61B 17/072* (2013.01); *A61B 2017/07271* (2013.01)

(58) Field of Classification Search
CPC .............................................. A61B 17/07207
See application file for complete search history.

(56) References Cited

U.S. PATENT DOCUMENTS

| 7,735,703 B2 | 6/2010 | Morgan et al. |
| 8,393,514 B2 | 3/2013 | Shelton, IV et al. |

(Continued)

FOREIGN PATENT DOCUMENTS

| CN | 105919642 A | 9/2016 |
| CN | 105997172 A | 10/2016 |

(Continued)

OTHER PUBLICATIONS

U.S. Appl. No. 18/588,094.

(Continued)

*Primary Examiner* — Nathaniel C Chukwurah
(74) *Attorney, Agent, or Firm* — Frost Brown Todd LLP

(57) ABSTRACT

An apparatus includes a cartridge body, a deck, an elongate slot, a plurality of pockets, and a plurality of engagement protrusions. The plurality of pockets include first and second pockets. The plurality of engagement protrusions extend from the deck and are configured to grip tissue or an adjunct material. The plurality of engagement protrusions include first and second engagement protrusions. The first engagement protrusion is associated with the first pocket. The first engagement protrusion includes a lateral portion extending longitudinally along a lateral side of the first pocket. The first engagement protrusion does not extend along a second lateral side of the first pocket such that the second lateral side opens directly to the deck. The second engagement protrusion is associated with the second pocket. The second engagement protrusion includes a lateral portion extending longitudinally along the second lateral side of the second pocket.

20 Claims, 48 Drawing Sheets

(56) References Cited

U.S. PATENT DOCUMENTS

| | | |
|---|---|---|
| 8,453,914 B2 | 6/2013 | Laurent et al. |
| 8,733,613 B2 * | 5/2014 | Huitema ............ A61B 17/0682 227/176.1 |
| 9,186,142 B2 | 11/2015 | Fanelli et al. |
| 9,717,497 B2 | 8/2017 | Zerkle et al. |
| 9,808,248 B2 | 11/2017 | Hoffman |
| 9,839,421 B2 | 12/2017 | Zerkle et al. |
| 9,844,369 B2 | 12/2017 | Huitema et al. |
| 9,924,944 B2 | 3/2018 | Shelton, IV et al. |
| 10,092,292 B2 | 10/2018 | Boudreaux et al. |
| 10,130,359 B2 | 11/2018 | Hess et al. |
| 10,166,023 B2 | 1/2019 | Vendely et al. |
| 10,349,939 B2 | 7/2019 | Shelton, IV et al. |
| 10,357,252 B2 | 7/2019 | Harris et al. |
| 10,542,981 B2 | 1/2020 | Miller et al. |
| 11,045,191 B2 | 6/2021 | Shelton, IV et al. |
| 11,058,426 B2 | 7/2021 | Nalagatla et al. |
| 11,166,724 B2 | 11/2021 | McGiveron et al. |
| 11,202,628 B2 | 12/2021 | Posey et al. |
| 11,229,433 B2 | 1/2022 | Schings et al. |
| D967,421 S | 10/2022 | Shelton, IV et al. |
| 11,517,315 B2 | 12/2022 | Huitema et al. |
| D974,560 S | 1/2023 | Shelton, IV et al. |
| D976,401 S | 1/2023 | Shelton, IV et al. |
| 11,896,218 B2 | 2/2024 | Bakos et al. |
| 2007/0034667 A1 | 2/2007 | Holsten et al. |
| 2015/0297229 A1 | 10/2015 | Schellin et al. |
| 2021/0186493 A1 | 6/2021 | Shelton, IV et al. |
| 2021/0219977 A1 | 7/2021 | Fernandes et al. |
| 2022/0387027 A1 | 12/2022 | Shelton, IV et al. |

FOREIGN PATENT DOCUMENTS

| | | |
|---|---|---|
| CN | 105997173 A | 10/2016 |
| CN | 106037848 A | 10/2016 |
| CN | 108542454 A | 9/2018 |
| CN | 111195142 A | 5/2020 |

OTHER PUBLICATIONS

U.S. Appl. No. 18/588,175.
U.S. Appl. No. 18/588,206.
U.S. Appl. No. 18/588,240.
U.S. Appl. No. 18/588,269.
U.S. Appl. No. 18/588,684.
U.S. Appl. No. 18/588,094, entitled "Incompatible Staple Cartridge Use Prevention Features for Surgical Stapler," filed Feb. 27, 2024.
U.S. Appl. No. 18/588,175, entitled "Surgical Stapler Cartridge Having Tissue Engagement Protrusions with Enlarged Engagement Surface," filed Feb. 27, 2024.
U.S. Appl. No. 18/588,206, entitled "Surgical Stapler Cartridge Having Raised Surface to Promote Buttress Adhesion," filed Feb. 27, 2024.
U.S. Appl. No. 18/588,240, entitled "Surgical Stapler Cartridge Having Cartridge Retention Features," filed Feb. 27, 2024.
U.S. Appl. No. 18/588,269, entitled "Surgical Stapler Anvil Having Staple Forming Pockets with Laterally Varying Orientations," filed Feb. 27, 2024.
U.S. Appl. No. 18/588,684, entitled "Method of Surgical Stapling," filed Feb. 27, 2024.
International Search Report and Written Opinion dated Aug. 16, 2024, for International Application No. PCT/IB2024/054893, 16 pages.

* cited by examiner

SURGICAL STAPLER CARTRIDGE HAVING INTERMEDIATE RAISED TISSUE ENGAGEMENT PROTRUSIONS

PRIORITY

This application claims the benefit of U.S. Pat. App. No. 63/467,622, entitled "Surgical Stapler Cartridge Having Intermediate Raised Tissue Engagement Protrusions," filed May 19, 2023, the disclosure of which is incorporated by reference herein in its entirety.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion or other type of body portion, which is manipulated by the clinician or robotic operator. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The stapling assembly (e.g., a staple cartridge) of a surgical stapler may include raised features that extend upwardly from a deck thereof for enhancing the gripping of tissue by the stapling assembly when the end effector is closed, and/or for guiding the legs of the staples as the legs exit the respective staple openings during deployment of the staples. For example, such raised features may extend upwardly from the deck at or near proximal and distal ends of each cartridge pocket. In some instances, it may also be desirable to adhere an adjunct material, such as a buttress, to the stapling assembly for deployment with the staples to reinforce the mechanical fastening of tissue provided by the deployed staples. Typically, such adjunct material is adhered directly to the deck via an adhesive material.

While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
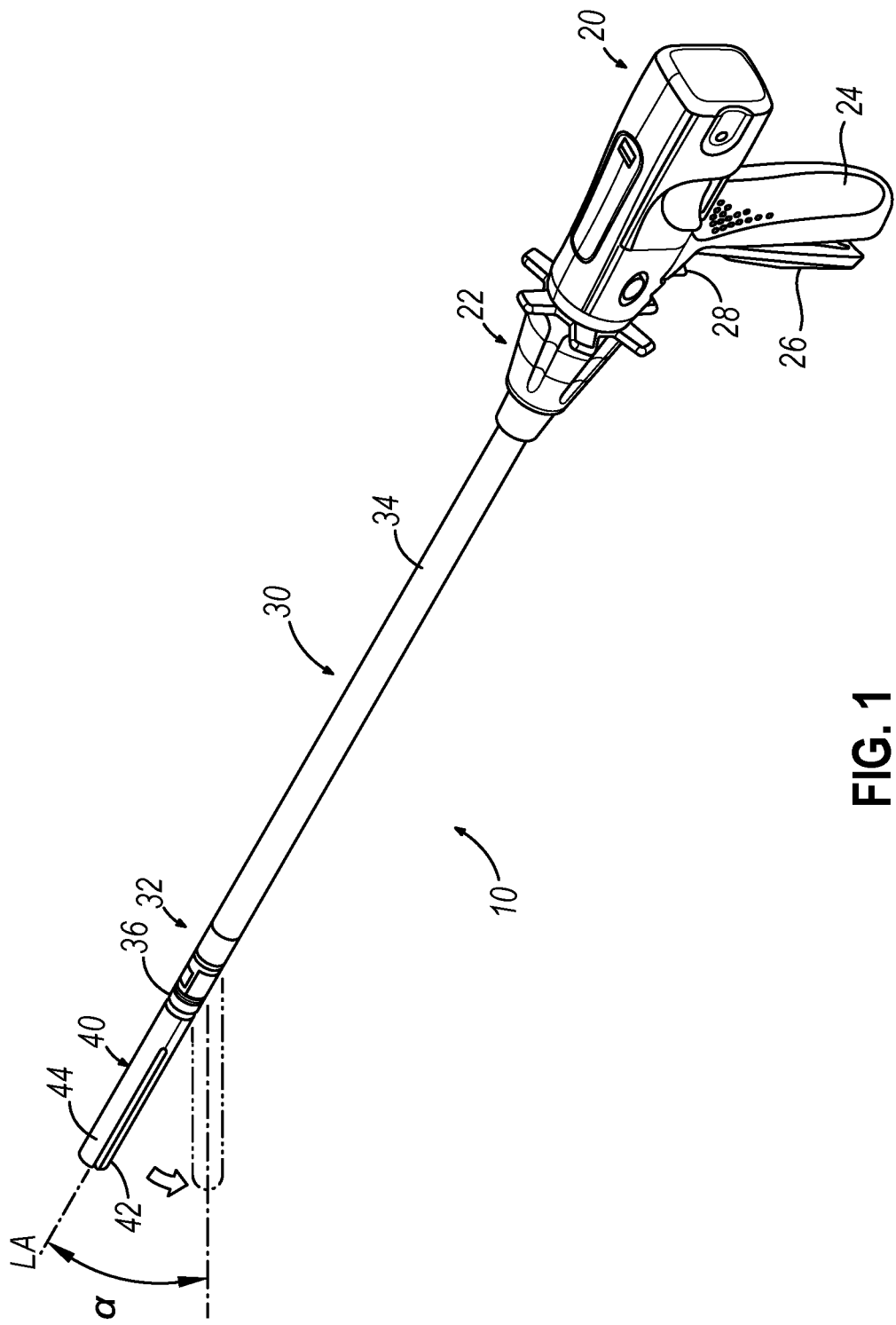
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "top," are relative terms to provide additional clarity to the figure descriptions provided below. The terms "upper," "lower," "lateral," "transverse," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, "substantially parallel" encompasses nominally parallel structures.

As used herein in connection with any examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (BLA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (BLA) at a desired angle (a). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
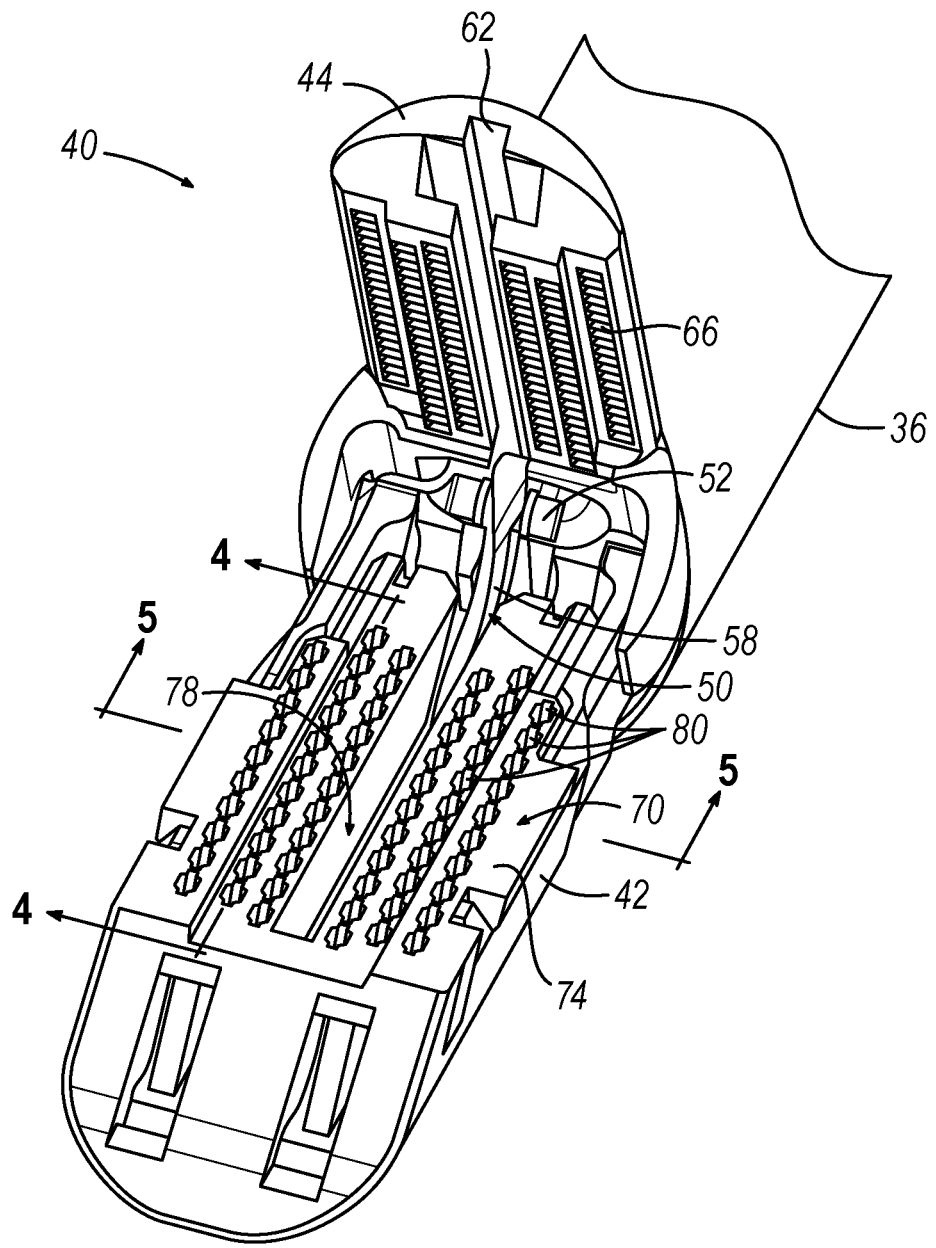
FIG. 2 depicts a perspective view of an end effector of the surgical stapler of FIG. 1, shown in an open state.
Figure 3:
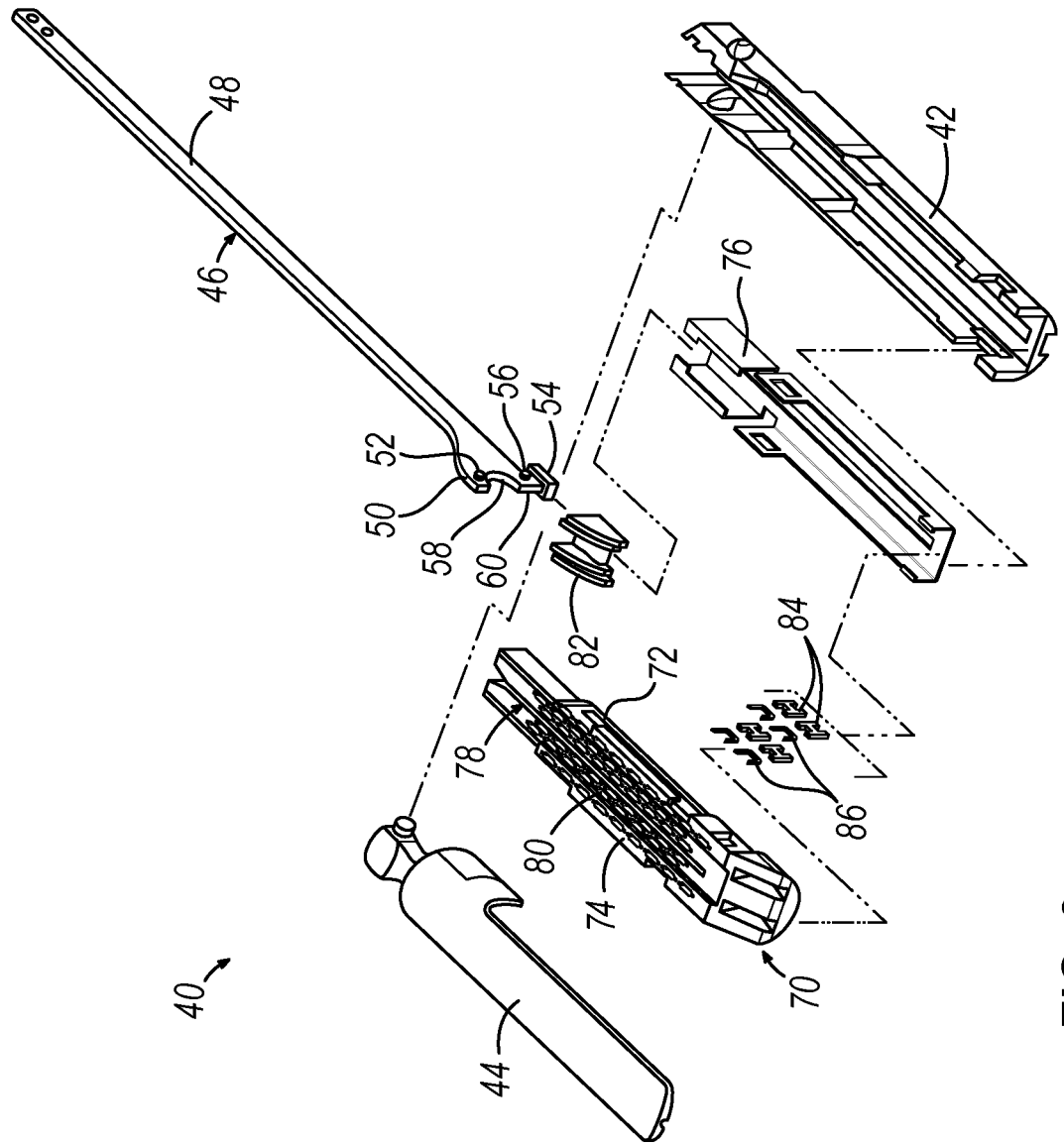
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably installed into a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
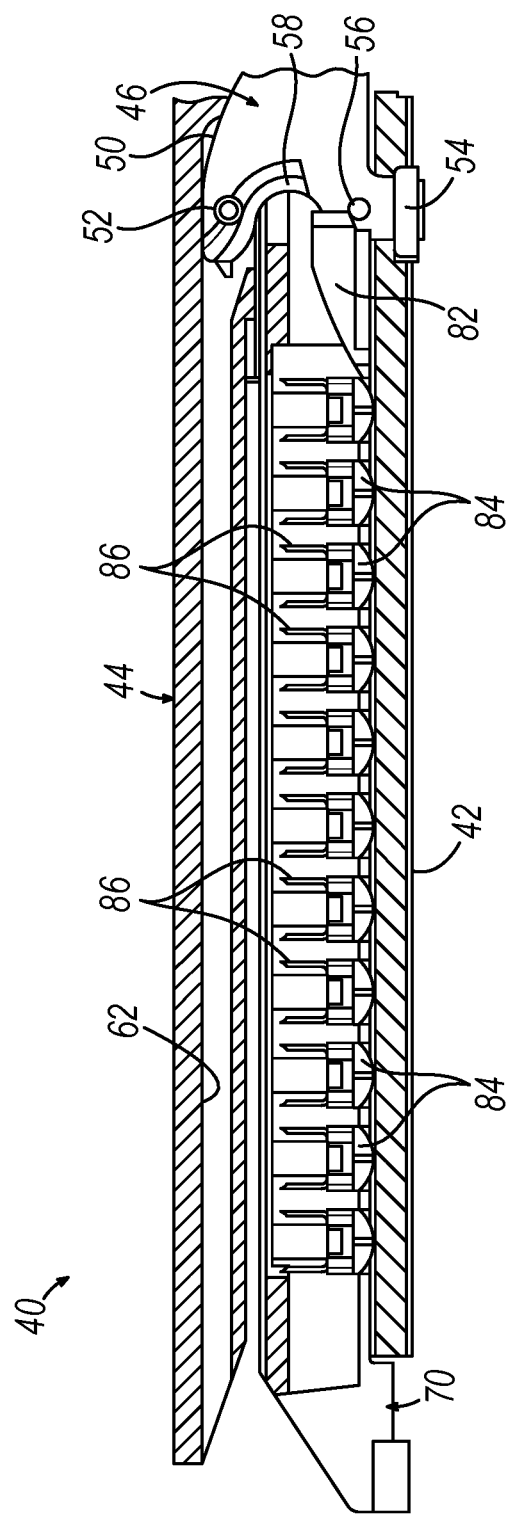
FIG. 4A depicts a side cross-sectional view of the end effector of FIG. 2, taken along line 4-4 of FIG. 2, showing a firing beam and sled in a proximal unfired position.
Figure 4B:
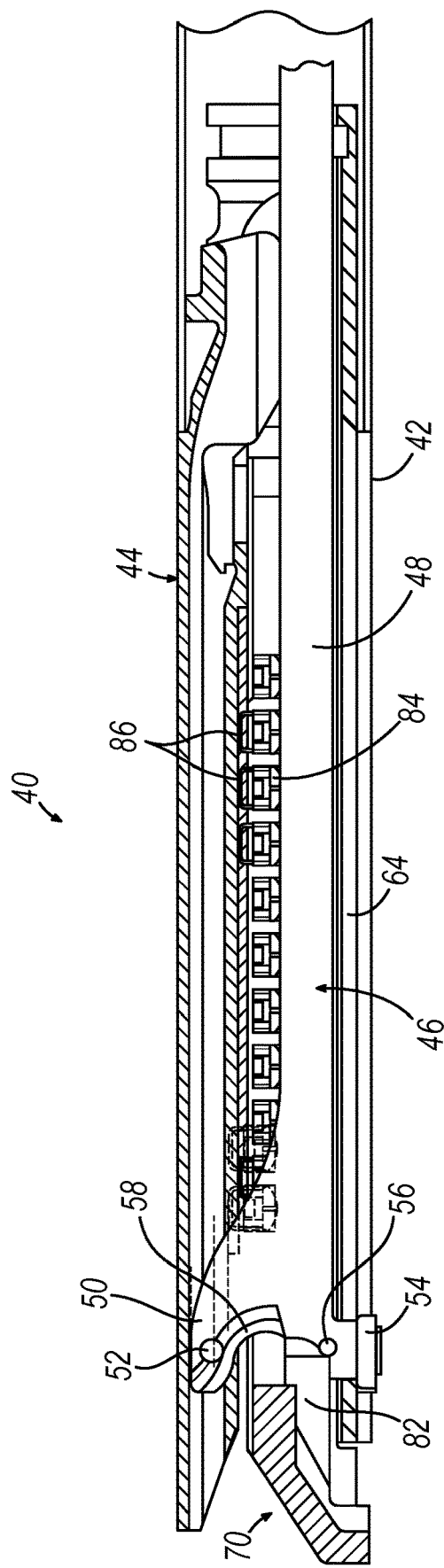
FIG. 4B depicts a side cross-sectional view of the end effector of FIG. 2, taken along line 4-4 of FIG. 2, showing the firing beam and sled in a distal fired position.
Figure 5:
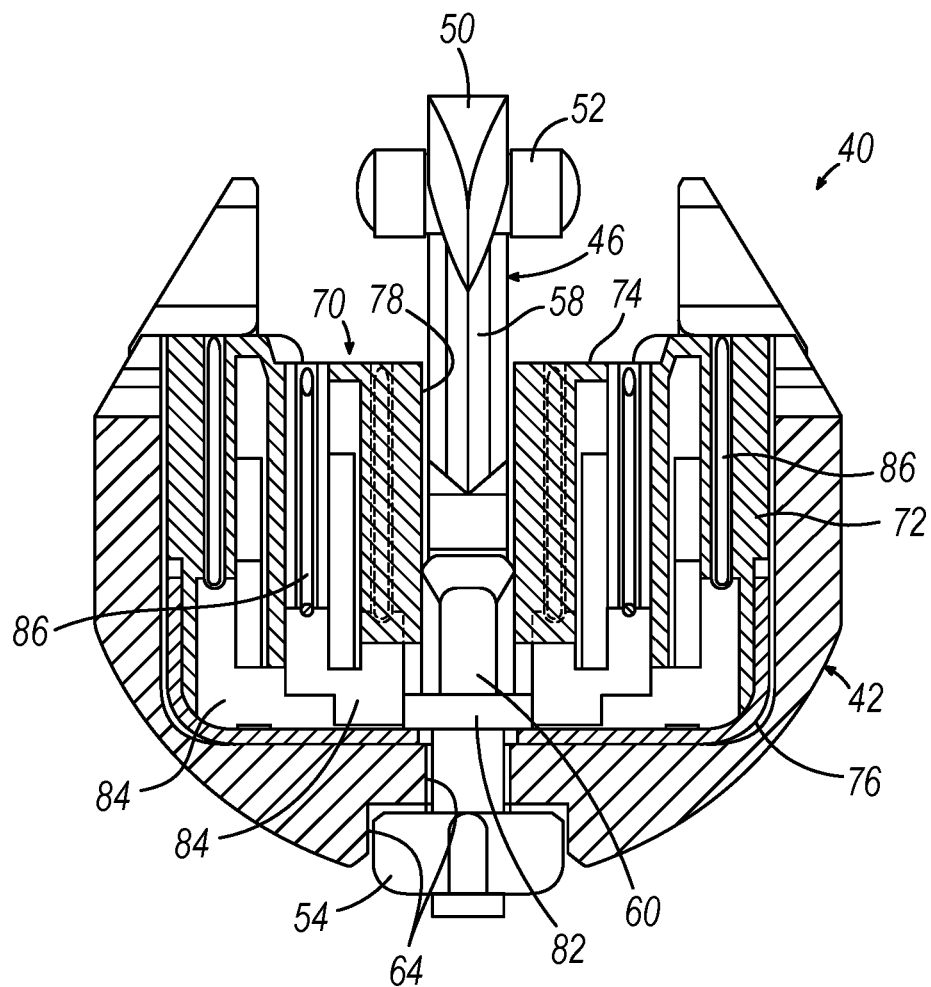
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (84) is aligned with and movable vertically within a respective cartridge pocket (80). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
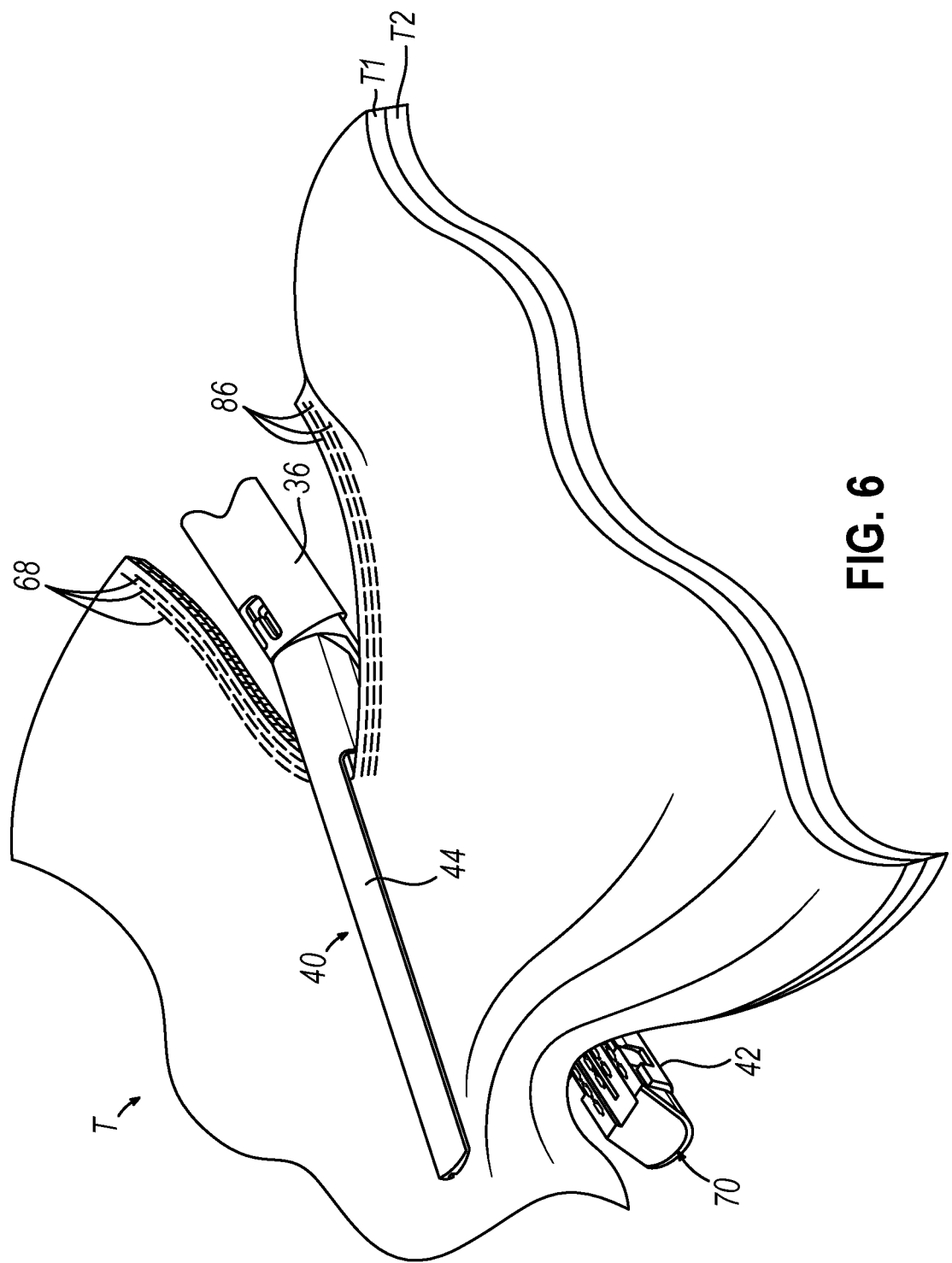
FIG. 6 depicts a perspective view of the end effector of FIG. 2, shown after having been fired once on a first section of tissue and being positioned to clamp and fire on a second section on tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

II. Examples of Stapling Assemblies Including Engagement Protrusions

In some instances, it may be desirable in predetermined areas to incorporate raised features that extend upwardly from the deck thereof for enhancing the gripping of tissue by the stapling assembly (e.g., a staple cartridge) when the end effector is closed, and/or for guiding the legs of the staples as the legs exit the respective staple openings during deployment of the staples. Utilizing raised features in predetermined areas may provide increased localized compression applied to tissue (T) in those predetermined areas while simultaneously minimizing the overall increase in total compression applied to tissue (T). Additionally, linking together raised features may provide increased stiffness.

Tighter tissue compression at the proximal end near the elongate slot may encourage the knife (e.g., distal knife portion of a firing beam (not shown), such as distal knife portion (50) of firing beam (46)), to pierce and cleanly cut the tissue (T) and/or buttress at the proximal end of the elongate slot. It may be desirable to influence the fluid-phase of the tissue outwards laterally and/or longitudinally during the clamping wait time (e.g., which may be about 15 seconds). Due to a natural tendance of fluid to flow in the path of least resistance, more fluid evacuates the tissue sooner during clamping phase to provide less fluid flow during firing. This selectively applies greater tissue pressures in localized regions and encourages fluid-flow-out of tissue (T).

It will be understood that while the features shown and described above are presented in the context of a stapling assembly (e.g., a staple cartridge (B110)) and cartridge bodies (B114, B114a-c, B214, B314, B414, B514, B514a, B614, B614a, B80100, B81100, B82100, B84100, B83100) for surgical stapler (10), such features may also be applied to staple cartridges configured for use with various other types of surgical staplers, such as linear surgical staplers. Each of the examples of staple cartridge (B110) and cartridge bodies (B114, B114a-c, B214, B314, B414, B514, B514a, B614, B614a, B80100, B81100, B82100, B84100, B83100) described below provides such functionality. FIGS. 7-41 are shown to scale.

A. First Example of Staple Cartridge and First Example of a Cartridge Body

Figure 7:
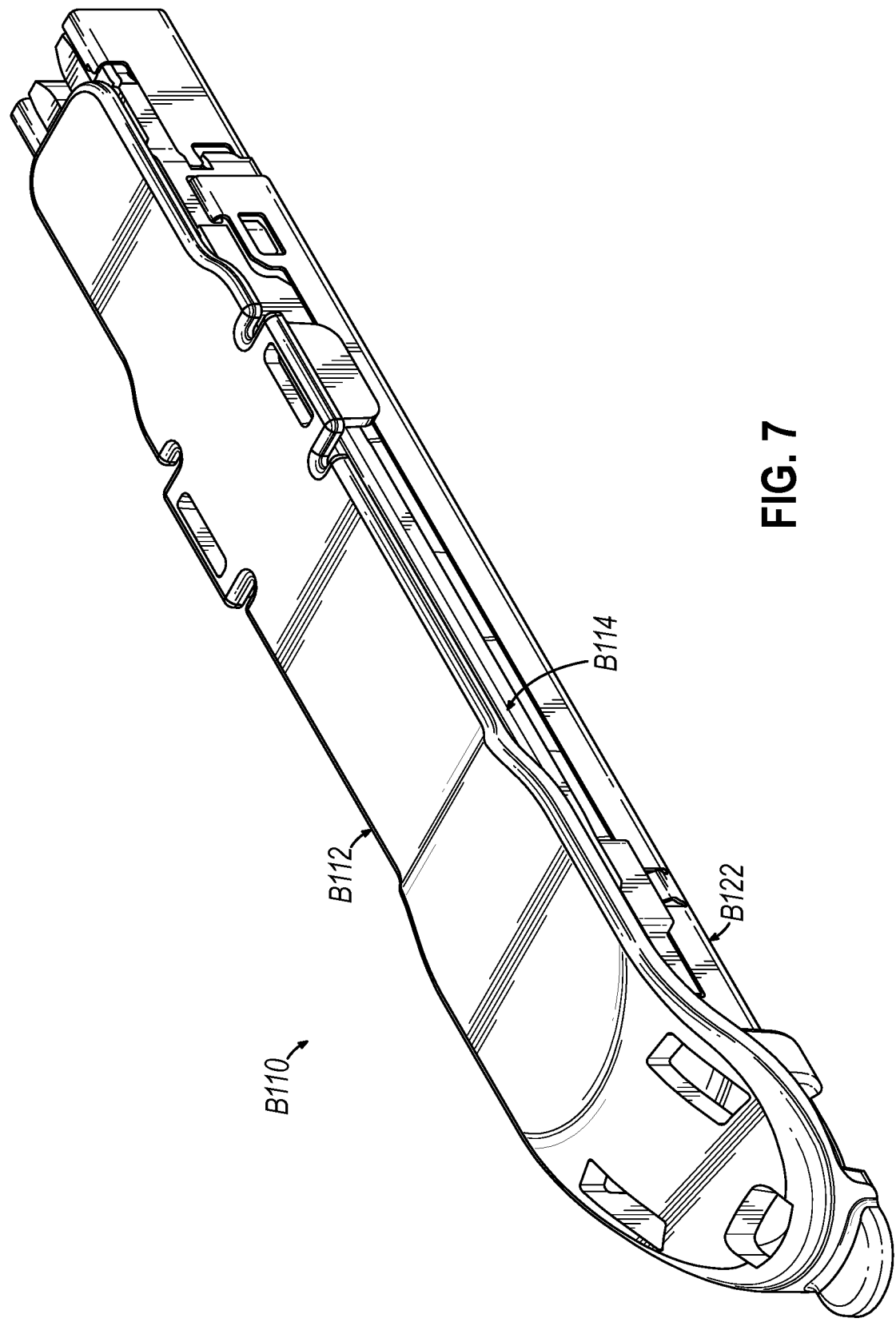
FIG. 7 depicts a perspective view of another example of a staple cartridge for use with the end effector of FIG. 2.
Figure 8:
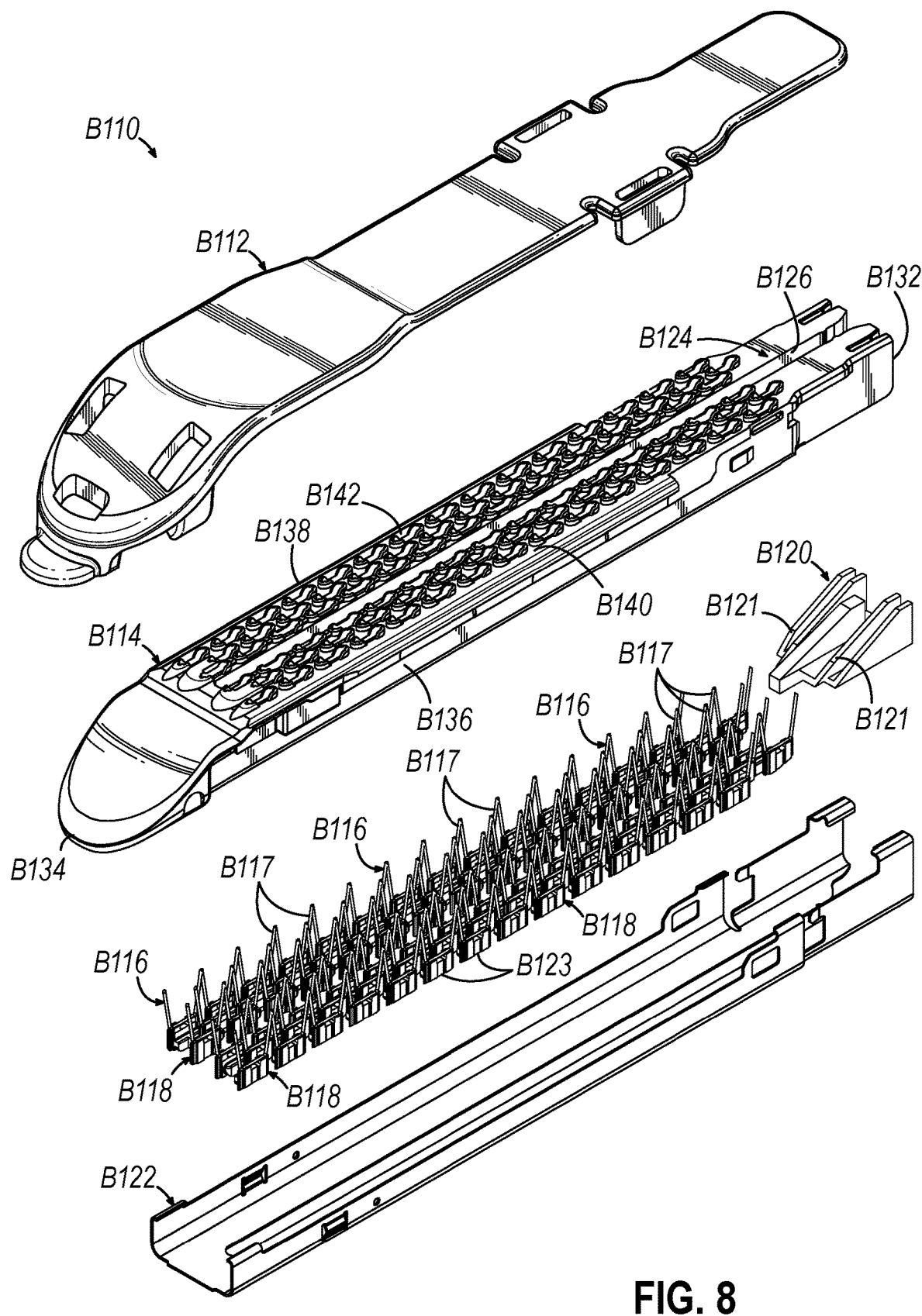
FIG. 8 depicts an exploded perspective view of the staple cartridge of FIG. 7, where the staple cartridge includes a retainer, a cartridge body, staples, staple drivers, a sled, and a tray.

FIGS. 7-18 show an example of a staple cartridge (B110) configured for use with end effector (40) of FIG. 2. As shown in FIGS. 7-8, staple cartridge (B110) includes a retainer (B112), a cartridge body (B114), a plurality of staples (B116), a plurality of staple drivers (B118), a wedge sled (B120), and a tray (B122). Staple cartridge (B110) is similar to staple cartridge (70) described above except as otherwise described below. Staple cartridge (B110) is configured to deploy staples (B116) toward corresponding staple forming pockets of an anvil (not shown), but similar to staple forming pockets (66) of anvil (44). Staples (B116) are similar to staples (86), and staple drivers are similar to staple drivers (B118). Tray (B122) is similar to lower tray (76). Tray (B122) encloses an underside of cartridge body (B114) to retain staples (B116) and staple drivers (B118) within staple cartridge (B110). Wedge sled (B120) is similar to wedge sled (82) and is slidably disposed within cartridge body (B114). Wedge sled (B120) includes upwardly presented cam surfaces (B121) configured to engage the undersides (B123) of staple drivers (B118).

As will be described in greater detail below, cartridge body (B114) includes a deck (B124), an elongate slot (B126) formed in deck (B124), a plurality of cartridge pockets (B128) formed in deck (B124), and a plurality of engagement protrusions (B130a-f) extending outwardly from deck (B124). Cartridge body (B114) includes a proximal end (B132), a distal end (B134), a first lateral side (B136), and a second lateral side (B138). Second lateral side (B138) of cartridge body (B114) is disposed opposite first lateral side (B136). Deck (B124) is similar to upper deck (74) and is configured to compress tissue (T) against an anvil (not shown), but similar to anvil (44). Deck (B124) is defined by cartridge body (B114) and is shown as being substantially planar. Elongate slot (B126) is similar to knife slot (78). Elongate slot (B126) extends along a longitudinal axis (BLA) of cartridge body (B114). Elongate slot (B126) opens upwardly through deck (B124) and terminates at a connecting portion (B131). Elongate slot (B126) is configured to slidably receive a knife therein. The knife may be a distal knife portion of a firing beam (not shown), such as distal knife portion (50) of firing beam (46). Cartridge pockets (B128) are configured to house a plurality of staples (B116). As shown, each cartridge pocket (B128) slidably houses an unformed staple (B116) and a respective staple driver (B118) similar to staple drivers (84) positioned beneath staples (86). While FIG. 8 shows a 1:1 relationship of cartridge pockets (B128) to staples (B116), this may vary.

Figure 9:
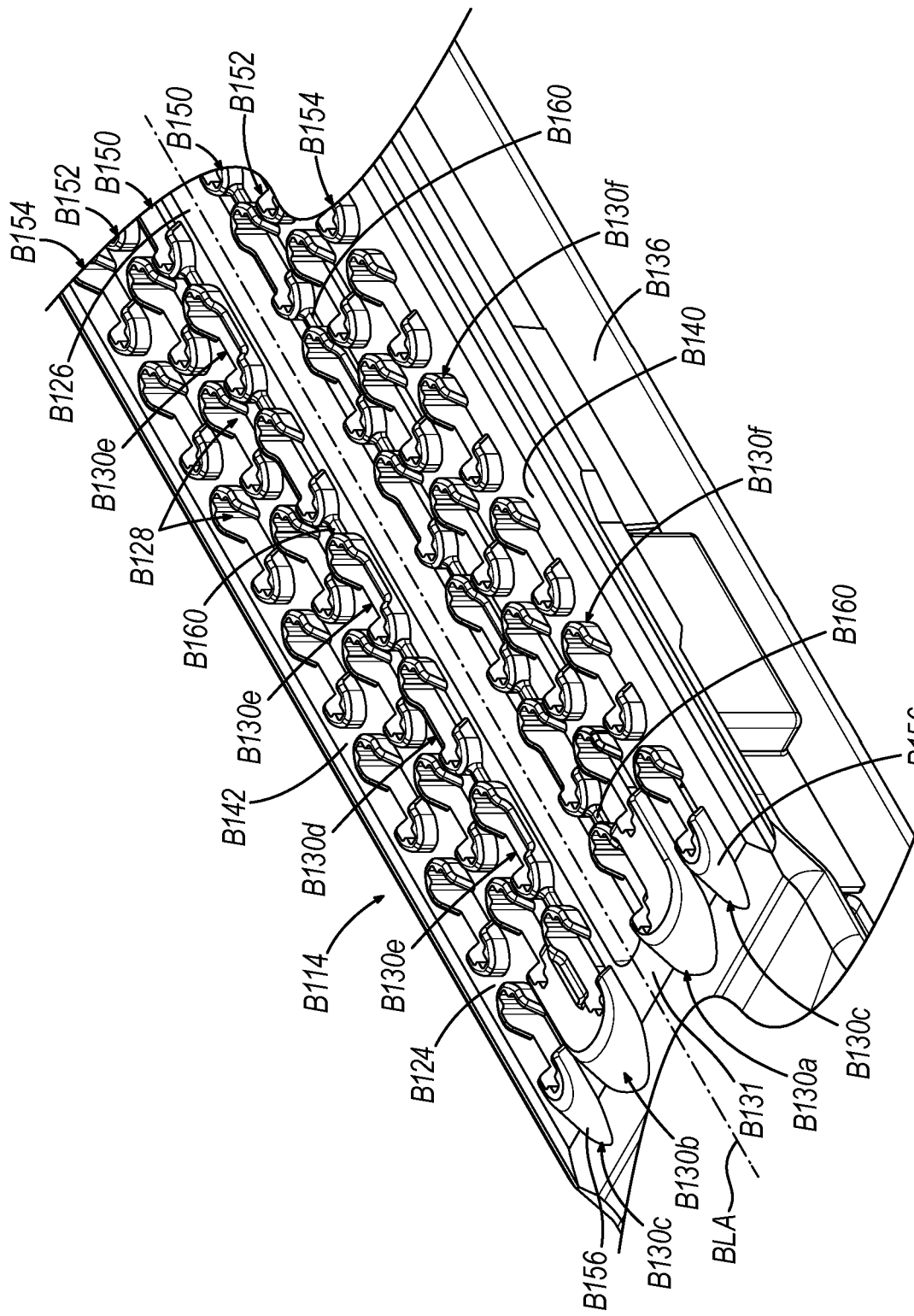
FIG. 9 depicts a perspective view of an enlarged portion of the cartridge body of FIG. 8.
Figure 10:
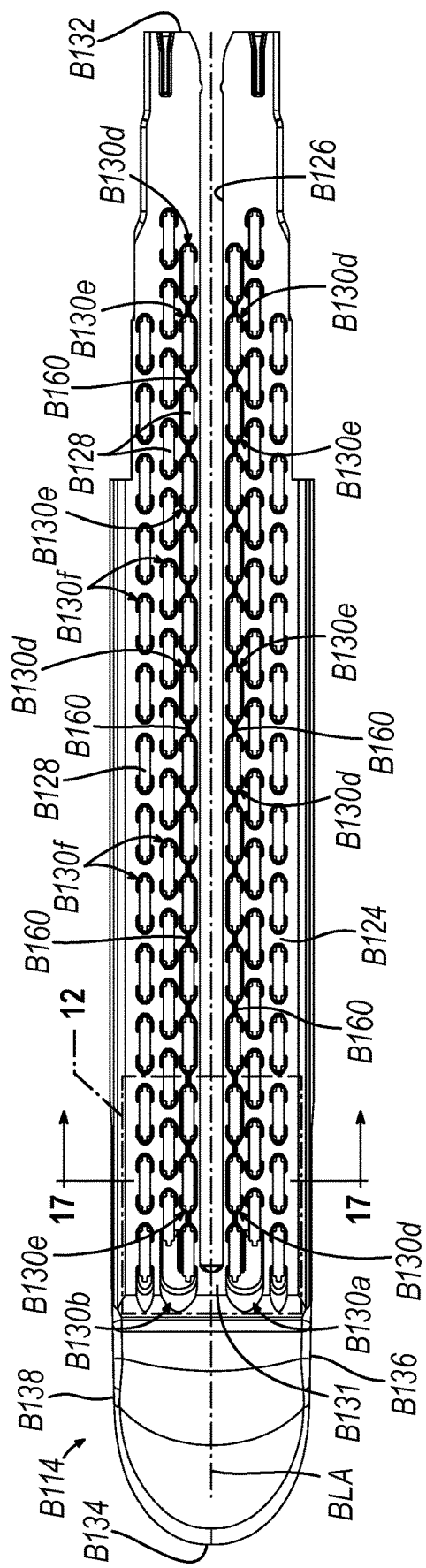
FIG. 10 depicts a top plan view of the cartridge body of FIG. 8.
Figure 12:
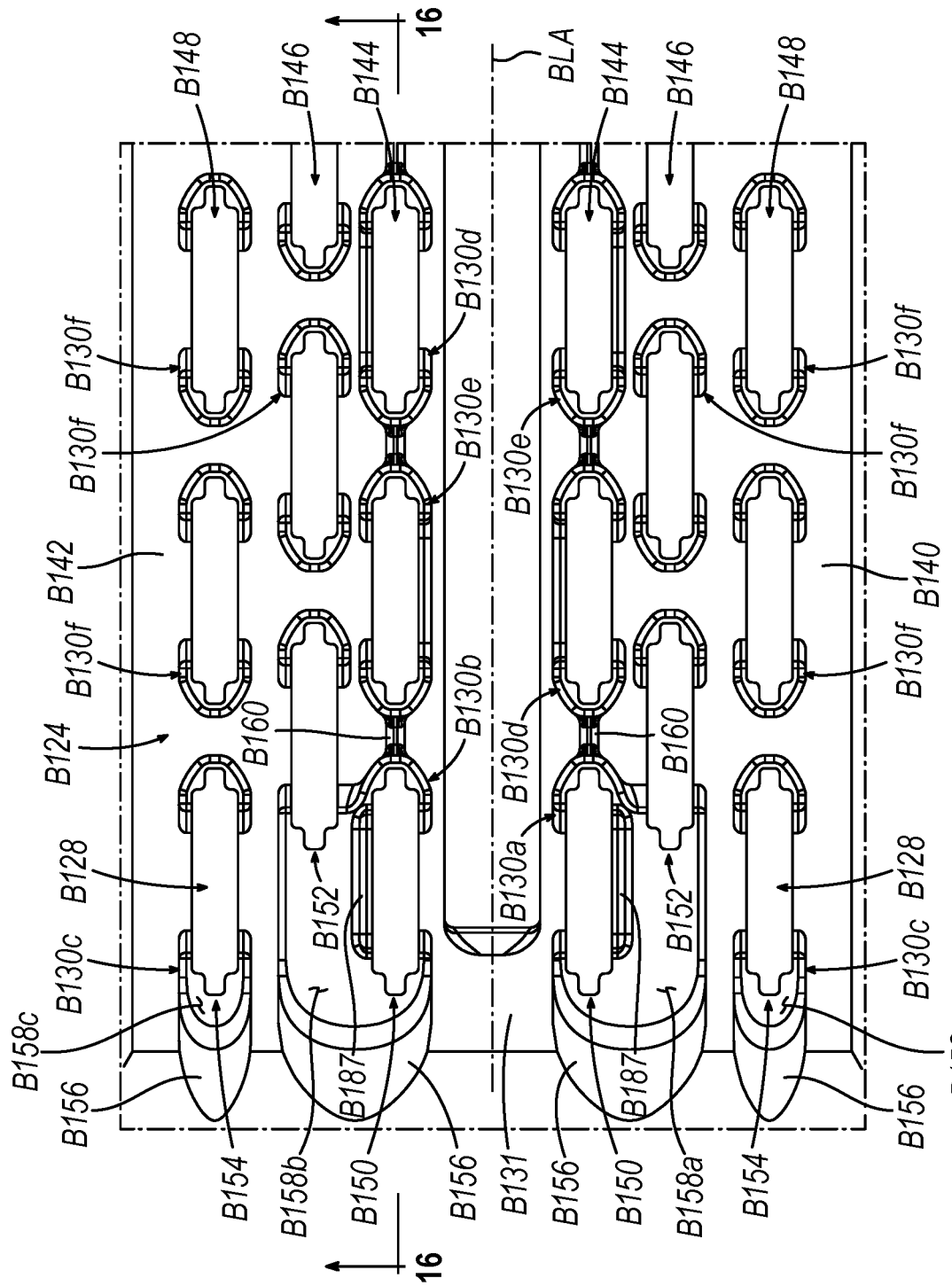
FIG. 12 depicts an enlarged partial top plan view of the cartridge body of FIG. 10.

FIG. 10 shows cartridge pockets (B128) arranged into six longitudinally extending rows. Elongate slot (B126) separates three rows positioned on a first deck side (B140) from three additional rows are positioned a second deck side (B142). Second deck side (B142) of deck (B124) is a mirror image of first deck side (B140). As shown in FIGS. 9 and 12, these longitudinal rows include inner rows (B144), middle rows (B146), and outer rows (B148). While two inner rows (B144), two middle rows (B146), and two outer rows (B148) are shown, more or fewer cartridge rows are envisioned. Inner rows (B144) are the closest cartridge pockets (B128) relative to elongate slot (B126). In other words, inner rows (B144) are positioned closer to elongate slot (B126) than middle rows (B146). Similarly, middle rows (B146) are positioned closer to elongate slot (B126) than outer rows (B148) of cartridge pockets (B128). Elongate slot (B126) separates and bisects inner rows (B144) of cartridge pockets (B128). Inner rows (B144) and middle rows (B146) are shown as including fifteen cartridge pockets (B128); however, more or fewer cartridge pockets (B128) are envisioned. Outer rows (B148) are shown as including fourteen cartridge pockets (B128); however, more or fewer cartridge pockets (B128) are envisioned.

As shown in FIGS. 9 and 12, engagement protrusions (B130a-f) extend from deck (B124) and are configured to grip tissue (T) or an adjunct material (e.g., a buttress) positioned thereon. As will be described below, cartridge body (B114) includes six different configurations of engagement protrusions (B130a-f). The arrangement of these engagement protrusions (B130a-f) is symmetric about elongate slot (B126). Each engagement protrusion (B130a-f) partially surrounds a respective cartridge pocket (B128). Similar to cartridge pockets (B128), engagement protrusions (B130a-f) are arranged into a plurality of longitudinally extending rows. These longitudinal rows include inner rows (B150), middle rows (B152), and outer rows (B154). While two inner rows (B150), two middle rows (B152), and two outer rows (B154) are shown, more or fewer rows are also envisioned. Inner rows (B150) generally correspond with inner rows (B144) of cartridge pockets (B128). Similarly, middle rows (B152) generally correspond with middle rows (B146) of cartridge pockets (B128), and outer rows (B154) generally correspond with outer rows (B148) of cartridge pockets (B128). Inner rows (B150) are the closest engagement protrusions relative to elongate slot (B126). In other words, inner rows (B150) of engagement protrusions are positioned closer to elongate slot (B126) than middle rows (B152), and middle rows (B152) are positioned closer to elongate slot (B126) than outer rows (B154) of engagement protrusions. As shown, inner rows (B150), middle rows (B152), and outer rows (B154) each extend substantially parallel to elongate slot (B126).

As best shown in FIGS. 9 and 12, engagement protrusions (B130a-c) are the distal most engagement protrusions. Each engagement protrusion (B130a-c) includes a distal lead-in portion (B156). Engagement protrusions (B130a-b) extend between multiple rows. Particularly, engagement protrusion (B130a) extends between inner row (B150) and middle row (B152) on first deck side (B140). Similarly, engagement protrusion (B130b) extends between inner row (B150) and middle row (B152) on second deck side (B142). Engagement protrusions (B130a-c) include planar surfaces (B158a-c)(see FIG. 12). Engagement protrusions (B130c) are the distal most engagement protrusions for outer rows (B154) on first and second deck sides (B140, B142). Each engagement protrusion (B130c-f) extends within a single row (e.g., one of inner row (B150), middle row (B152), and outer rows (B154)) and does not connect with an adjacent row. As shown, longitudinally adjacent engagement protrusions (B130d-f) of inner rows (B150) on first and second deck sides (B140, B142) are linked together (also referred to as joined together) by interconnections (B160). Interconnections (B160) effectively daisy chain together adjacent engagement protrusions (B130d-f) of inner rows (B150).

As shown in FIG. 10, inner row (B150) on first deck side (B140) includes engagement protrusion (B130a) followed by interconnection (B160), engagement protrusion (B130d), interconnection (B160), and engagement protrusion (B130e) in an alternating manner. Particularly, moving proximally, this arrangement is engagement protrusion (B130a), interconnection (B160), engagement protrusion (B130d), interconnection (B160), engagement protrusion (B130e), interconnection (B160), engagement protrusion (B130d), interconnection (B160), engagement protrusion (B130e), interconnection (B160), engagement protrusion (B130d), interconnection (B160), engagement protrusion (B130e), interconnection (B160), engagement protrusion (B130d), interconnection (B160), engagement protrusion (B130e), interconnection (B160), engagement protrusion (B130d), interconnection (B160), engagement protrusion (B130e), interconnection (B160), engagement protrusion (B130d), interconnection (B160), engagement protrusion (B130e), interconnection (B160), engagement protrusion (B130d), interconnection (B160), and engagement protrusion (B130e). Moving proximally, inner row (B150) on second deck side (B142) includes engagement protrusion (B130b) followed by interconnection (B160), engagement protrusion (B130e), interconnection (B160), and engagement protrusion (B130d) in an alternating manner. This difference is because inner row (B150) of second deck side (B142) is a mirror image of inner row (B150) of first deck side (B140). While inner rows (B150) are shown as alternating every engagement protrusion, it is also envisioned that this pattern may vary (e.g., two engagement protrusions (B130d) followed by two engagement protrusions (B130e) each separated by interconnections (B160) etc.).

Moving proximally, middle row (B152) on first deck side (B140) includes engagement protrusion (B130a) followed by a series of longitudinally extending engagement protrusions (B130f). Moving proximally, middle row (B152) on second deck side (B142) includes engagement protrusion (B130b) followed by a series of longitudinally extending engagement protrusions (B130f). As shown, no longitudinally adjacent engagement protrusion (B130a, B130f) of middle rows (B152) is joined together by an interconnection (B160) or any other feature extending from deck (B124). Moving proximally, outer rows (B148) include engagement protrusion (B130c) followed by a series of longitudinally extending engagement protrusions (B130f). Similarly, no longitudinally adjacent engagement protrusion (B130c, B130f) of outer rows (B154) is joined together by an interconnection (B160) or any other feature extending from deck (B124). Except for engagement protrusion (B130a) connecting inner and middle rows (B150, B152) on first deck side (B140) and engagement protrusion (B130b) connecting inner and middle rows (B150, B152) on second deck side (B142), inner rows (B150) are not otherwise linked with either middle row (B146) or outer row (B148) above deck (B124). Engagement protrusions (B130a-f) and interconnections (B160) are integrally formed together as a unitary piece with deck (B124).

Figure 11:
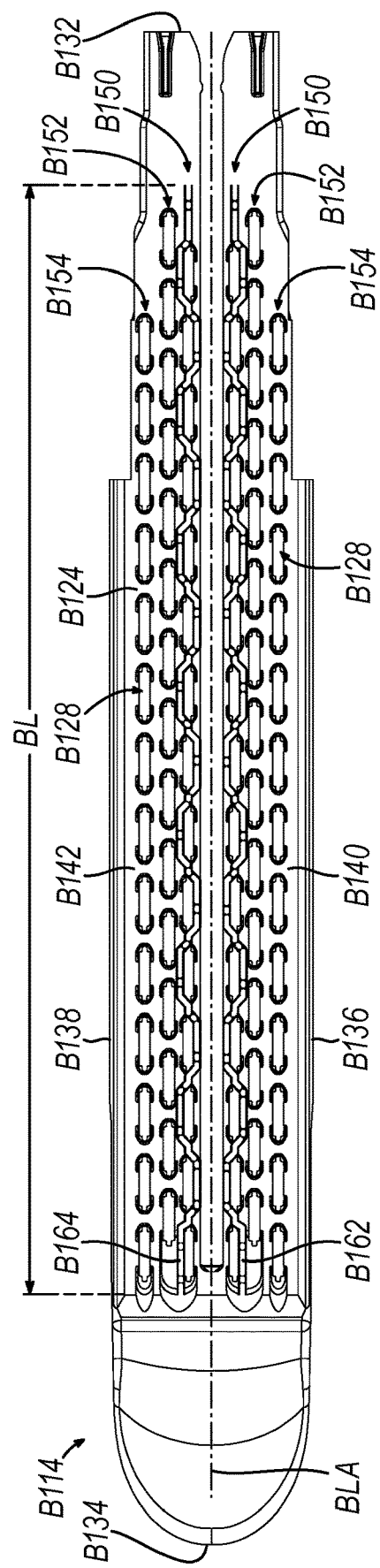
FIG. 11 depicts a top plan view of the cartridge body of FIG. 10 but showing first and second continuous non-linear paths having first and second continuous non-linear cross-sectional areas along the length of inner rows of cartridge pockets.

FIG. 11 shows first and second continuous non-linear raised cross-sectional areas (B162, B164) forming first and second continuous non-linear paths. First continuous non-linear raised cross-sectional area (B162) extends from deck (B124) between adjacent engagement protrusions (B130a, B130d, B130e) joined by interconnections (B160) along an entire length (BL) of inner row (B144) of cartridge pockets (B128). Second continuous non-linear raised cross-sectional area (B164) extends from deck (B124) between adjacent engagement protrusions (B130a, B130d, B130e) joined by interconnections (B160) along entire length (BL) of inner row (B144) of cartridge pockets (B128). First and second continuous non-linear raised cross-sectional areas (B162, B164) are configured to provide increased stiffness to inner rows (B150) of engagement protrusions (B130a-b, B130d-e). First and second continuous non-linear raised cross-sectional areas (B162, B164) increase localized clamping pressure along each adjacent side elongate slot (B126). While first and second continuous non-linear raised cross-sectional areas (B162, B164) are shown as extending along entire length (BL) of inner row (B144) of cartridge pockets (B128), first and/or second continuous non-linear raised cross-sectional areas (B162, B164) may extend along a select portion of inner row (B144) of cartridge pockets (B128) that is less than entire length (BL) of inner row (B144).

Figure 13:
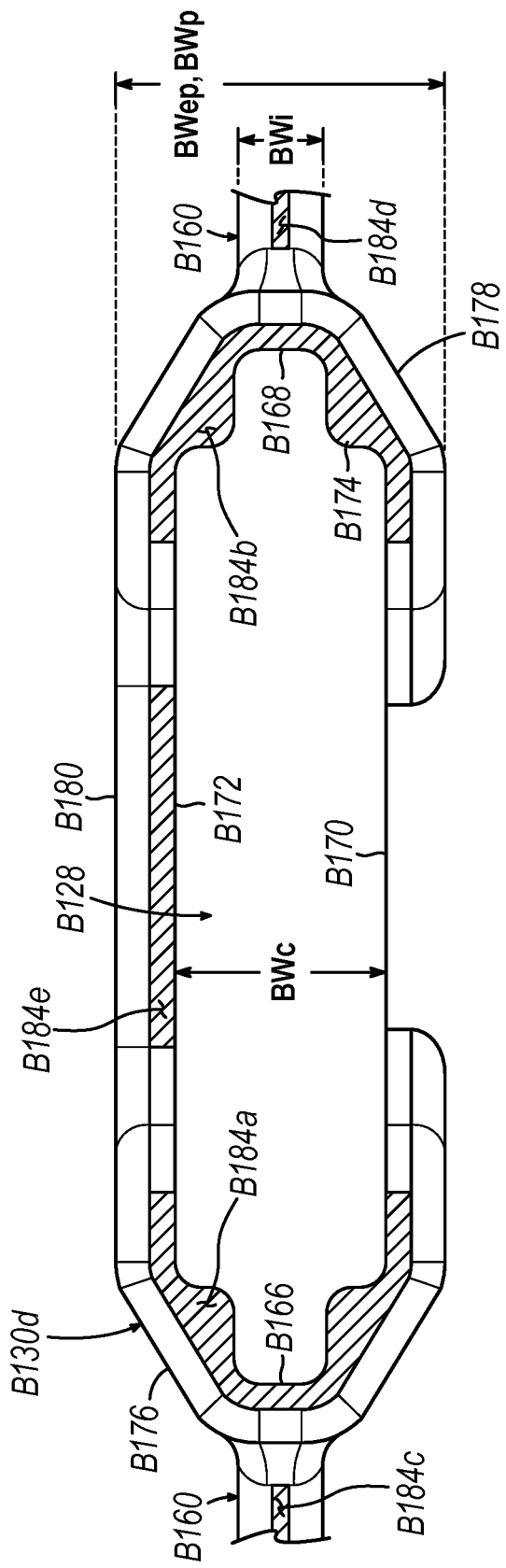
FIG. 13 depicts an enlarged top view of an engagement protrusion and accompanying interconnections partially surrounding a cartridge pocket of the cartridge body of FIG. 12.

FIG. 13 shows an enlarged top view of cartridge pocket (B128), engagement protrusion (B130d), and adjacent interconnections (B160) of inner rows (B150) of FIGS. 9 and 12. Engagement protrusion (B130d) is associated with cartridge pocket (B128). Cartridge pocket (B128) includes a first longitudinal end (B166), a second longitudinal end (B168), a first lateral side (B170), and a second lateral side (B172). Between first and second ends (B166, B168) and first and second lateral sides (B170, B172) are inwardly facing projections (B174) of engagement protrusions (B130a-f). Second longitudinal end (B168) is disposed opposite first longitudinal end (B166). First and second ends (B166, B168) and inwardly facing projections (B174) are configured to guide legs (B117) of staples (B116). First lateral side (B170) is disposed between first and second ends (B166, B168). Second lateral side (B172) is disposed between first and second ends (B166, B168) and opposite to first lateral side (B170). As shown, first and second lateral sides (B170, B172) of cartridge pocket (B128) extend substantially parallel to elongate slot (B126).

With continued reference to FIG. 13, engagement protrusion (B130d) includes a first end portion (B176), a second end portion (B178), and a lateral portion (B180). First end portion (B176) wraps around first longitudinal end (B166) of cartridge pocket (B128). Similarly, second end portion (B178) wraps around second longitudinal end (B168) of cartridge pocket (B128). Lateral portion (B180) extends longitudinally between first and second end portions (B176, B178) longitudinally along at least one of first or second lateral sides (B170, B172) of cartridge pocket (B128). For example, the lateral portion may extend longitudinally between first and second end portions (B176, B178) longitudinally along first lateral side (B170), the lateral portion may extend longitudinally between first and second end portions (B176, B178) longitudinally along first lateral side (B172), or the lateral portion may extend longitudinally between first and second end portions (B176, B178) longitudinally along both of first and second lateral sides (B170, B172). As shown, lateral portion (B180) extends longitudinally along second lateral side (B172) of cartridge pocket (B128). Engagement protrusion (B130d) does not extend along first lateral side (B170) of cartridge pocket (B128) such that first lateral side (B170) opens directly to deck (B124). Lateral portion (B180) extends continuously between first and second end portions (B176, B178) of engagement protrusion (B130d). Interconnections (B160) extend continuously between second end portion (B178) of engagement protrusion (B130d) and a first end portion (B176) of an adjacent engagement protrusion (e.g., engagement protrusions (B130a-b, B130e)). Interconnections (B160) and lateral portion (B180) being adjacent to elongate slot (B126) provide additional compression near the cutline and assist in preventing movement of tissue (T) during firing.

The shaded surfaces of FIG. 13 depict planar surfaces (B184a-e) of engagement protrusion (B130d) and adjacent interconnections (B160). Planar surfaces (B184a-e) are substantially parallel to deck (B124). Planar surface (B184a) is formed between first longitudinal end (B166) and inwardly facing projections (B174) of cartridge pocket (B128) as well as first end portion (B176) of engagement protrusion (B130d). Planar surface (B184b) is formed between second longitudinal end (B168) and inwardly facing projections (B174) of cartridge pocket (B128) as well as second end portion (B178) of engagement protrusion (B130d). Planar surfaces (B184a-b) are generally U-shaped with an increased area due to inwardly facing projections (B174). Planar surface (B184c) is formed by interconnection (B160) and first end portion (B176). Planar surface (B184d) is formed by interconnection (B160) and second end portion (B178). Planar surface (B184e) is formed between second lateral side (B172) of cartridge pocket (B128) and lateral portion (B180) of engagement protrusion (B130d). Planar surfaces (B184c-e) are substantially rectangular.

With continued reference to FIG. 13, engagement protrusion (B130d) has a maximum width (BWep) in the direction transverse to longitudinal axis (BLA). Interconnection (B160) has a maximum width (BWi) in the direction transverse to longitudinal axis (BLA). Maximum width (BWp) of engagement protrusion (B130d) is greater than maximum width (BWi) of interconnection (B160). Cartridge pocket (B128) has a maximum width (BWc) defined by a distance between first and second lateral sides (B170, B172) of cartridge pocket (B128) in the direction transverse to longitudinal axis (BLA). Maximum width (BWc) of cartridge pocket (B128) is greater than maximum width (BWi) of interconnection (B160). First and second end portions (B176, B178) have a maximum width (BWep) in the direction transverse to longitudinal axis (BLA) that is greater than maximum width (BWi) of interconnection (B160).

Figure 14:
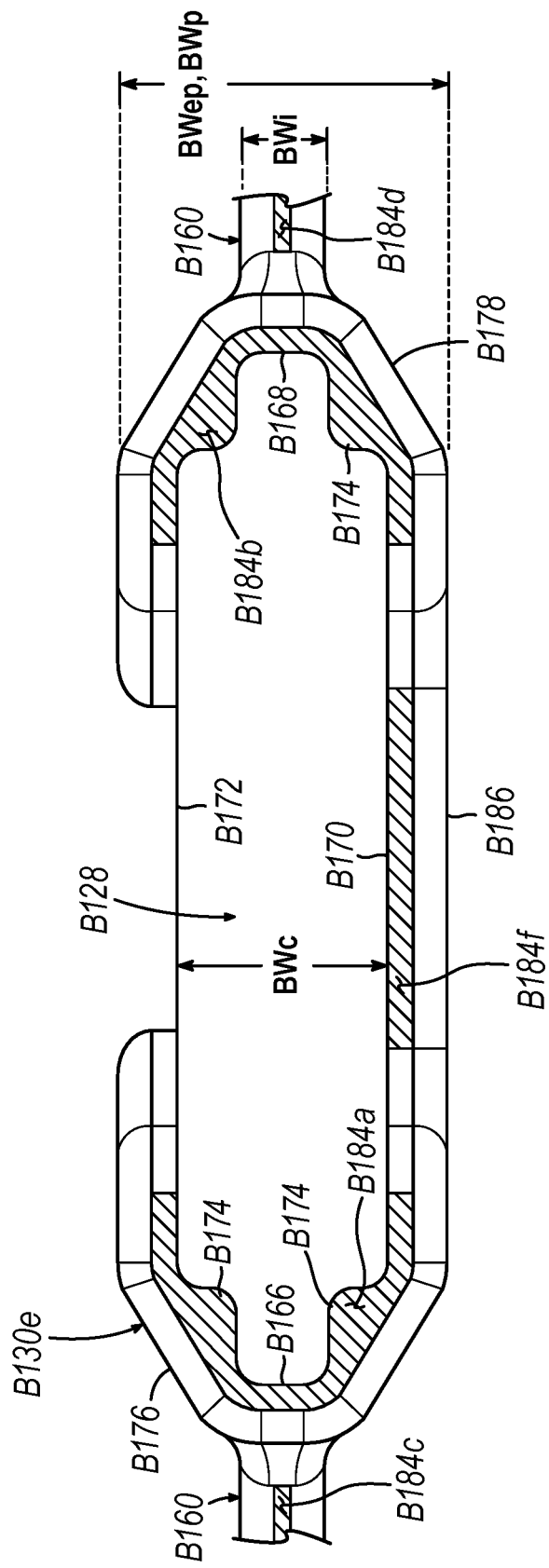
FIG. 14 depicts an enlarged top view of another engagement protrusion and accompanying interconnections partially surrounding a cartridge pocket of the cartridge body of FIG. 12.

FIG. 14 shows an enlarged top view of cartridge pocket (B128), engagement protrusion (B130e), and adjacent interconnections (B160) of inner rows (B150) of FIGS. 9 and 12. Engagement protrusion (B130e) is a mirror image of engagement protrusion (B130d). Similar to engagement protrusion (B130d) includes a first end portion (B176) and a second end portion (B178). Unlike engagement protrusion (B130d) where lateral portion (B180) extends longitudinally along second lateral side (B172), lateral portion (B186) extends longitudinally along first lateral side (B170) of cartridge pocket (B128). Engagement protrusion (B130e) does not extend along second lateral side (B172) of cartridge pocket (B128) such that second lateral side (B172) opens directly to deck (B124). Similar to lateral portion (B180), lateral portion (B186) extends continuously between first and second end portions (B176, B178) of engagement protrusion (B130e). Engagement protrusion (B130e) and adjacent interconnections (B160) includes planar surfaces (B184a-d). Engagement protrusion (B130e) includes planar surface (B184f) instead of planar surface (B184e). Planar surface (B184f) is formed between first lateral side (B170) of cartridge pocket (B128) and lateral portion (B186) of engagement protrusion (B130e). Planar surface (B184f) is substantially rectangular.

Figure 15:
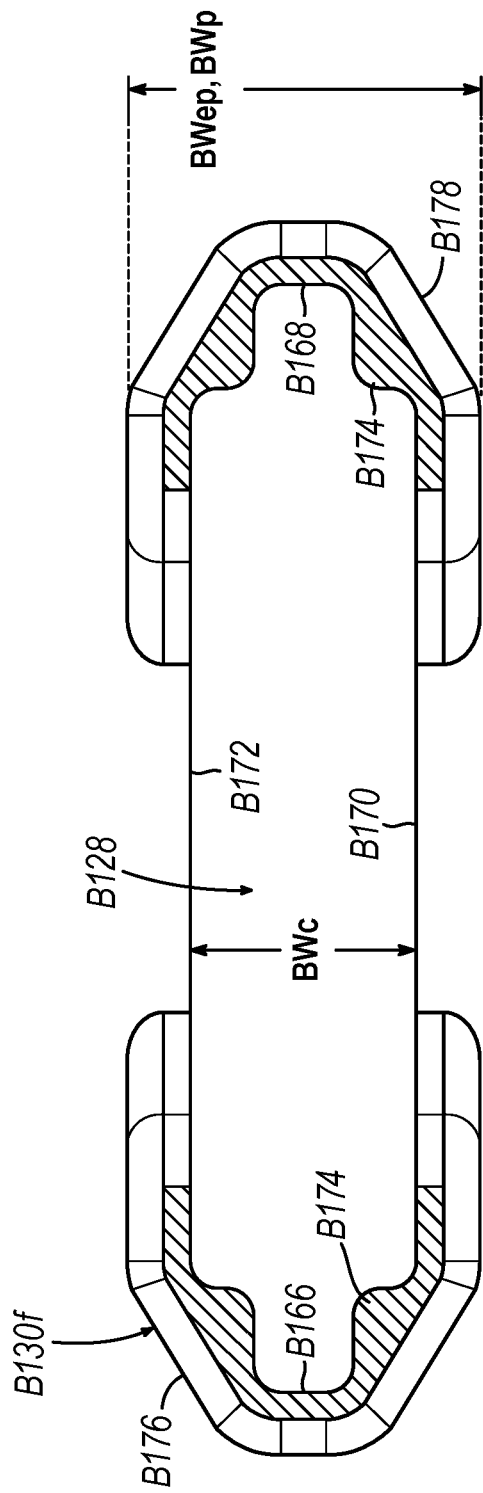
FIG. 15 depicts an enlarged top view of another engagement protrusion partially surrounding a cartridge pocket of the cartridge body of FIG. 12.

FIG. 15 shows an enlarged top view of cartridge pocket (B128) and engagement protrusion (B130f) of middle and outer rows (B152, B154) of FIG. 12. Similar to engagement protrusions (B130d-e), engagement protrusion (B130f) includes a first end portion (B176) and a second end portion (B178). Unlike engagement protrusions (B130d-e), engagement protrusion (B130f) does not include a lateral portion (e.g., lateral portions (B180, B186)). Instead, both first and second lateral sides (B170, B172) of cartridge pocket (B128) open directly to deck (B124). First and second end portions (B176) are not linked together above deck (B124). Additionally, engagement protrusion (B130f) is not linked with another engagement protrusion (B130a-f) using interconnections (B160). In some examples, the absence of a lateral portion with respect to middle and outer rows (B152, B154) is desirable to control pressure applied to tissue (T). For instance, the presence of structures similar to lateral portions (B180, B186) described above may be desirable to fix tissue (T), thereby preventing longitudinal siding during firing. However, the presence of structures similar to lateral portions (B180, B186) can also lead to increased tissue trauma in some circumstances. Thus, it may be desirable incorporate structures similar to lateral portions (B180, B186) in regions where forces are highest during firing and the impact of trauma is less significant (e.g., one or more portions of inner rows (B150)), while omitting structures similar to lateral portions (B180, B186) in regions where forces are lower during firing and the impact of trauma is more significant (e.g., middle and/or outer rows (B162, B154).

Figure 16:
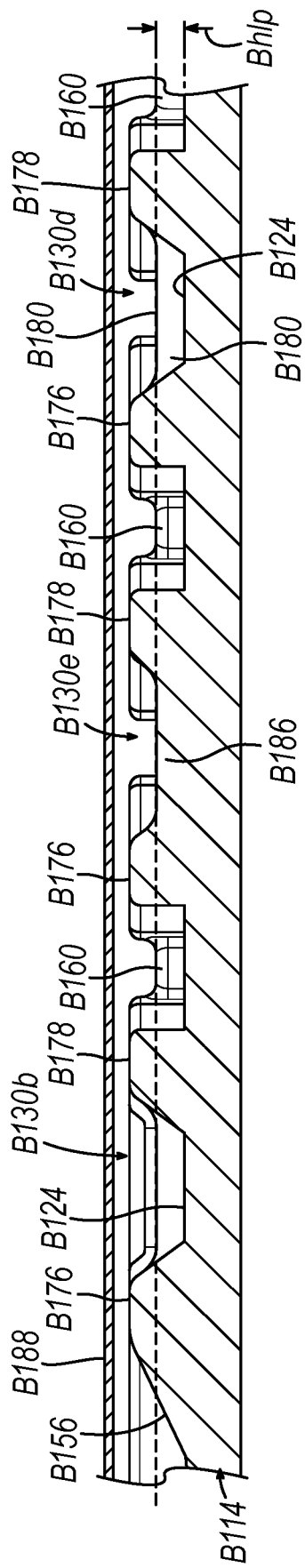
FIG. 16 depicts a partial sectional view of the cartridge body of FIG. 12 taken along line 16-16 of FIG. 12 prior to adhesion of a buttress onto the engagement protrusions of the cartridge body of FIG. 12.

FIG. 16 shows a partial sectional view of cartridge body (B114) of FIG. 12 taken along line 16-16 prior to adhesion of a buttress (B188) onto engagement protrusions (B130a-f) of FIG. 12. As shown, lateral portions (B180, B186) connect first and second end portions (B176, B178). Lateral portions (B180, B186) alternate between adjacent cartridge pockets (B128) along an entire length (BL) of inner row (B144). Considering first row (B250) on second deck side (B140), lateral portions (B180, B186) alternate from first lateral side (B170) (e.g., side adjacent to elongate slot (B126)) to second lateral side (B172) (e.g., side opposite to elongate slot (B126)) moving proximally along elongate slot (B126). Alternating lateral portions (B180, B186) on inner row (B144) of cartridge pockets (B128) may influence tissue retainment during clamping and firing.

Figure 17:
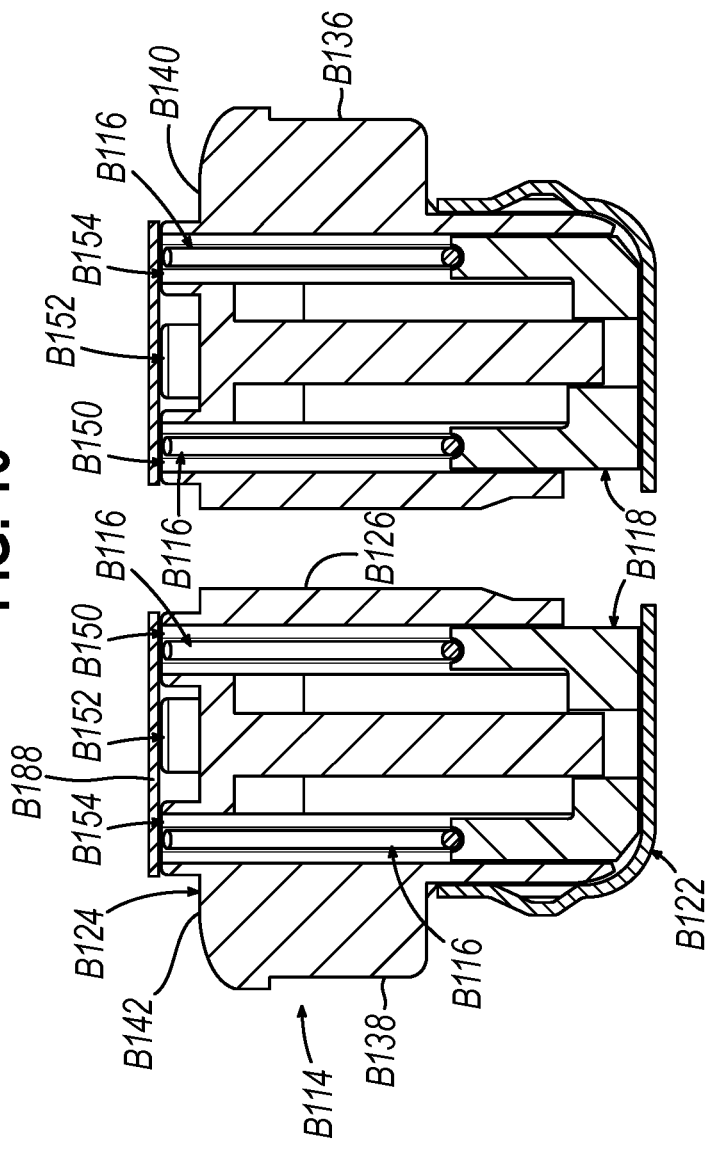
FIG. 17 depicts a partial sectional view of the staple cartridge of FIG. 7 after adhesion of the buttress of FIG. 16 onto the engagement protrusions.

FIG. 17 shows a partial sectional view of staple cartridge (B110) of FIG. 7 after adhesion of buttress (B188) onto engagement protrusions (B130a-f). In some instances, it may be desirable to equip end effector (40) of surgical stapler (10) with an adjunct material, such as a buttress, to reinforce the mechanical fastening of tissue (T) provided by staples (86). In addition to or as an alternative to providing structural support and integrity to a line of staples (86), a buttress (B188) may provide various other kinds of effects such as spacing or gap-filling, administration of therapeutic agents, and/or other effects. In some instances, a buttress may be provided on engagement protrusions (B130d-e). As described above, deck (B124) houses staples (B116), which are driven by staple driver (B118). In some other instances, buttress (B188) may be provided on the surface of an anvil (e.g., anvil (44)) that faces staple cartridge (B110). It should also be understood that a first buttress (B188) may be provided on deck (B124) and a second buttress (not shown) but similar to buttress (B188) is provided on anvil (44) of the same end effector. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and/or U.S. Pat. No. 11,166,724, entitled "Adhesive Distribution on Buttress for Surgical Stapler," issued Nov. 9, 2021, the disclosures of which are incorporated by reference herein. Increased contact area of planar surfaces (B158a-c, B184a-f) may affect adhesion of buttress (B188) to engagement protrusions (B130a-f). While planar surfaces (B158a-c, B184a-f) are the upper most surfaces configured to contact buttress (B188), it is also envisioned that lateral portions (B180, B186) and/or protrusions (B160) may contact buttress (B188).

Figure 18:
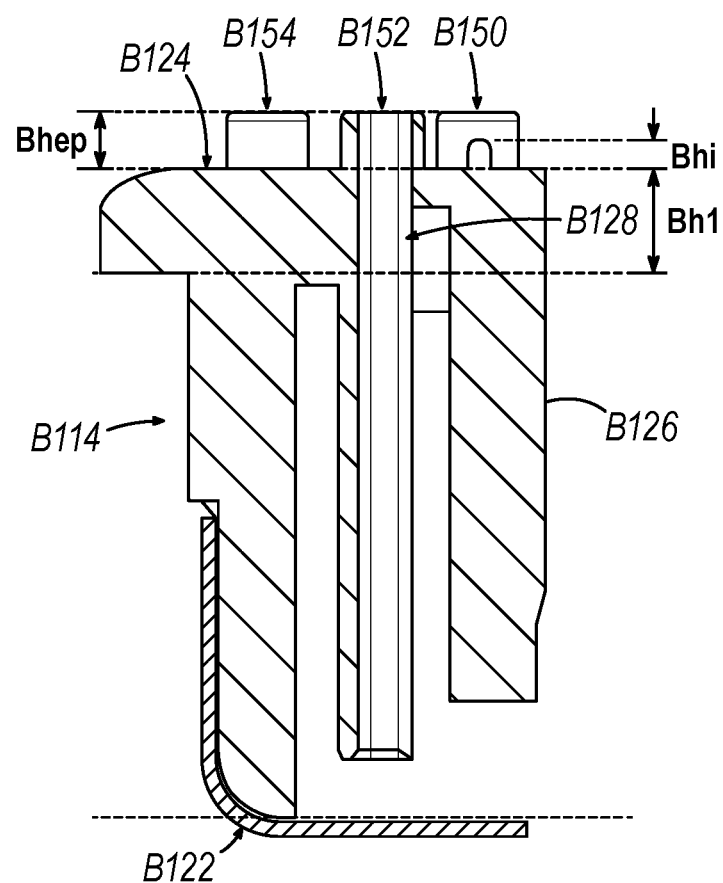
FIG. 18 depicts a partial sectional view of the cartridge body of FIG. 8 taken along a different portion of the cartridge body than FIG. 17.

FIG. 18 shows a partial sectional view of cartridge body (B114) taken along a different portion than FIG. 17. As shown, each engagement protrusion (B130a-f) has the same height (e.g., extends away from deck (B124) the same distance). Particularly, first and second end portions (B176, B178) of engagement protrusions (B130a-f) extend from deck (B124) a maximum height (Bhep). As shown, maximum height (Bhep) is about 0.020 inches (0.508 millimeters). Increasing maximum height (Bhep) accommodates thicker tissue. While first and second end portions (B176, B178) are shown as extending from deck (B124) the same maximum height (Bhep), first end portion (B176) may extend from deck (B124) a greater or lesser amount than second end portion (B178). Lateral portions (B180, B186) of engagement protrusions (B130d-e) extend from deck (B124) a maximum height (Bhlp) (see FIG. 16). Interconnection (B160) extends from deck (B124) a maximum height (Bhi). As shown, maximum height (Bhep) of first and second end portions (B176, B178) is greater than maximum height (Bhi) of interconnection. In other words, maximum height (Bhi) of interconnections (B160) and maximum height of (Bhlp) of lateral portions (B180, B186) are each less than maximum height (Bhep) of first and second end portions (B176, B178). For example, maximum height (Bhi) of interconnections (B160) and maximum height of (Bhlp) of lateral portions (B180, B186) may be each about half of maximum height (Bhep) of first and second end portions (B176, B178). Deck (B124) is planar between engagement protrusions (B130a-c) to proximal end (B132) of cartridge body (B114). Height (Bh1) is about 0.037 inches (0.9398 millimeters).

B. Second Example of a Cartridge Body

Figure 19:
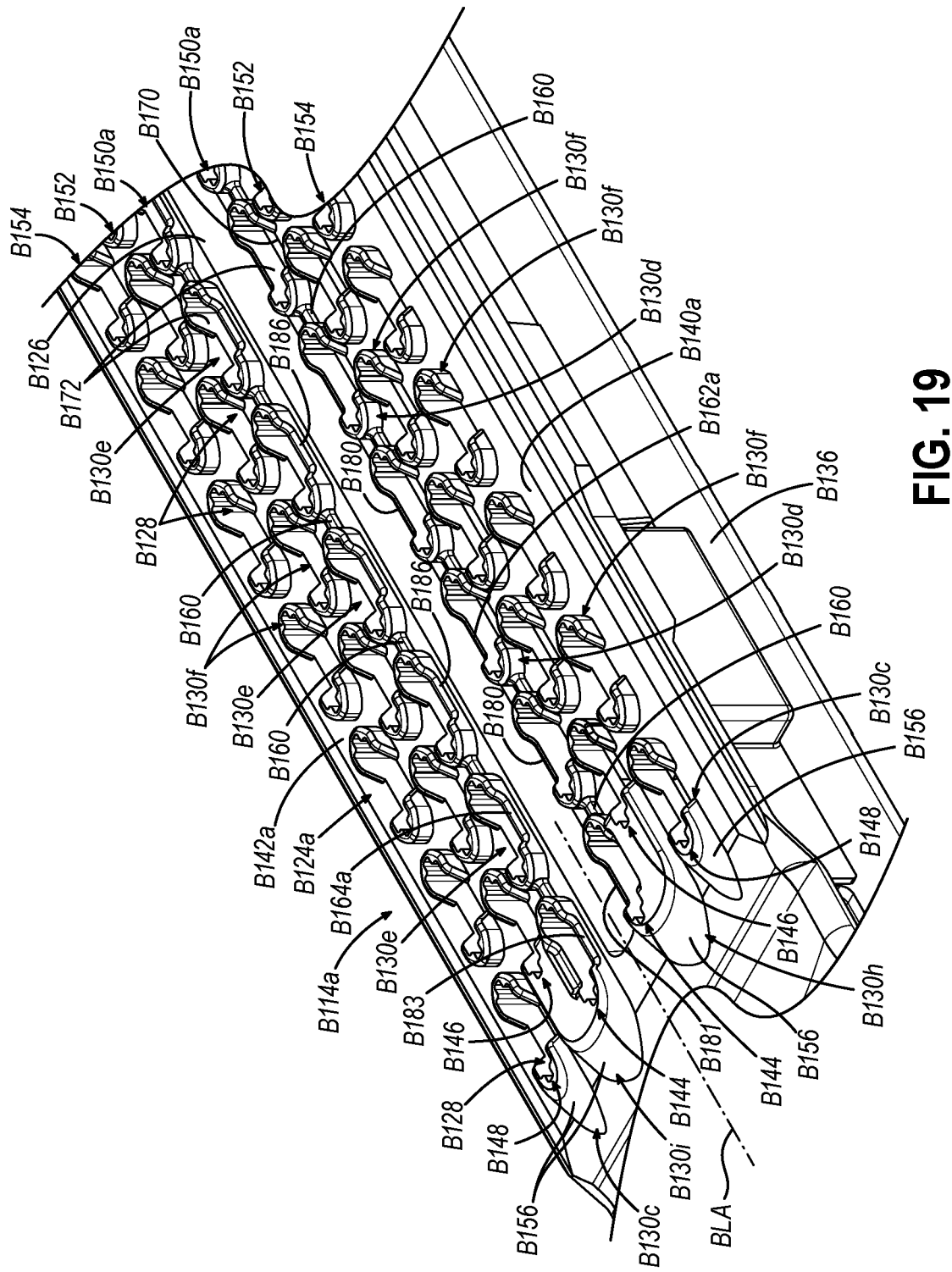
FIG. 19 depicts a partial perspective view of another example of a cartridge body configured to be incorporated into the staple cartridge of FIG. 7 and the end effector of FIG. 2.

FIG. 19 shows a partial perspective view of another example of a cartridge body (B114a) configured to be incorporated into staple cartridge (B110) of FIG. 7 for use with end effector (40) of FIG. 2. Similar to cartridge body (B114), cartridge body (B114a) includes a deck (B124a), elongate slot (B126) formed in deck (B124a), cartridge pockets (B128) formed in deck (B124a), and engagement protrusions (B130c-f, B130h-i) extending outwardly from deck (B124a). Similar to cartridge body (B114), cartridge body (B114a) include inner rows (B144), middle rows (B146), and outer rows (B148) of cartridge pockets (B128). Similar to cartridge body (B114), cartridge body (B114a) includes engagement protrusions (B130c-f, B130h-i) extending from deck (B124a) that are configured to grip tissue or an adjunct material (e.g., a buttress) positioned thereon. Second deck side (B142a) is a mirror image of first deck side (B140a). Longitudinal rows of engagement protrusions include inner rows (B150a), middle rows (B152), and outer rows (B154) and generally correspond to inner rows (B144), middle rows (B146), and outer rows (B148) of cartridge pockets (B128).

Engagement protrusions (B130c, B130h-i) are the distal most engagement protrusions. Engagement protrusion (B130h) is similar to engagement protrusions (B130a), except that engagement protrusion (B130h) includes a lateral portion (B181) instead of opening onto deck (B124a). Engagement protrusion (B130i) is similar to engagement protrusions (B130a), except that engagement protrusion (B130h) includes a lateral portion (B183) instead of opening onto deck (B124a). Engagement protrusions (B130h-i) each completely surround a cartridge pocket (B128). Engagement protrusion (B130c-f) each partially surround a cartridge pocket (B128). Longitudinally adjacent engagement protrusions (B130d-e) of inner rows (B150a) on first and second deck sides (B140a, B142a) are linked together by interconnections (B160). Moving proximally, inner row (B150a) on first deck side (B140a) includes engagement protrusion (B130a) then alternates between interconnection (B160) and engagement protrusion (B130d). This is different from inner row (B150) on first deck side (B140) of FIGS. 9 and 12 that repeats the sequence of engagement protrusion (B130d), interconnection (B160), engagement protrusion (B130e), and interconnection (B160). Moving proximally, inner row (B150a) on second deck side (B142a) includes engagement protrusion (B130b) and then alternates between interconnection (B160) and engagement protrusion (B130e). This is different from inner row (B150) on second deck side (B142a) of FIGS. 9 and 12 that repeats the sequence of engagement protrusion (B130e), interconnection (B160), engagement protrusion (B130d), and interconnection (B160).

As shown in FIG. 19, lateral portions (B180, B186) of engagement protrusions (B130d-e) are adjacent to elongate slot (B126) to provide additional compression near the cutline. As shown, lateral portion (B180) of engagement protrusion (B130d) extends longitudinally along second lateral side (B172) of cartridge pocket (B128) continuously between first and second end portions (B176, B178). Engagement protrusion (B130d) does not extend along first lateral side (B170) of cartridge pocket (B128) such that first lateral side (B170) opens directly to deck (B124a). Lateral portion (B186) extends longitudinally along first lateral side (B170) of cartridge pocket (B128) continuously between first and second end portions (B176, B178). Engagement protrusion (B130e) does not extend along first lateral side (B170) of cartridge pocket (B128) such that first lateral side (B170) opens directly to deck (B124a).

FIG. 19 shows first and second continuous non-linear raised cross-sectional areas (B162a, B164a) forming first and second continuous non-linear paths. First continuous non-linear raised cross-sectional area (B162a) extends from deck (B124a) between longitudinally adjacent engagement protrusions (B130a, B130d) joined by interconnections (B160) along inner row (B144) of cartridge pockets (B128) on first deck side (B140a). Second continuous non-linear raised cross-sectional area (B164a) extends from deck (B124a) between adjacent engagement protrusions (B130a, B130e) joined by interconnections (B160) along the entire length of inner row (B144) of cartridge pockets (B128) on second deck side (B142a). To form first and second continuous non-linear raised cross-sectional areas (B162a, B164a), lateral portions (B180, B186) do not alternate and are adjacent to elongate slot (B126). First and second continuous non-linear raised cross-sectional areas (B162a, B164a) extend along the entire length (not shown) of first and second deck sides (B140a, B142a), but similar to length (BL) of FIG. 11.

C. Third Example of a Cartridge Body

Figure 20:
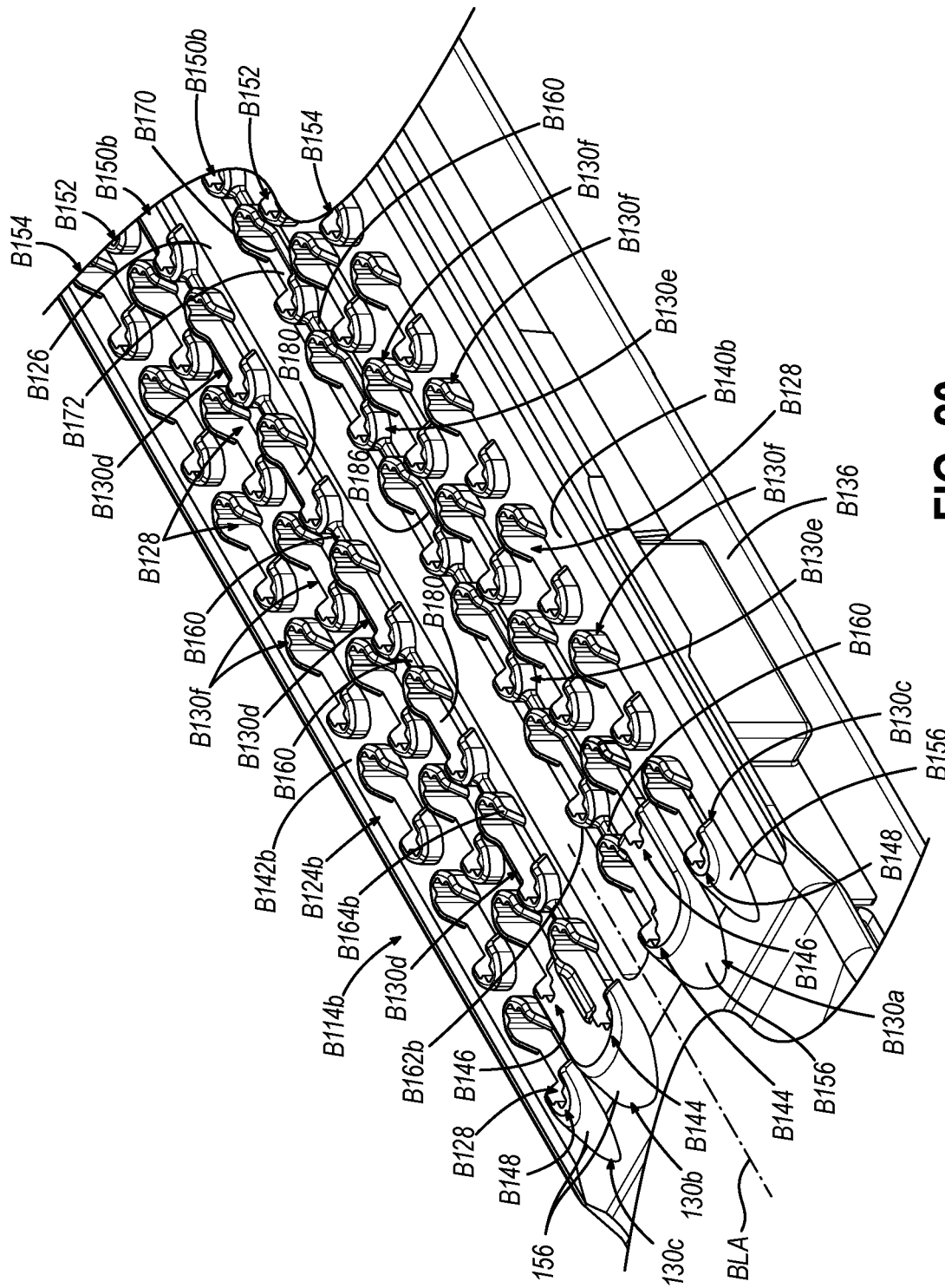
FIG. 20 depicts a partial perspective view of another example of a cartridge body configured to be incorporated into the staple cartridge of FIG. 7 and the end effector of FIG. 2.

FIG. 20 shows a partial perspective view of another example of a cartridge body (B114b) configured to be incorporated into staple cartridge (B110) of FIG. 7 for use with end effector (40) of FIG. 2. Similar to cartridge body (B114), cartridge body (B114b) includes a deck (B124b), an elongate slot (B126) formed in deck (B124b), a plurality of cartridge pockets (B128) formed in deck (B124b), and a plurality of engagement protrusions (B130a-f) extending outwardly from deck (B124b). Each cartridge pocket (B128) is configured to slidably house an unformed staple such as staple (B116) and a respective staple driver such as staple driver (B118). Similar to cartridge body (B114), cartridge body (B114b) include inner rows (B144), middle rows (B146), and outer rows (B148) of cartridge pockets (B128). Similar to cartridge body (B114), cartridge body (B114b) includes engagement protrusions (B130a-f) extending from deck (B124b) that are configured to grip tissue or an adjunct material (e.g., a buttress) positioned thereon. Each engagement protrusion (B130a-f) partially surrounds a respective cartridge pocket (B128). The arrangement of these engagement protrusions (B130a-f) is symmetric about elongate slot (B126). Second deck side (B140) of cartridge body (B114) is a mirror image of first deck side (B140) of cartridge body (B114). Longitudinal rows of engagement protrusions include inner rows (B150b), middle rows (B152), and outer rows (B154) and generally correspond to inner rows (B144), middle rows (B146), and outer rows (B148), respectively.

Similar to cartridge body (B114), engagement protrusions (B130a-c) are the distal most engagement protrusions. Longitudinally adjacent engagement protrusions (B130d-f) of inner rows (B150) on first and second deck sides (B140, B142) are linked together by interconnections (B160). Moving proximally, inner row (B150b) on first deck side (B140b) includes engagement protrusion (B130a) then alternates between interconnection (B160) and engagement protrusion (B130e). This is different from inner row (B150) on first deck side (B140b) of FIGS. 9 and 12 that repeats the sequences of engagement protrusion (B130e), interconnection (B160), engagement protrusion (B130e), and interconnection (B160). Moving proximally, inner row (B150b) on second deck side (B142b) includes engagement protrusion (B130b) and then alternates between interconnection (B160) and engagement protrusion (B130d). This is different from inner row (B150) on second deck side (B142) of FIGS. 9 and 12 that alternates between engagement protrusion (B130e), interconnection (B160), engagement protrusion (B130d), and interconnection (B160).

As shown in FIG. 20, lateral portions (B180, B186) are disposed opposite to elongate slot (B126). On first deck side (B140b), lateral portion (B186) of engagement protrusion (B130e) extends longitudinally along first lateral side (B170) of cartridge pocket (B128). Engagement protrusion (B130e) does not extend along second lateral side (B172) of cartridge pocket (B128) such that second lateral side (B172) opens directly to deck (B124b) adjacent elongate slot (B126). Lateral portion (B186) extends continuously between first and second end portions (B176, B178) of engagement protrusion (B130e). On second deck side (B142b), lateral portion (B180) of engagement protrusion (B130d) extends longitudinally along second lateral side (B172) of cartridge pocket (B128). Engagement protrusion (B130d) does not extend along first lateral side (B170) of cartridge pocket (B128) such that first lateral side (B170) opens directly to deck (B124b) adjacent elongate slot (B126). Lateral portion (B180) extends continuously between first and second end portions (B176, B178) of engagement protrusion (B130d). As shown in FIG. 20, lateral portions (B180, B186) do not alternate and are on the side opposite to elongate slot (B126).

FIG. 20 shows first and second continuous non-linear raised cross-sectional areas (B162b, B164b) forming first and second continuous non-linear paths. First continuous non-linear raised cross-sectional area (B162b) extends from deck (B124b) between adjacent engagement protrusions (B130a, B130e) joined by interconnections (B160) along inner row (B144) of cartridge pockets (B128) on first deck side (B140b). Second continuous non-linear raised cross-sectional area (B164a) extends from deck (B124) between adjacent engagement protrusions (B130b, 130d) joined by interconnections (B160) along inner row (B144) of cartridge pockets (B128) on second deck side (B142b). First and second continuous non-linear raised cross-sectional areas (B162b, B164b) extend along the entire length (not shown) of first and second deck sides (B140b, B142b), but similar to length (BL) of FIG. 11.

D. Fourth Example of a Cartridge Body

Figure 21:
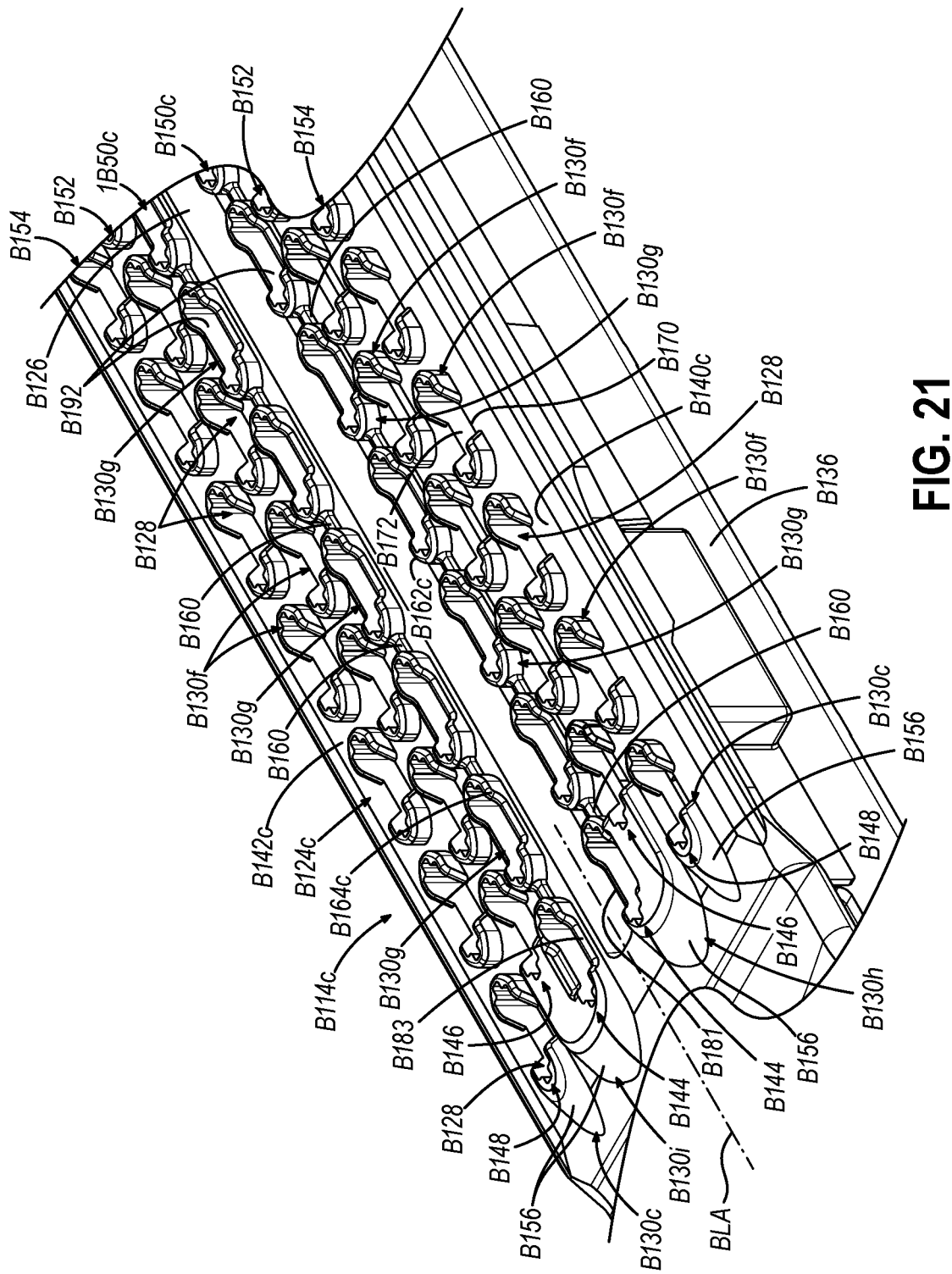
FIG. 21 depicts a partial perspective view of another example of a cartridge body configured to be incorporated into the staple cartridge of FIG. 7 and the end effector of FIG. 2.

FIG. 21 shows a partial perspective view of another example of a cartridge body (B114c) configured to be incorporated into staple cartridge (B110) of FIG. 7 for use with end effector (40) of FIG. 2. Similar to cartridge body (B114), cartridge body (B114c) includes a deck (B124c), an elongate slot (B126) formed in deck (B124c), a plurality of cartridge pockets (B128) formed in deck (B124c), and a plurality of engagement protrusions (B130c, B130f-i) extending outwardly from deck (B124c). Each cartridge pocket (B128) is configured to slidably house an unformed staple similar to staple (B116) and a respective staple driver similar to staple driver (B118). Similar to cartridge body (B114), cartridge body (B114c) includes inner rows (B144), middle rows (B146), and outer rows (B148) of cartridge pockets (B128). Engagement protrusions (B130c, B130f-i) extend from deck (B124c) and are configured to grip tissue or an adjunct material (e.g., a buttress) positioned thereon. The arrangement of these engagement protrusions (B130c, B130f-i) is symmetric about elongate slot (B126). Second deck side (B140) of cartridge body (B114) is a mirror image of first deck side (B140) of cartridge body (B114). Longitudinal rows of engagement protrusions include inner rows (B150c), middle rows (B152), and outer rows (B154) and generally correspond to inner rows (B144), middle rows (B146), and outer rows (B148), respectively.

Similar to cartridge body (B114a), engagement protrusions (B130c, B130h-i) are the distal most engagement protrusions. Longitudinally adjacent engagement protrusions (B130g-i) of inner rows (B150) on first and second deck sides (B140c, B142c) are linked together by interconnections (B160). Moving proximally, inner row (B150c) on first deck side (B140c) includes engagement protrusion (B130h) then alternates between interconnection (B160) and engagement protrusion (B130g). Moving proximally, inner row (B150c) on second deck side (B142c) includes engagement protrusion (B130i) and then alternates between interconnection (B160) and engagement protrusion (B130g).

FIG. 21 shows first and second continuous non-linear raised cross-sectional areas (B162c, B164c) forming first and second continuous non-linear paths. First continuous non-linear raised cross-sectional area (B162c) extends from deck (B124c) between adjacent engagement protrusions (B130g-h) joined by interconnections (B160) along inner row (B144) of cartridge pockets (B128) on first deck side (B140c). Second continuous non-linear raised cross-sectional area (B164c) extends from deck (B124c) between adjacent engagement protrusions (B130g, B130i) joined by interconnections (B160) along inner row (B144) of cartridge pockets (B128) on second deck side (B142c). Each engagement protrusion (B130g-i) of inner row (B150c) surrounds a respective cartridge pocket (B128) of inner rows (B144) of cartridge pockets (B128). First and second continuous non-linear raised cross-sectional areas (B162c, B164c) increase the localized pressure in the area adjacent to elongate slot (B126). First and second continuous non-linear raised cross-sectional areas (B162c, B164c) extend along the entire length (not shown) of first and second deck sides (B140c, B142c), but similar to length (BL) of FIG. 11.

Figure 22:
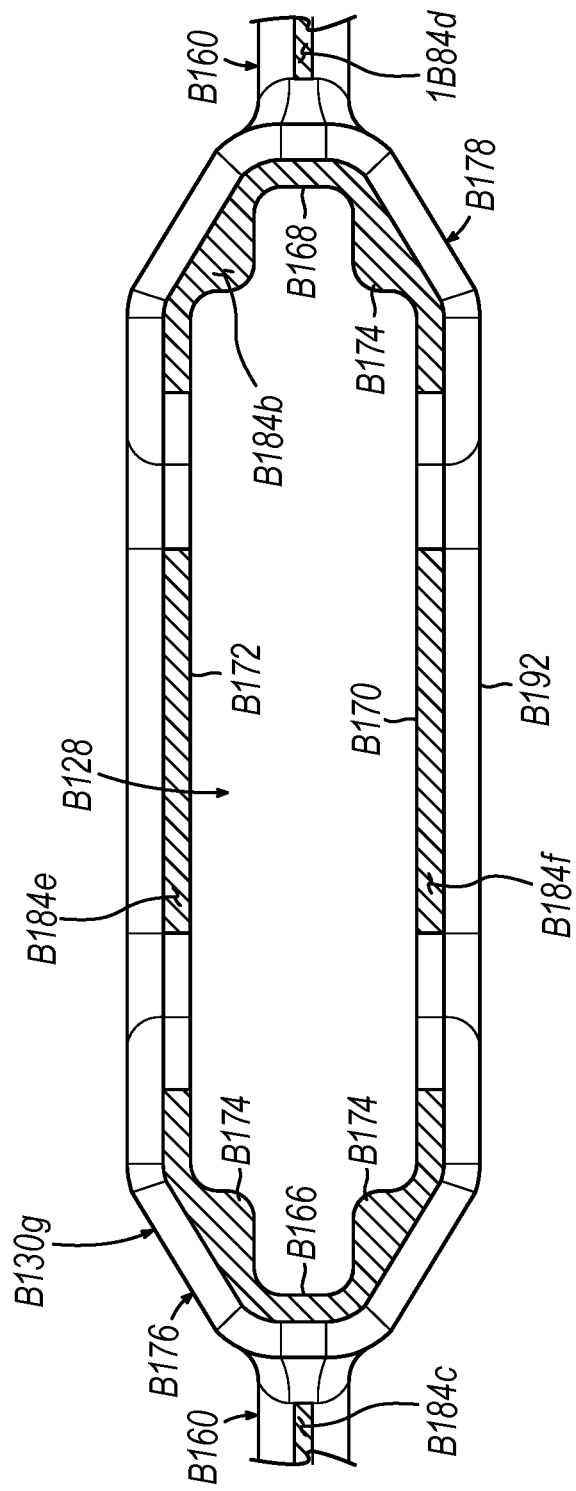
FIG. 22 depicts an enlarged top view of another engagement protrusion and accompanying interconnections completely surrounding a cartridge pocket of FIG. 21.

FIG. 22 shows an enlarged top view of cartridge pocket (B128), engagement protrusion (B130g), and adjacent interconnections (B160). Similar to engagement protrusions (B130d-e), engagement protrusion (B130g) includes a first end portion (B176) and a second end portion (B178). Unlike engagement protrusion (B130d-e), engagement protrusion (B130g) includes lateral portion (B192). Lateral portion (B192) extends longitudinally along both first lateral side (B170) and second lateral side (B172) of cartridge pocket (B128). In other words, first end portion (B176), second end portion (B178), and lateral portion (B192) collectively surround cartridge pocket (B128). Engagement protrusion (B130g) includes planar surfaces (B184e-f) that are substantially rectangular. As shown, lateral portion (B192) is both adjacent to and opposite to elongate slot (B126) to provide additional compression near the cutline.

E. Fifth Example of a Cartridge Body

Figure 23:
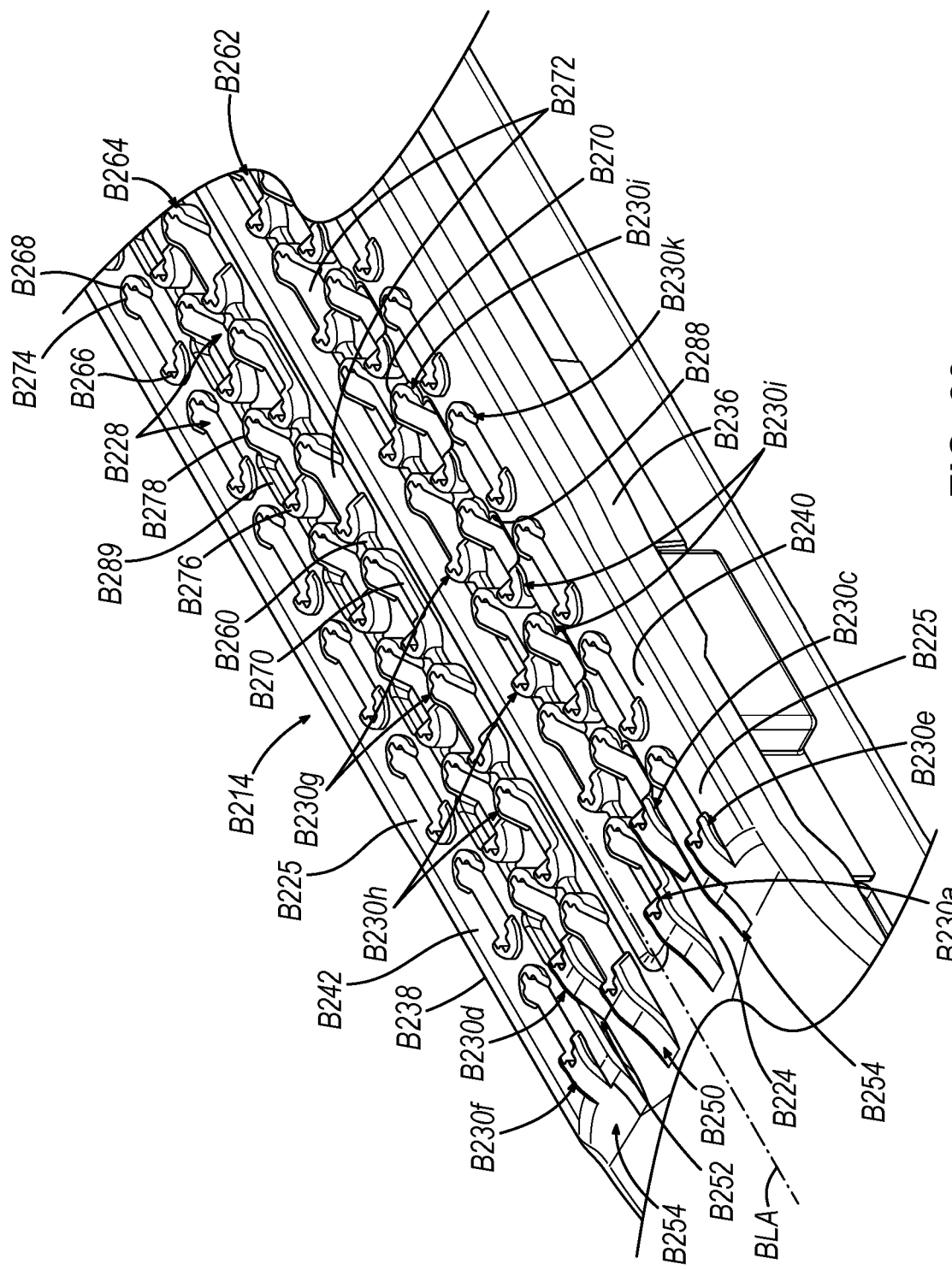
FIG. 23 depicts a partial perspective view of another example of a cartridge body configured to be incorporated into the staple cartridge of FIG. 7 and the end effector of FIG. 2.
Figure 24:
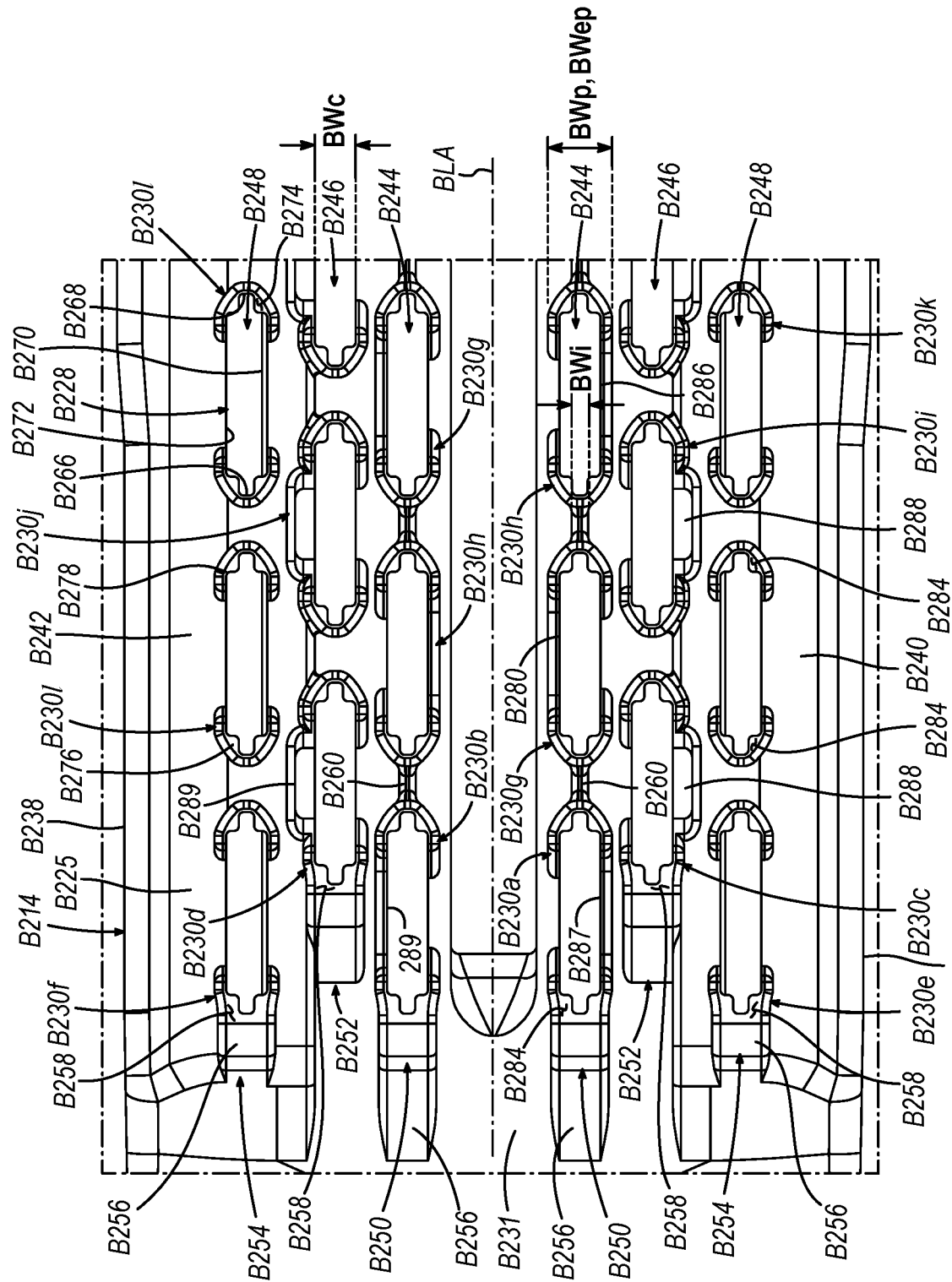
FIG. 24 depicts a partial top plan view of the cartridge body of FIG. 23.
Figure 25:
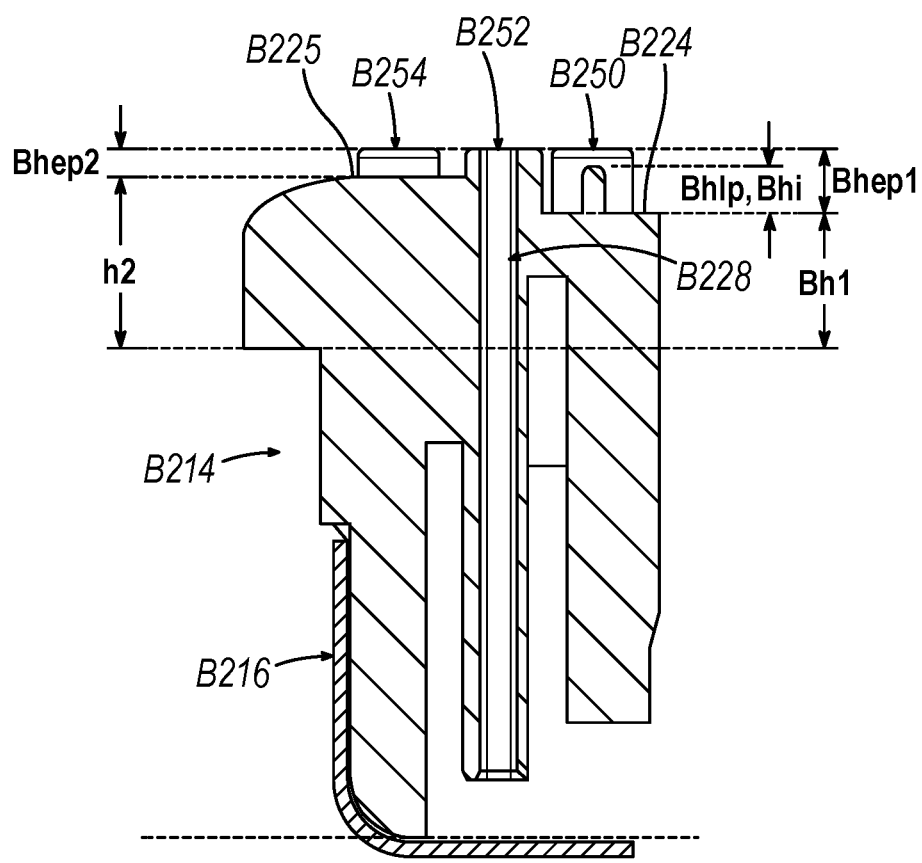
FIG. 25 depicts a partial sectional view of the cartridge body of FIG. 23 and an accompanying tray.

FIGS. 23-25 show another example of a cartridge body (B214) configured to be incorporated into staple cartridge (B110) of FIG. 7 for use with end effector (40) of FIG. 2. Cartridge body (B214) is similar to cartridge body (B114) described above except as otherwise described below. Similar to cartridge body (B114), cartridge body (B214) includes a deck (B224), an elongate slot (B226) formed in deck (B224), a plurality of cartridge pockets (B228) formed in deck (B224), and a plurality of engagement protrusions (B230a-1) extending outwardly from deck (B224). Deck (B224) is configured to compress tissue against an anvil (not shown), but similar to anvil (44). Deck (B224) is defined by cartridge body (B214) and is shown as upwardly facing. Unlike decks (B124, B124a-c) which are substantially planar, deck (B224) has a stepped orientation and is non-planar. Particularly, deck (B224) has a step (B225) extending from between middle and outer rows (B246, B248). Elongate slot (B226) extends along a longitudinal axis (BLA) of cartridge body (B214). Elongate slot (B226) opens upwardly through deck (B224) and terminates at a connecting portion (B231). Elongate slot (B226) is configured to slidably receive a knife therein similar to elongate slot (B126). Cartridge pockets (B228) are configured to house staples (not shown) but similar to staples (B116) and staple drivers (not shown) but similar to staple drivers (B118). As shown, cartridge body (B214) includes a first lateral side (B236) and a second lateral side (B238) disposed opposite first lateral side (B236).

FIGS. 23-24 show cartridge pockets (B228) arranged into six longitudinally extending rows. Elongate slot (B226) separates three rows on a first deck side (B240) from three additional rows on a second deck side (B242). These longitudinal rows include inner rows (B244), middle rows (B246), and outer rows (B248). Similar to cartridge body (B114), inner row (B250) of second deck side (B242) is a mirror image of inner row (B250) of first deck side (B240). Inner rows (B244) are the closest cartridge pockets (B228) relative to elongate slot (B226). Engagement protrusions (B230a-1) extend from deck (B224) and are configured to grip tissue (T) or an adjunct material (e.g., buttress (B188)) positioned thereon. Cartridge body (B214) includes twelve different configurations of engagement protrusions (B230a-1). The arrangement of these engagement protrusions (B230a-1) is symmetric about elongate slot (B226). In other words, second deck side (B242) of cartridge body (B214) is a mirror image of first deck side (B240) of cartridge body (B214). Similar to cartridge pockets (B228), engagement protrusions (B230a-1) are arranged into a plurality of longitudinally extending rows. These longitudinal rows include inner rows (B250), middle rows (B252), and outer rows (B254). Inner rows (B250) generally correspond with inner rows (B244) of cartridge pockets (B228), middle rows (B252) generally correspond with middle rows (B246) of cartridge pockets (B228), and outer rows (B254) generally correspond with outer rows (B248) of cartridge pockets (B228). As shown, inner rows (B250), middle rows (B252), and outer rows (B254) each extend substantially parallel to elongate slot (B226). Inner rows (B250) are the closest engagement protrusions relative to elongate slot (B226).

With continued reference to FIGS. 23-24, engagement protrusions (B230a-f) are the distal most engagement protrusions. Each engagement protrusion (B230a-f) includes a distal lead-in portion (B256). Engagement protrusions (B230a-f) include planar surfaces (B258). Engagement protrusions (B230a-b, B230g-h) extend within a single row and do not connect with an adjacent row. As shown in FIG. 24, engagement protrusion (B230a) includes a lateral portion (B287), and engagement protrusion (B230a) includes a lateral portion (B289). Engagement protrusion (B230g) is similar to engagement protrusion (B130d) and includes a lateral portion (B280) (see FIG. 24) similar to lateral portion (B180). Engagement protrusion (B230h) is similar to engagement protrusions (B130e) and includes a lateral portion (B286) (see FIG. 24) similar to lateral portion (B186). Engagement protrusions (B230c-f, B230i-1) in middle and outer rows (B252, B254) connect due to step (B225) but are not linked together above step (B225) or outside of step (B225). As shown, longitudinally adjacent engagement protrusions (B230a-b, B230g-h) of inner rows (B250) on first and second deck sides (B240, B242) are linked together by interconnections (B260). Interconnections (B260) are similar to interconnections (B160). Moving proximally, inner row (B250) on first deck side (B240) includes engagement protrusion (B230a) followed by interconnection (B260), followed by engagement protrusion (B230g), followed by interconnection (B260), followed by engagement protrusion (B230h), with the sequence of engagement protrusion (B230g), interconnection (B260), and engagement protrusion (B230h) interconnection (B260) repeating in an alternating manner. Moving proximally, inner row (B250) on second deck side (B242) includes engagement protrusion (B230b) followed by interconnection (B260), followed by engagement protrusion (B230h), followed by interconnection (B260), followed by engagement protrusion (B230g), with the sequence of interconnection (B260), engagement protrusion (B230h), interconnection (B260), and engagement protrusion (B230g) repeating in an alternating manner.

Similar to first and second continuous non-linear raised cross-sectional areas (B162, B164), cartridge body (B214) includes first and second continuous non-linear raised cross-sectional areas (B262, B264) (see FIG. 24) that form first and second continuous non-linear paths. The first continuous non-linear raised cross-sectional area (B262) extends from deck (B224) between adjacent engagement protrusions (B230a, B230g, B230h) joined by interconnections (B260)

along the entire length of inner row (B244) of cartridge pockets (B228). The second continuous non-linear raised cross-sectional area (B264) extends from deck (B224) between longitudinally adjacent engagement protrusions (B230b, B230h, B230g) joined by interconnections (B260) along the inner row (B244) of cartridge pockets (B228). These continuous non-linear raised cross-sectional areas (B262, B264) are configured to provide increased stiffness to inner rows (B250) and/or increased localized clamping pressure around elongate slot (B226).

Similar to cartridge pockets (B128), cartridge pockets (B228) each include a first longitudinal end (B266), a second longitudinal end (B268), a first lateral side (B270), and a second lateral side (B272). Between first and second longitudinal ends (B266, B268) and first and second lateral sides (B270, B272) are inwardly facing projections (B274), similar to inwardly facing projections (B174). As shown, first and second lateral sides (B270, B272) of cartridge pocket (B228) extend substantially parallel to elongate slot (B226).

Inner rows (B250) are not linked with either middle row (B246) or outer rows (B248) above deck (B224). Except for step (B225), middle and outer rows (B252, B254) are not otherwise linked together. Engagement protrusions (B230a-1) and interconnections (B260) are integrally formed together as a unitary piece with deck (B224). Engagement protrusion (B230g) includes a first end portion (B276), a second end portion (B278), and lateral portion (B280). First end portion (B276) wraps around first longitudinal end (B266) of cartridge pocket (B228). Lateral portion (B280) being adjacent to elongate slot (B226) provides additional compression near the cutline. As shown, lateral portion (B280) extends longitudinally along first lateral side (B270) of cartridge pocket (B228) but not on second lateral side (B272) of cartridge pocket (B228) which instead opens directly to deck (B224). Interconnections (B260) extend between second end portion (B278) of engagement protrusion (B230d) and a first end portion (B276) of an adjacent engagement protrusion. Planar surfaces (B284) are substantially parallel to deck (B224).

Middle row (B252) on first deck side (B240) includes engagement protrusion (B230c) followed by a series of engagement protrusions (B230i). Middle row (B252) on second deck side (B242) includes engagement protrusion (B230d) followed by a series of engagement protrusions (B230j). As shown, no longitudinally adjacent engagement protrusion of middle or outer rows (B252, B254) is joined together by an interconnection (B260) or any other feature extending from deck (B224) other than step (B225) of deck (B224). Engagement protrusions (B230c, B230i) open to deck (B224) on second lateral side (B272), and include a U-shaped wall (B288) on first lateral side (B270) of cartridge pocket (B228). Engagement protrusions (B230d, B230j) include a U-shaped wall (B291) on second lateral side (B272), and open to deck (B224) on first lateral side (B270) of cartridge pocket (B228).

Outer row (B254) on first deck side (B240) includes engagement protrusion (B230e) followed by a series of engagement protrusions (B230k). Outer row (B254) on second deck side (B242) includes engagement protrusion (B230f) followed by a series of engagement protrusions (B230l). For each of engagement protrusions (B230e-f, B230k-1), both first and second lateral sides (B270, B272) of cartridge pocket (B228) open directly onto deck (B224). Unlike engagement protrusions (B230g-h), engagement protrusions (B230e-f, B230k-1) do not include a lateral portion (e.g., lateral portions (B280, B286)). As shown, no longitudinally adjacent engagement protrusion of middle or outer rows (B252, B254) is joined together by an interconnection (B260) or any other feature extending from deck (B224) other than step (B225) of deck (B224).

As shown in FIG. 24, engagement protrusions (B230a-h, B230k) have a maximum width (BWp) in the direction transverse to longitudinal axis (BLA). Interconnection (B260) has a maximum width (BWi) in the direction transverse to longitudinal axis (BLA). Maximum width (BWp) of engagement protrusions (B230a-h, B230k) is greater than maximum width (BWi) of interconnection (B260). Cartridge pockets (B228) have a maximum width (BWc) defined by a distance between first and second lateral sides (B270, B272) of cartridge pocket (B228) in the direction transverse to longitudinal axis (BLA). Maximum width (BWc) of cartridge pocket (B228) is greater than maximum width (BWi) of interconnection (B260). First and second end portions (B276, B278) have a maximum width (BWep) in the direction transverse to longitudinal axis (BLA) that is greater than maximum width (BWi) of interconnection (B260).

FIG. 25 shows cartridge body (B214) and tray (B216). As shown, for inner row (B250), first and second end portions (B276, B278) extend from deck (B224) a maximum height (Bhep1). Interconnection (B260) extends from deck (B224) a maximum height (Bhi). As shown, maximum height (Bhep1) of first and second end portions (B276, B278) of inner row (B250) is greater than maximum height (Bhi) of interconnection (B260). For middle row (B252), inner side extends from deck (B224) a maximum height (Bhep1), and outer row (B254) extends from step (B225) of deck (B224) a maximum height (Bhep2). Maximum height (Bhep1) of first and second end portions (B276, B278) of inner row (B250) is about 0.025 inches (0.635 millimeters). As shown, maximum height (Bhep2) of first and second end portions (B276, B278) of outer row (B254) is about 0.010 inches (0.254 millimeters). As shown, height (Bh1) is about 0.052 inches (1.3208 millimeters), height (Bh2) is about 0.067 inches (1.7018 millimeters).

F. Sixth Example of a Cartridge Body

Figure 26:
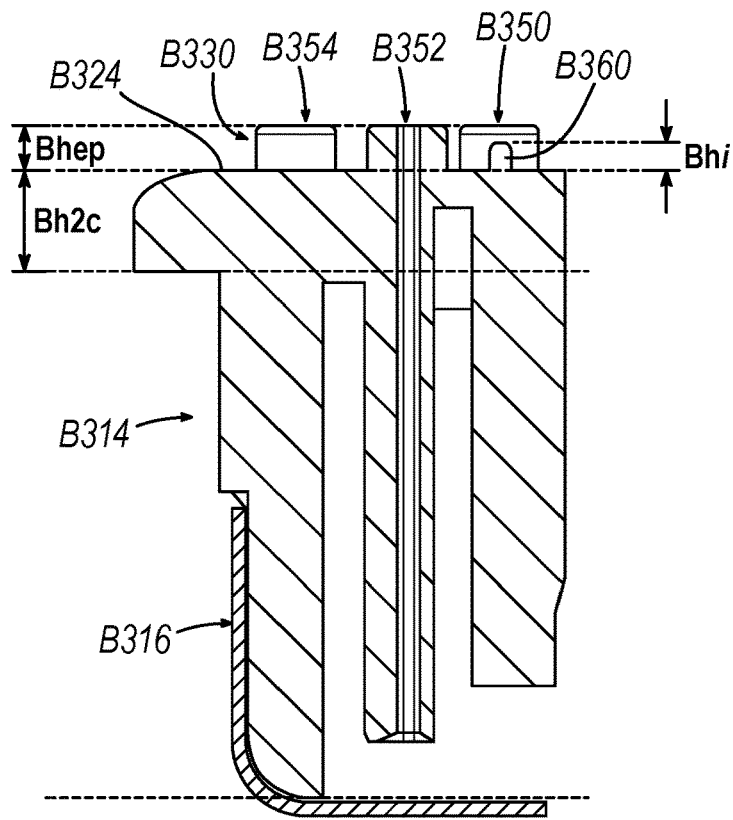
FIG. 26 depicts a partial sectional view of another example of a cartridge body and an accompanying tray configured to be incorporated into the staple cartridge of FIG. 7 and the end effector of FIG. 2.

FIG. 26 shows a partial sectional view of another example of a cartridge body (B314) and accompanying tray (B316) configured to be incorporated into staple cartridge (B110) of FIG. 7 for use with end effector (40) of FIG. 2. Cartridge body (B314) is similar to cartridge body (B114) described and shown above with reference to FIGS. 7-18. Engagement protrusions (B330), similar to engagement protrusions (B130a-f), include inner rows (B350), middle rows (B352), and outer rows (B354) that extend from a deck (B324). As shown in FIG. 26, maximum height (Bhep) of engagement protrusions (B330) is about 0.016 inches (0.4064 millimeters), and height (Bh2c) is about 0.037 inches (0.9398 millimeters). Interconnections (B360) have a max height (Bhi) that is about half of maximum height (Bhep) of engagement protrusions (B330). Interconnections (B360) are similar to interconnections (B160). Deck (B324) is shown as being substantially planar.

G. Seventh Example of a Cartridge Body

Figure 27:
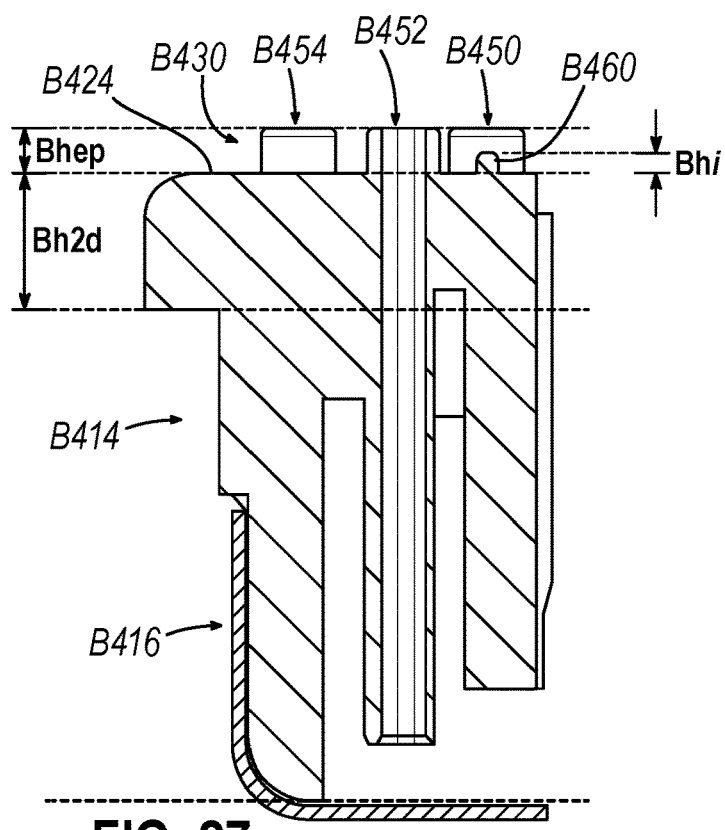
FIG. 27 depicts a partial sectional view of another example of a cartridge body and an accompanying tray configured to be incorporated into the staple cartridge of FIG. 7 and the end effector of FIG. 2.
Figure 28:
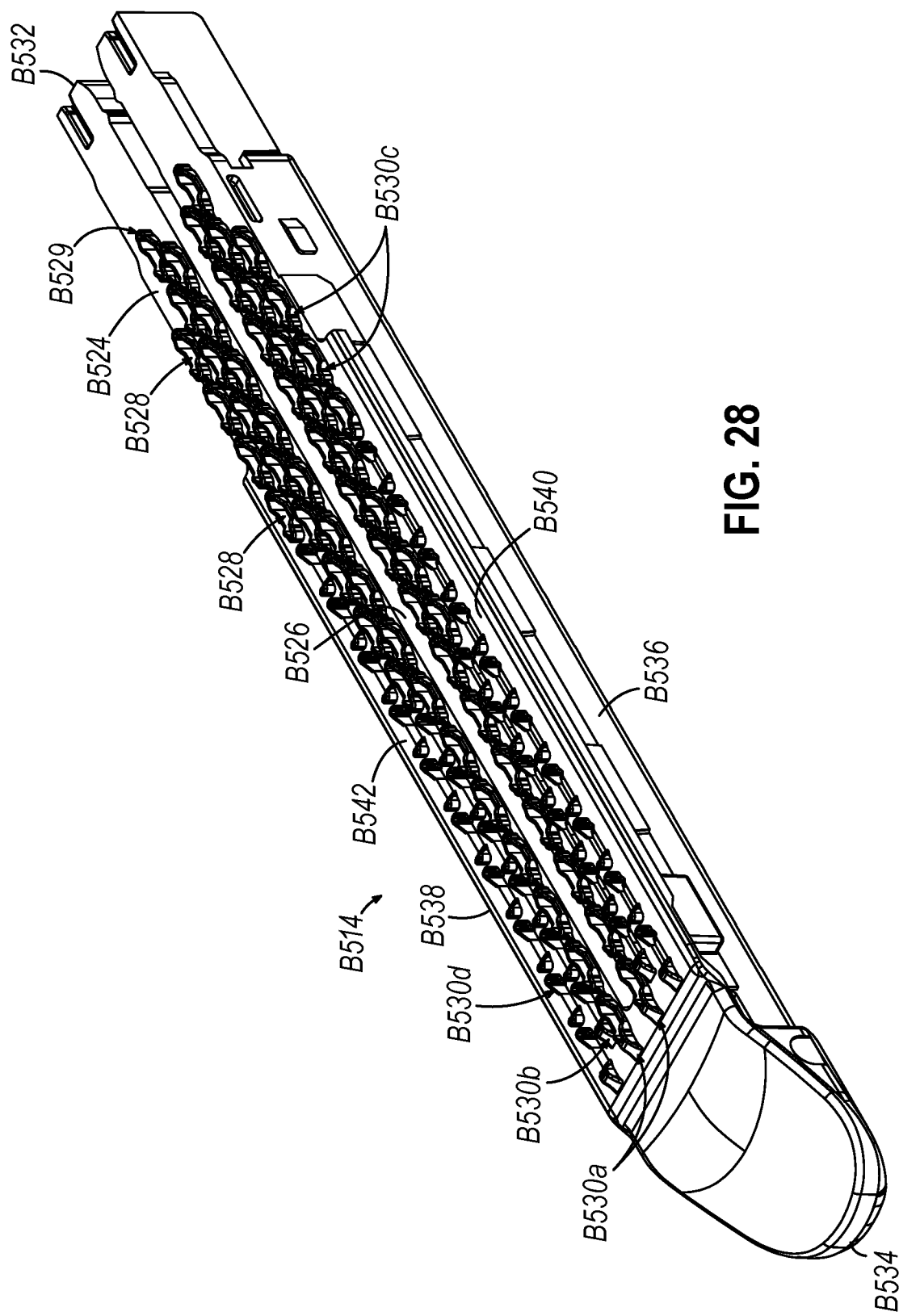
FIG. 28 depicts a perspective view of another example of a cartridge body configured to be incorporated into the staple cartridge of FIG. 7 and the end effector of FIG. 2.

FIG. 27 shows a partial sectional view of another example of a cartridge body (B414) and accompanying tray (B416) configured to be incorporated into staple cartridge (B110) of FIG. 7 for use with end effector (40) of FIG. 2. Cartridge body (B414) is similar to cartridge body (B114) described and shown above with reference to FIGS. 7-18. Engagement protrusions (B430), similar to engagement protrusions (B130a-f), include inner rows (B450), middle rows (B452), and outer rows (B454) that extend from a deck (B424). As shown in FIG. 27, maximum height (Bhep) of engagement protrusions (B430) is about 0.020 inches (0.508 millimeters), and height (Bh2d) is about 0.037 inches (0.9398 millimeters). Interconnections (B460) have a maximum height (Bhi) that is about half of maximum height (Bhep) of engagement protrusions (B430). Interconnections (B460) are similar to interconnections (B160). Deck (B424) is shown as being substantially planar.

H. Eighth Example of a Cartridge Body

FIGS. 28-32 show another example of a cartridge body (B514) configured to be incorporated into staple cartridge (B110) of FIG. 7 for use with end effector (40) of FIG. 2. Cartridge body (B512) includes a deck (B524), an elongate slot (B526) formed in deck (B524), a plurality of cartridge pockets (B528) formed in deck (B524), and a plurality of engagement protrusions (B530a-d) extending outwardly from deck (B524). Engagement protrusions (B530a-d) collectively form an array (B529). Cartridge body (B514) includes a proximal end (B532), a distal end (B534), a first lateral side (B536), and a second lateral side (B538). Second lateral side (B538) is disposed opposite first lateral side (B536). Deck (B524) is configured to compress tissue against an anvil (not shown) but similar to anvil (44). Deck (B524) is defined by cartridge body (B514) and is shown as substantially planar. Elongate slot (B526) extends along a longitudinal axis (BLA) of cartridge body (B514). Elongate slot (B526) opens upwardly through deck (B524) and terminates at a connecting portion (B531). Elongate slot (B526) is configured to slidably receive a knife therein. The knife may be a distal knife portion of a firing beam (not shown), such as distal knife portion (50) of firing beam (46).

Cartridge pockets (B528) are configured to house a plurality of staples (not shown) but similar to staples (B116). Cartridge pockets (B528) are arranged into six longitudinally extending rows. Elongate slot (B526) separates three rows on a first deck side (B540) from three additional rows on a second deck side (B542). These longitudinal rows include inner rows (B544), middle rows (B546), and outer rows (B548). While two inner rows (B544), two middle rows (B546), and two outer rows (B548) are shown, more or fewer rows are also envisioned. Inner rows (B544) are the closest cartridge pockets (B528) relative to elongate slot (B526). In other words, inner rows (B544) are positioned closer to elongate slot (B526) than middle rows (B546). Similarly, middle rows (B546) are positioned closer to elongate slot (B526) than outer rows (B548) of cartridge pockets (B528).

Engagement protrusions (B530a-d) extend from deck (B524) and are configured to grip tissue (T) or an adjunct material (e.g., a buttress) positioned thereon. As will be described below, cartridge body (B514) includes four different configurations of engagement protrusions (B530a-d). The arrangement of these engagement protrusions (B530a-d) is symmetric about elongate slot (B526). Second deck side (B542) of cartridge body (B514) is a mirror image of first deck side (B540) of cartridge body (B514). Engagement protrusions (B530a-d) are arranged into a plurality of longitudinally extending rows. These longitudinal rows include inner rows (B550), middle rows (B552), and outer rows (B554). Inner rows (B550) generally correspond with inner rows (B544) of cartridge pockets (B528). Similarly, middle rows (B552) generally correspond with middle rows (B546) of cartridge pockets (B528), and outer rows (B554) generally correspond with outer rows (B548) of cartridge pockets (B528). Inner rows (B550) are the closest engagement protrusions relative to elongate slot (B526). In other words, inner rows (B550) of engagement protrusions are positioned closer to elongate slot (B526) than middle rows (B552). Similarly, middle rows (B552) are positioned closer to elongate slot (B526) than outer rows (B554) of engagement protrusions. As shown, inner rows (B550), middle rows (B552), and outer rows (B554) each extend substantially parallel to elongate slot (B526). Each engagement protrusion (B530a-d) extends within a single row (e.g., one of inner row (B550), middle row (B552), and outer rows (B554)) and does not connect with an adjacent row. Engagement protrusions (B530a) surround a respective cartridge pocket (B528) of inner row (B544) of cartridge pockets (B528). Engagement protrusions (B530c) surround a respective cartridge pocket (B528) of inner rows (B544), middle rows (B546), and outer rows (B548) of cartridge pockets (B528).

Figure 30:
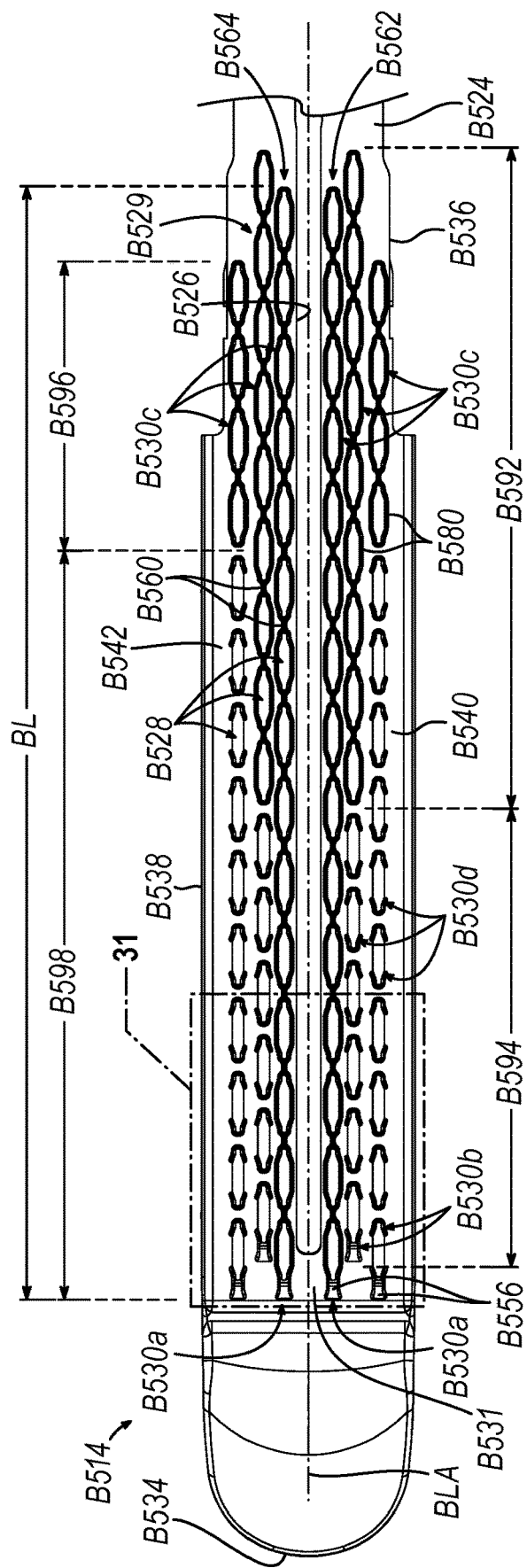
FIG. 30 depicts a partial top plan view of the partial cartridge body of FIG. 28.

FIG. 30 shows first and second continuous non-linear raised cross-sectional areas (B562, B564) forming first and second continuous non-linear paths along the entire length of cartridge pockets (B528). First and second continuous non-linear raised cross-sectional areas (B562, B564) extend from deck (B524) between adjacent engagement protrusions (B530a, B530c) joined by interconnections (B560) along the entire length of inner row (B544) of cartridge pockets (B528). First and second continuous non-linear raised cross-sectional areas (B562, B564) are configured to provide increased stiffness to inner rows (B550) of engagement protrusions (B530a-b, B530d-e) and/or increased localized clamping pressure around elongate slot (B526). Increasing the clamping pressure around elongate slot (B526) may keep tissue (T) taught and orient the tissue for cutting. For example, this may orient tissue (T) to be pierced by the knife and reduce transverse forces in tissue (T).

Middle rows (B552) include a first portion (B592) of longitudinally adjacent engagement protrusions (B530c) joined by interconnections (B560), and a second portion (B594) of adjacent engagement protrusions (B530b, B530d) that is not linked by interconnections (B560). Instead, longitudinally adjacent engagement protrusions (B530b, B530d) are spaced apart from each other. As shown, first portion (B592) of middle rows (B552) includes nine longitudinally adjacent engagement protrusions (B530d) linked by interconnections (B560). As shown, second portion (B594) of middle rows (B552) includes one engagement protrusion (B530b) and five longitudinally adjacent engagement protrusions (B530d) not linked together. In other words, first portion (B592) extends longitudinally along about 60% of middle rows (B552), and second portion (B594) extends longitudinally along about 40% of middle rows (B552). These percentages may vary, for example, first portion (B592) extends longitudinally along about 50% of middle rows (B552), and second portion (B594) extends longitudinally along about 50% of middle rows (B552).

With continued reference to FIG. 30, first portion (B596) of outer rows (B554) includes four adjacent engagement protrusions (B530d) longitudinally linked by interconnections (B560). As shown, second portion (B598) of outer rows (B554) includes ten longitudinally adjacent engagement protrusions (B530a, B530d). In other words, first portion (B592) extends longitudinally along about 29% of outer rows (B554), and second portion (B594) extends longitudinally along about 71% of outer rows (B554). These percentages may vary, for example, first portion (B592) may extend longitudinally along about 25% of outer rows (B554), and second portion (B594) extends longitudinally along about 75% of outer rows (B554). First portions (B592, B596) form continuous non-linear raised cross-sectional areas that apply greater proximal compression as compared to distal compression as the raised cross-sectional area is greater moving proximally.

Figure 29:
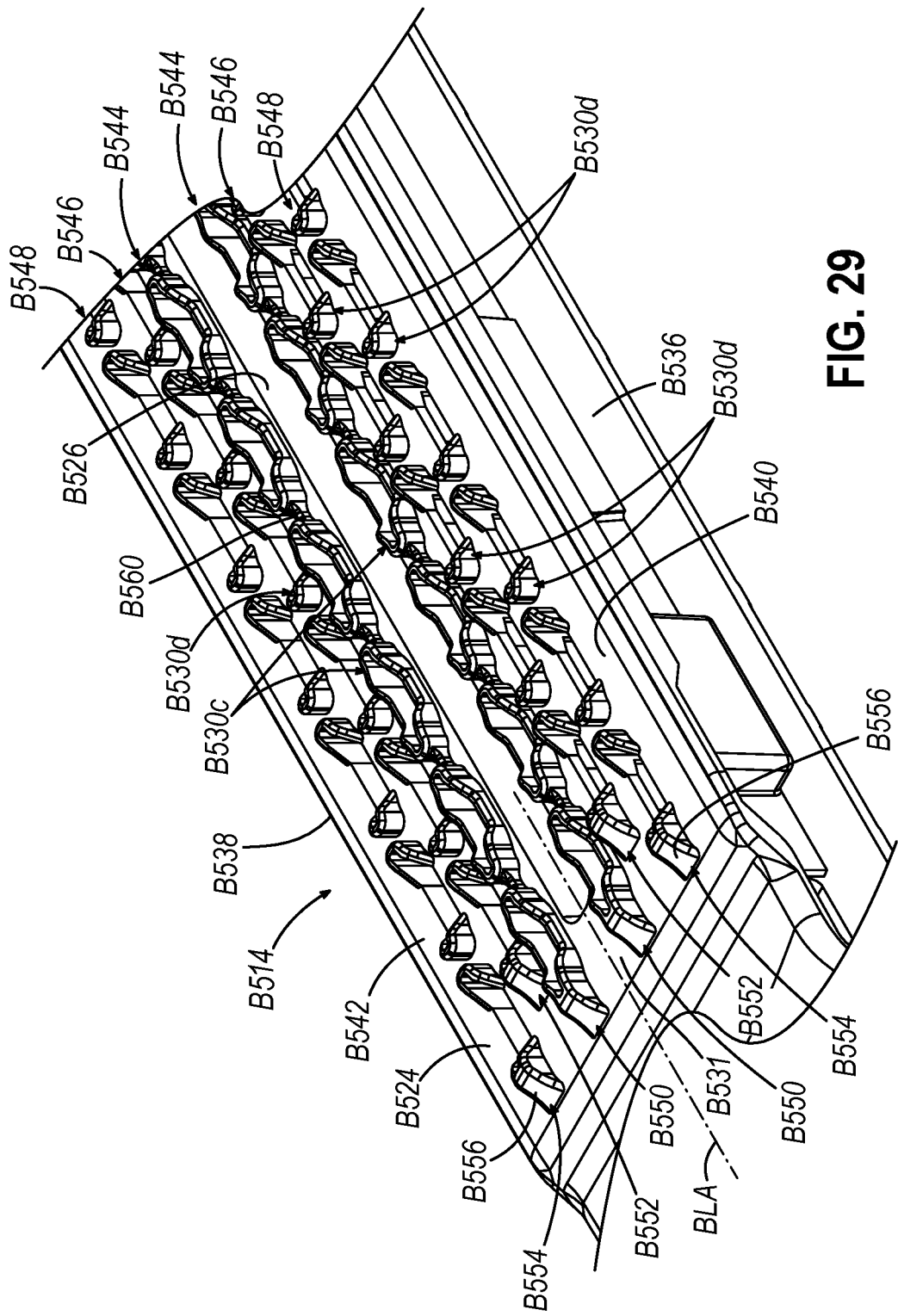
FIG. 29 depicts an enlarged perspective view of a portion of the cartridge body of FIG. 28.
Figure 31:
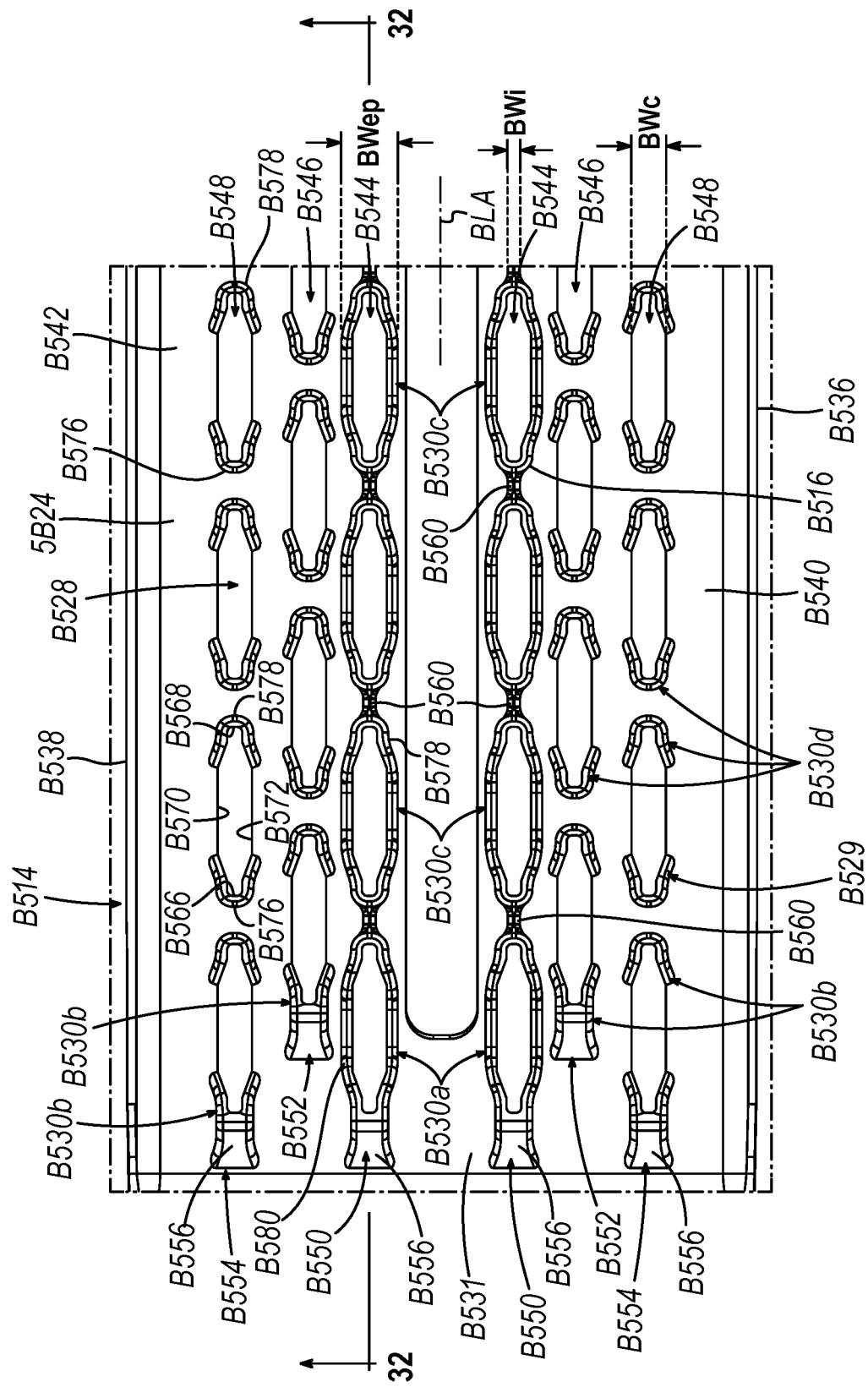
FIG. 31 depicts an enlarged top plan view of the cartridge body of FIG. 30.

As shown in FIGS. 29 and 31, engagement protrusions (B530a-b) are the distal most engagement protrusions on first and second deck sides (B540, B542). Each engagement protrusion (B530a-b) includes a distal lead-in portion (B556). As shown, longitudinally adjacent engagement protrusions (B530a, B530c) of inner rows (B550) on first and second deck sides (B540, B542) are linked together (also referred to as joined together) by interconnections (B560). Similar to cartridge pocket (B128), FIG. 31 shows cartridge pocket (B528) including a first longitudinal end (B566), a second longitudinal end (B568), a first lateral side (B570), and a second lateral side (B572). Second longitudinal end (B568) is disposed opposite first longitudinal end (B566). First and second longitudinal ends (B566, B568) are configured to guide legs (B117) of staples (B116) (see FIG. 7). First lateral side (B570) is disposed between first and second longitudinal ends (B566, B568). Second lateral side (B572) is disposed between first and second longitudinal ends (B566, B568) and opposite to first lateral side (B570). As shown, first and second lateral sides (B570, B572) of cartridge pocket (B528) extend substantially parallel to elongate slot (B526).

Engagement protrusions (B530a, B530c) include a first end portion (B576), a second end portion (B578), and a lateral portion (B580). First end portion (B576) wraps around first longitudinal end (B566) of cartridge pocket (B528). Similarly, second end portion (B578) wraps around second longitudinal end (B568) of cartridge pocket (B528). Lateral portion (B580) extends continuously between first and second end portions (B576, B578) on both of first and second lateral sides (B570, B572) of cartridge pocket (B528). Engagement protrusions (B530b, B530d) include first end portion (B576) and a second end portion (B578). Engagement protrusions (B530b, B530d) do not extend along first lateral side (B570) or second lateral side (B572) of cartridge pocket (B528) such that first lateral side (B570) and second lateral side (B572) open directly to deck (B524). Engagement protrusions (B530a, B530c) are configured to provide greater compression than engagement protrusions (B530b, B530d). Interconnections (B560) extend between second end portion (B578) of engagement protrusion (B530a) and a first end portion (B576) of an adjacent engagement protrusion (e.g., engagement protrusion (B530c)) and then between adjacent engagement protrusion (B530c) moving proximally.

Tighter tissue compression at the proximal end near elongate slot (B526) encourages the knife (e.g., distal knife portion of a firing beam (not shown), such as distal knife portion (50) of firing beam (46)) to pierce and cleanly cut tissue (T) and/or buttress (e.g., B118) at the proximal end of elongate slot (B526). Guiding of the fluid-phase of the tissue outwards both laterally and longitudinally during the clamping wait time (e.g., which may be about 15 seconds). Due to a natural tendance of fluid to flow in the path of least resistance, more fluid evacuates the tissue sooner during clamping phase to provide less fluid flow during firing. This selectively applies greater tissue pressures in localized regions and encourages fluid-flow-out of tissue (T).

As shown in FIG. 31, engagement protrusion (B530d) has a maximum width (BWp) in the direction transverse to longitudinal axis (BLA). Interconnection (B560) has a maximum width (BWi) in the direction transverse to longitudinal axis (BLA). Maximum width (BWp) of engagement protrusion (B530a-d) is greater than maximum width (BWi) of interconnection (B560). Cartridge pocket (B528) has a maximum width (BWc) defined by a distance between first and second lateral sides (B570, B572) of cartridge pocket (B528) in the direction transverse to longitudinal axis (BLA). Maximum width (BWp) of cartridge pocket (B528) is greater than maximum width (BWi) of interconnection (B560). First and second end portions (B576, B578) have a maximum width (BWep) in the direction transverse to longitudinal axis (BLA) that is greater than maximum width (BWi) of interconnection (B560).

Figure 32:
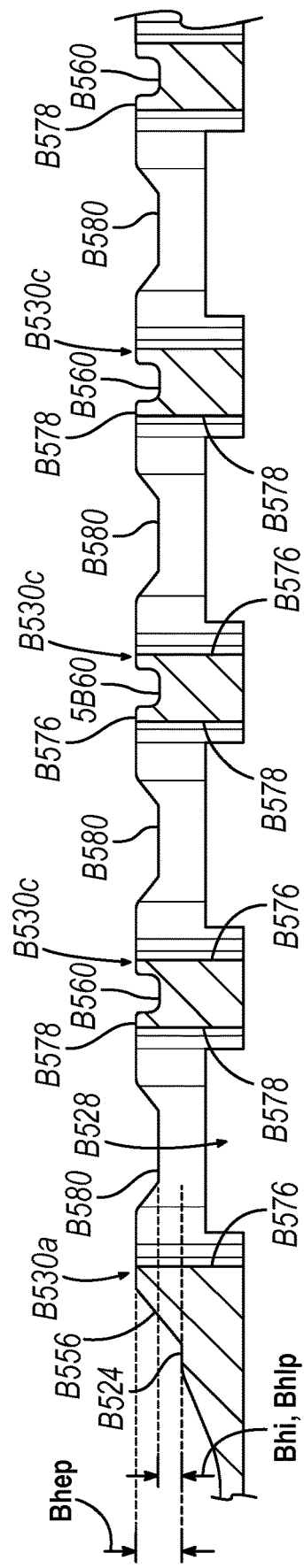
FIG. 32 depicts a partial side sectional view of the portion of the cartridge body of FIG. 31 taken along line 32-32 of FIG. 31.

As shown in FIG. 32, each engagement protrusion (B530a-d) has the same height (e.g., extends away from deck (B524) the same distance). First and second end portions (B576, B578) of engagement protrusions (B530a-d) extend from deck (B524) a maximum height (Bhep). Lateral portions (B580) of engagement protrusions (B530a, B530c) extend from deck (B524) a maximum height (Bhlp). Interconnection (B560) extends from deck (B524) a maximum height (Bhi). As shown, maximum height (Bhep) of first and second end portions (B576, B578) is greater than maximum height (Bhi) of interconnection. For example, maximum height (Bhi) of interconnections (B560) and maximum height of (Bhlp) of lateral portions (B580) may be each about half of maximum height (Bhep) of first and second end portions (B576, B578).

I. Ninth Example of a Cartridge Body

Figure 33:
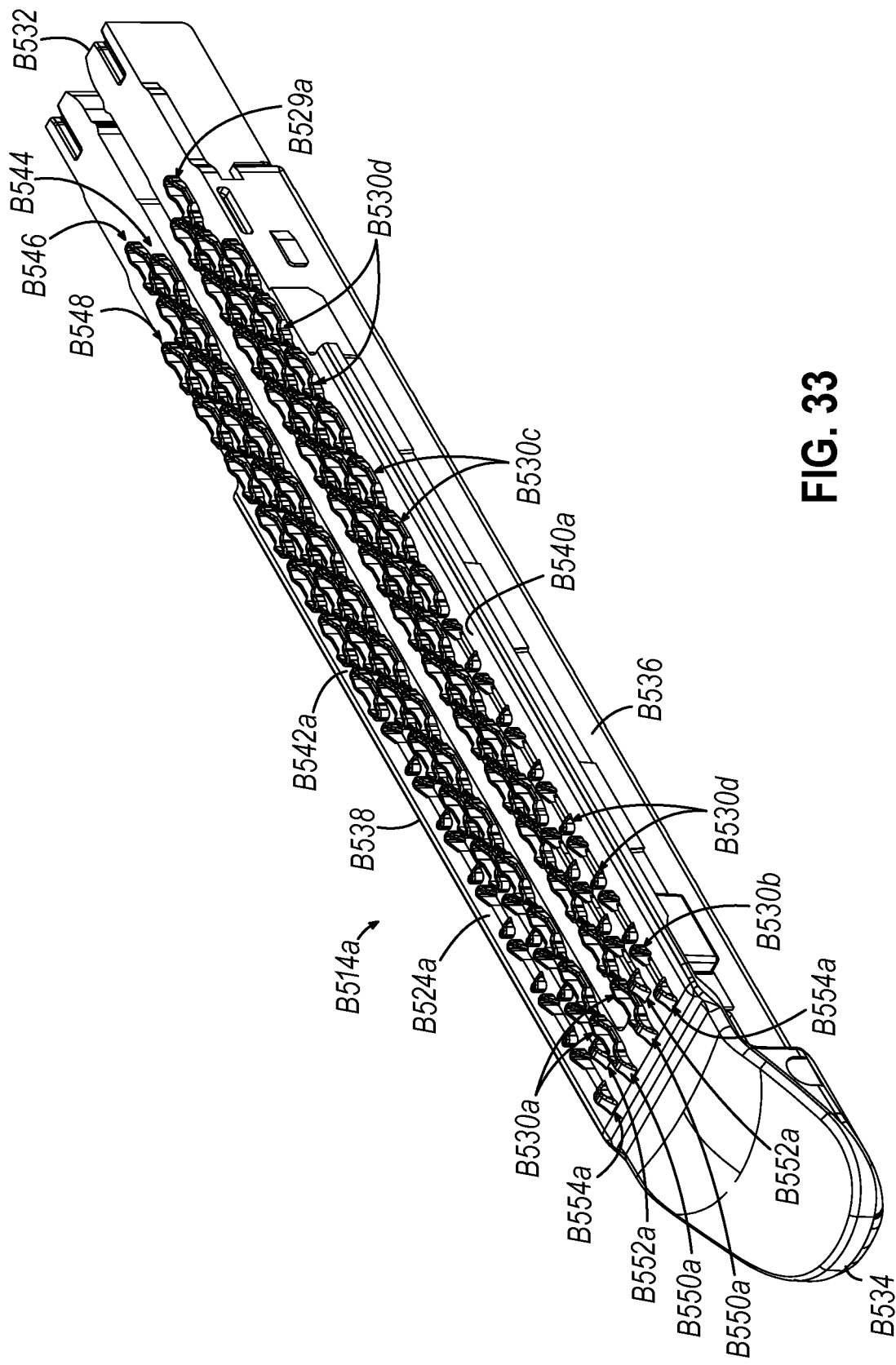
FIG. 33 depicts a perspective view of another example of a cartridge body configured to be incorporated into the staple cartridge of FIG. 7 and the end effector of FIG. 2.
Figure 34:
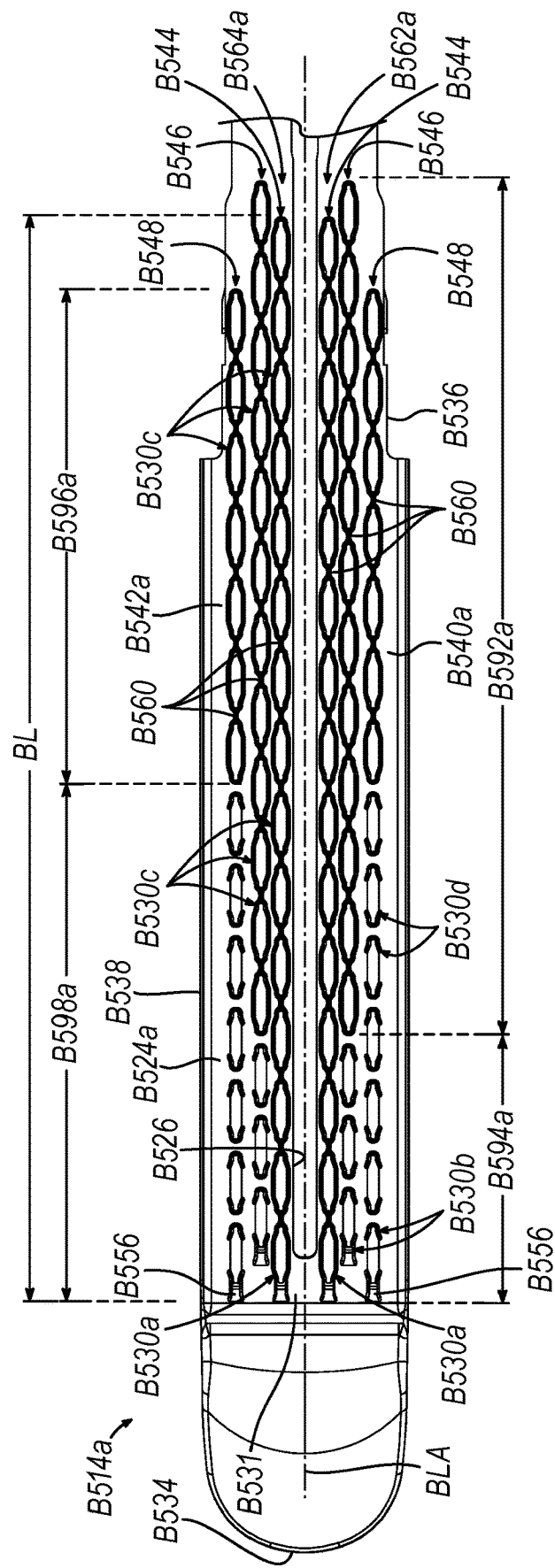
FIG. 34 depicts a partial top plan view of the cartridge body of FIG. 33.

FIGS. 33-34 show another example of a cartridge body (B514a) configured to be incorporated into staple cartridge (B110) of FIG. 7 for use with end effector (40) of FIG. 2. Similar to cartridge body (B514), cartridge body (B514a) includes a deck (B524a), an elongate slot (B526) formed in deck (B524a), a plurality of cartridge pockets (B528) formed in deck (B524a), and a plurality of engagement protrusions (B530a-d) extending outwardly from deck (B524a). Engagement protrusions (B530a-d) collectively form an array (B529a). Similar to cartridge body (B514), cartridge body (B514a) include inner rows (B544), middle rows (B546), and outer rows (B548) of cartridge pockets (B528). Similar to cartridge body (B514), cartridge body (B514a) includes engagement protrusions (B530a-d) extending from deck (B524a) that are configured to grip tissue (T) or an adjunct material (e.g., a buttress) positioned thereon. Second deck side (B542a) of cartridge body (B514a) is a mirror image of first deck side (B540a) of cartridge body (B514a). Longitudinal rows of engagement protrusions include inner rows (B550a), middle rows (B552a), and outer rows (B554a) and generally correspond to inner rows (B544), middle rows (B546), and outer rows (B548) of cartridge pockets (B528).

FIG. 34 shows first and second continuous non-linear raised cross-sectional areas (B562a, B564a) forming first and second continuous non-linear paths along an entire length (BL) of cartridge pockets (B528). Middle rows (B552a) include a first portion (B592a) of longitudinally adjacent engagement protrusions (B530b) joined by interconnections (B560), and a second portion (B594a) of adjacent engagement protrusions (B530d) that is not linked by interconnections (B560). Instead, longitudinally adjacent engagement protrusions (B530d) are spaced apart from each other. As shown, first portion (B592a) of middle rows (B552a) includes nine longitudinally adjacent engagement protrusions (B530d) linked by interconnections (B560). As shown, second portion (B594a) of middle rows (B552a) includes one engagement protrusion (B530b) and two longitudinally adjacent engagement protrusions (B530d). In other words, first portion (B592a) extends longitudinally along about 80% of middle rows (B552a), and second portion (B594a) extends longitudinally along about 20% of middle rows (B552a). These percentages may vary, for example, first portion (B592a) may extend longitudinally along about 75% of middle rows (B552a), and second portion (B594a) extends longitudinally along about 25% of middle rows (B552a).

With continued reference to FIG. 34, first portion (B596a) of outer rows (B554a) includes seven adjacent engagement protrusions (B530d) longitudinally linked by interconnections (B560). As shown, second portion (B598a) of outer rows (B554a) includes one engagement protrusion (B530b) and six longitudinally adjacent engagement protrusions (B530d). In other words, first and second portions (B592a, B596a) each extend longitudinally along about 50% of outer rows (B554a). First portions (B592a, B596a) form continuous non-linear raised cross-sectional areas. Increasing the clamping pressure around elongate slot (B526) may keep the tissue taught and orient the tissue for cutting. For example, this may orient the tissue to be pierced by the knife and reduce transverse forces in the tissue. Cartridge body (B514a) may provide greater compression than cartridge body (B514) since cartridge body (B514a) has a greater raised cross-sectional area.

J. Tenth Example of a Cartridge Body

Figure 35:
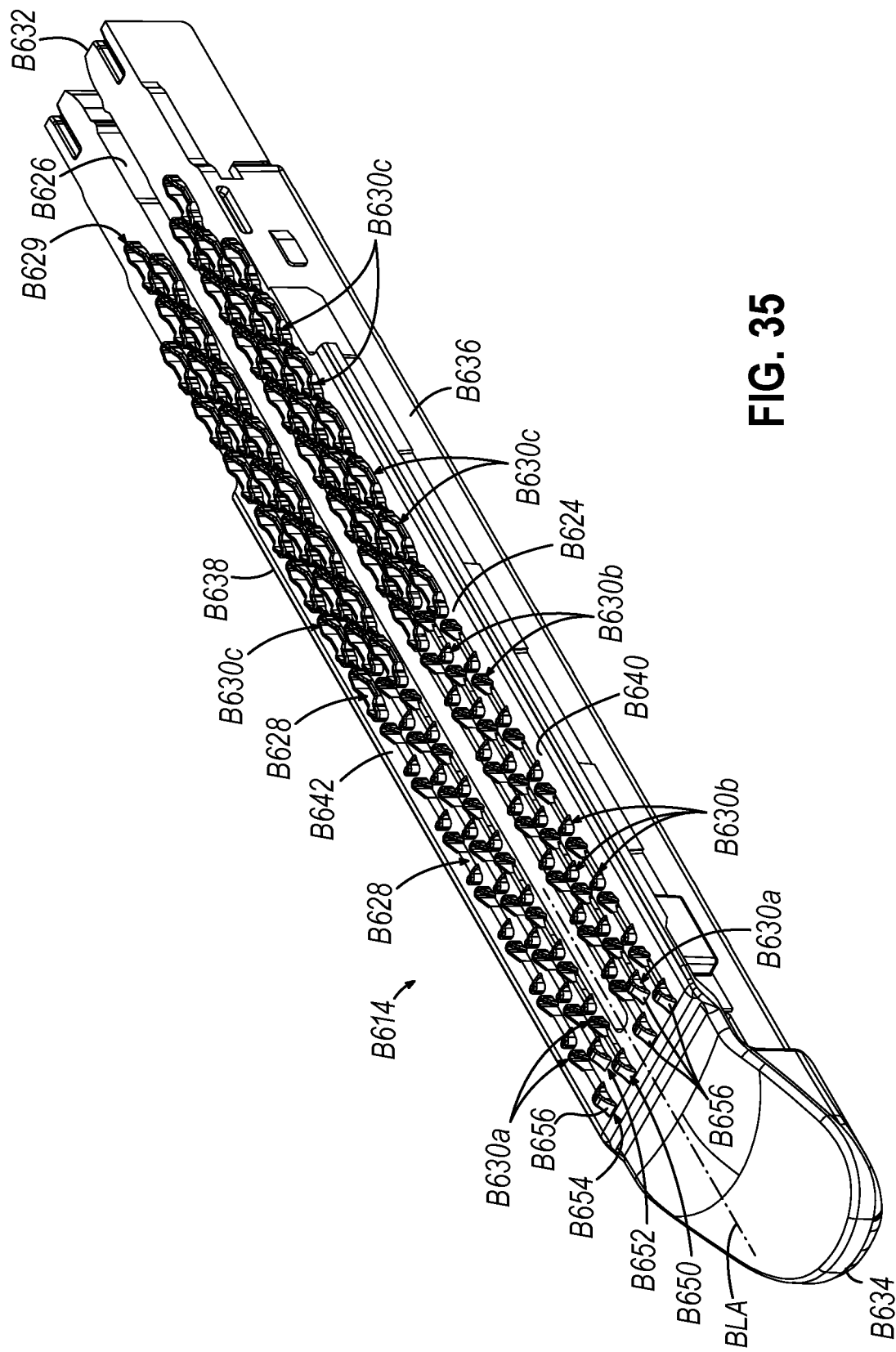
FIG. 35 depicts a perspective view of another example of a cartridge body configured to be incorporated into the staple cartridge of FIG. 7 and the end effector of FIG. 2.
Figure 36:
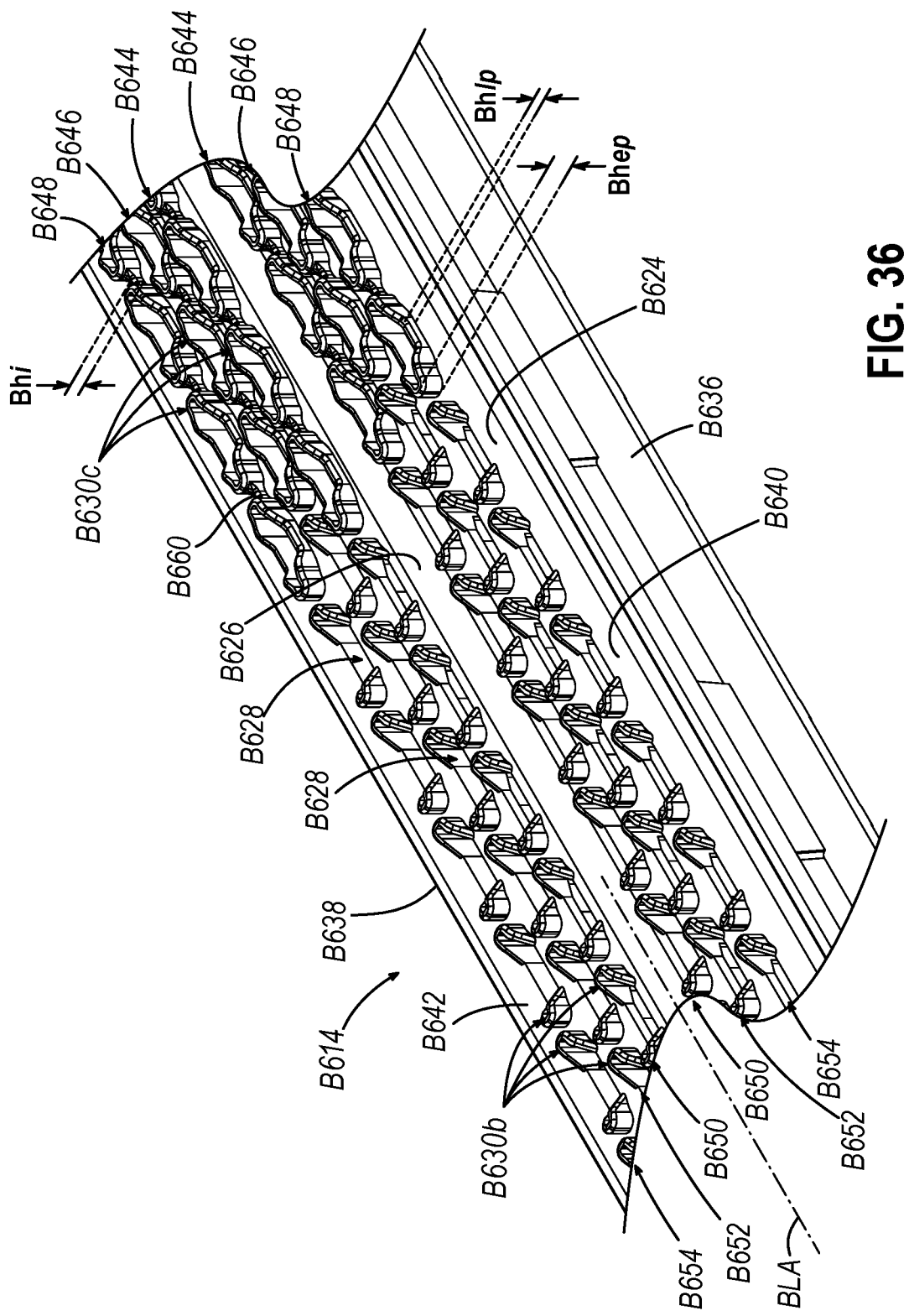
FIG. 36 depicts an enlarged perspective view of the cartridge body of FIG. 35.
Figure 37:
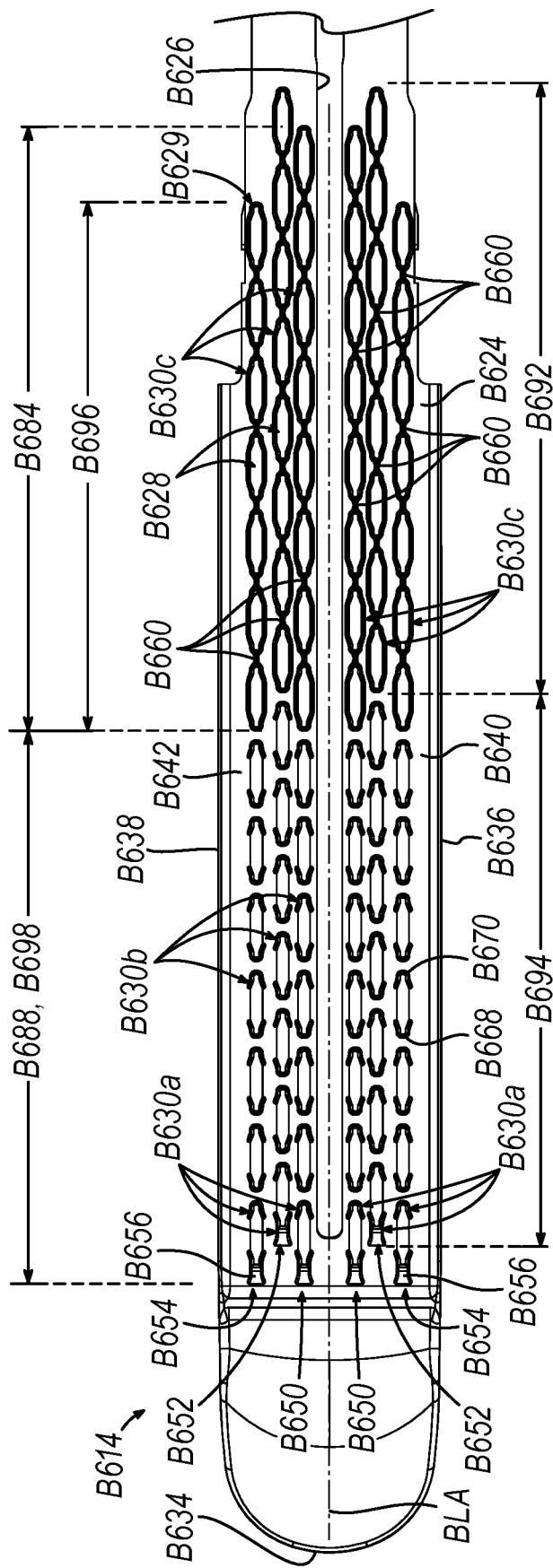
FIG. 37 depicts a partial top plan view of the cartridge body of FIG. 35.

FIGS. 35-37 show another example of a cartridge body (B614) configured to be incorporated into staple cartridge (B110) of FIG. 7 for use with end effector (40) of FIG. 2. Cartridge body (B612) includes a deck (B624), an elongate slot (B626) formed in deck (B624), a plurality of cartridge pockets (B628) formed in deck (B624), and a plurality of engagement protrusions (B630a-c) extending outwardly from deck (B624). Engagement protrusions (B630a-c) collectively form an array (B629). Cartridge body (B614) includes a proximal end (B632), a distal end (B634), a first lateral side (B636), and a second lateral side (B638). Second lateral side (B638) is disposed opposite first lateral side (B636). Deck (B624) is configured to compress tissue against an anvil (not shown) but similar to anvil (44). Deck (B624) is defined by cartridge body (B614) and is shown as upwardly facing and substantially planar. Elongate slot (B626) extends along a longitudinal axis (BLA) of cartridge body (B614). Elongate slot (B626) opens upwardly through deck (B624) and terminates at a connecting portion (B633). Elongate slot (B626) is configured to slidably receive a knife therein. The knife may be a distal knife portion of a firing beam (not shown), such as distal knife portion (60) of firing beam (46).

Cartridge pockets (B628) are configured to house a plurality of staples (not shown) but similar to staples (B116) and staple drivers (not shown) but similar to staple drivers (B118). Cartridge pockets (B628) are arranged into six longitudinally extending rows. Elongate slot (B626) separates three rows positioned on a first deck side (B640) from three additional rows are positioned a second deck side (B642). These longitudinal rows include inner rows (B644), middle rows (B646), and outer rows (B648). While two inner rows (B644), two middle rows (B646), and two outer rows (B648) are shown, more or fewer rows are also envisioned. Inner rows (B644) are the closest cartridge pockets (B628) relative to elongate slot (B626). In other words, inner rows (B644) are positioned closer to elongate slot (B626) than middle rows (B646), and middle rows (B646) are positioned closer to elongate slot (B626) than outer rows (B648) of cartridge pockets (B628).

Engagement protrusions (B630a-c) extend from deck (B624) and are configured to grip tissue (T) or an adjunct material (e.g., a buttress) positioned thereon. As will be described below, cartridge body (B614) includes three different configurations of engagement protrusions (B630a-c). The arrangement of these engagement protrusions (B630a-c) is symmetric about elongate slot (B626). Second deck side (B642) of cartridge body (B614) is a mirror image of first deck side (B640). Engagement protrusions (B630a-c) are arranged into a plurality of longitudinally extending rows. These longitudinal rows include inner rows (B650), middle rows (B652), and outer rows (B654). Inner rows (B650) generally correspond with inner rows (B644) of cartridge pockets (B628). Similarly, middle rows (B652) generally correspond with middle rows (B646) of cartridge pockets (B628). Similarly, outer rows (B654) generally correspond with outer rows (B648) of cartridge pockets (B628).

Inner rows (B650) are the closest engagement protrusions relative to elongate slot (B626). In other words, inner rows (B650) of engagement protrusions are positioned closer to elongate slot (B626) than middle rows (B652). Similarly, middle rows (B652) are positioned closer to elongate slot (B626) than outer rows (B654) of engagement protrusions. As shown, inner rows (B650), middle rows (B652), and outer rows (B654) each extend substantially parallel to elongate slot (B626). Each engagement protrusion (B630a-c) extends within a single row (e.g., one of inner row (B650), middle row (B652), and outer rows (B654)) and does not connect with an adjacent row. Each engagement protrusions (B630a) partially surrounds a respective cartridge pocket (B628) of inner row (B644) of cartridge pockets (B628). Each engagement protrusion (B630c) completely surrounds a respective cartridge pocket (B628) of inner rows (B644), middle rows (B646), and outer rows (B648) of cartridge pockets (B628). As shown in FIGS. 35 and 37, engagement protrusions (B630a) are the distal most engagement protrusions on first and second deck sides (B640, B642). Each engagement protrusion (B630a) includes a distal lead-in portion (B656).

As shown in FIG. 37, inner rows (B650) include a first portion (B684) of longitudinally adjacent engagement protrusions (B630c) joined by interconnections (B660), and a second portion (B688) of adjacent engagement protrusions (B630a-b) that are not linked by interconnections (B660). Instead, longitudinally adjacent engagement protrusions (B630a-b) are spaced apart from each other. As shown, first portion (B684) of inner rows (B650) includes eight longitudinally adjacent engagement protrusions (B630c) linked by interconnections (B660). As shown, second portion (B688) of middle rows (B652) includes one engagement protrusion (B630a) and six longitudinally adjacent engagement protrusions (B630b) not linked together. In other words, first portion (B684) extends longitudinally along about 53% of middle rows (B652), and second portion (B688) extends longitudinally along about 47% middle rows (B652). First portion (B684) is positioned entirely proximal to second portion (B688).

Middle rows (B652) include a first portion (B692) of longitudinally adjacent engagement protrusions (B630b) joined by interconnections (B660), and a second portion (B694) of adjacent engagement protrusions (B630a-b) that are not linked by interconnections (B660). Instead, longitudinally adjacent engagement protrusions (B630a-b) are spaced apart from each other. As shown, first portion (B692) of middle rows (B652) includes eight longitudinally adjacent engagement protrusions (B630d) linked by interconnections (B660). Second portion (B694) of middle rows (B652) includes one engagement protrusions (B630a) and six longitudinally adjacent engagement protrusions (B630d) not linked together. In other words, first portion (B692) extends longitudinally along about 53% of middle rows (B652), and second portion (B694) extends longitudinally along about 47% middle rows (B652). These percentages may vary. First portion (B692) is positioned entirely proximal to second portion (B694).

With continued reference to FIG. 37, first portion (B696) of outer rows (B654) includes four adjacent engagement protrusions (B630d) longitudinally linked by interconnections (B660). As shown, second portion (B698) of outer rows (B654) includes ten longitudinally adjacent engagement protrusions (B630a, B630d). In other words, first and second portions (B692, B696) each extend longitudinally along about 50% of outer rows (B654). First portions (B684, B692, B696) form continuous non-linear raised cross-sectional areas. Engagement protrusions (B630a-d) and interconnections (B660) selectively apply greater compression along only a predetermined longitudinal length of cartridge body (B614). First portion (B696) is positioned entirely proximal to second portion (B698). Engagement protrusions (B630a-d) and interconnections (B660) apply greater compression during initial knife travel and staples (e.g., staples (B116) located adjacent proximal end (B632). This may provide greater clamping pressure adjacent the proximal region where the knife starts cutting tissue (T).

Figure 38:
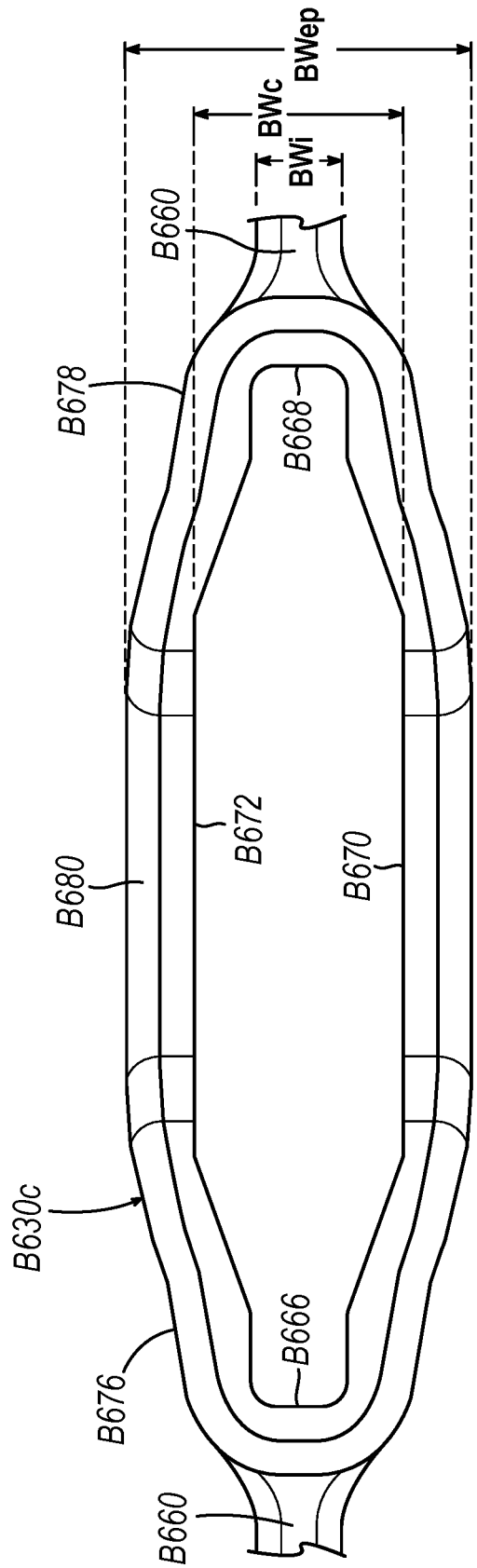
FIG. 38 depicts an enlarged top view of an engagement protrusion and accompanying interconnections completely surrounding a cartridge pocket of the cartridge body of FIG. 37.

As shown in FIG. 38 and as similar to cartridge pocket (B128), cartridge pocket (B628) includes a first longitudinal end (B666), a second longitudinal end (B668), a first lateral side (B670), and a second lateral side (B672). Second longitudinal end (B668) is disposed opposite first longitudinal end (B666). First and second longitudinal ends (B666, B668) are configured to guide legs (B117) of staples (B116) (see FIG. 7). First lateral side (B670) is disposed between first and second longitudinal ends (B666, B668). Second lateral side (B672) is disposed between first and second longitudinal ends (B666, B668) and opposite to first lateral side (B670). As shown, first and second lateral sides (B670, B672) of cartridge pocket (B628) extend substantially parallel to elongate slot (B626). Engagement protrusion (B630c) includes a first end portion (B676), a second end portion (B678), and a lateral portion (B680). First end portion (B676) wraps around first longitudinal end (B666) of cartridge pocket (B628). Similarly, second end portion (B678) wraps around second longitudinal end (B668) of cartridge pocket (B628). Lateral portion (B680) extends longitudinally between first and second end portions (B676, B678) on both of first and second lateral sides (B670, B672) of cartridge pocket (B628). Lateral portion (B680) extends continuously between first and second end portions (B676, B678) of engagement protrusion (B630c). Engagement protrusions (B630c) are configured to provide greater compression than engagement protrusions (B630a-b). Interconnections (B660) extend between second end portion (B678) of engagement protrusion (B630a) and first end portion (B676) of adjacent engagement protrusion (B630c). Similar to engagement protrusion (B630c), engagement protrusions (B630a-b) include a first end portion (B676) and a second end portion (B678). Engagement protrusions (B630a-b) do not extend along first lateral side (B670) or second lateral side (B672) of cartridge pocket (B628) such that first lateral side (B670) and second lateral side (B672) open directly to deck (B624).

As shown in FIG. 36, each engagement protrusion (B630a-c) has the same height (e.g., extends away from deck (B624) the same distance). First and second end portions (B676, B678) of engagement protrusions (B630d-e) extend from deck (B624) a maximum height (Bhep). Lateral portions (B680) of engagement protrusions (B630c) extend from deck (B624) a maximum height (Bhlp). Interconnections (B660) extend from deck (B624) a maximum height (Bhi). As shown, maximum height (Bhep) of first and second end portions (B676, B678) is greater than maximum height (Bhi) of interconnections (B660). For example, maximum height (Bhi) of interconnections (B660) and maximum height of (Bhlp) of lateral portions (B680) may be each about half of maximum height (Bhep) of first and second end portions (B676, B678).

As shown in FIG. 38, engagement protrusions (B630a-c) have a maximum width (BWp) in the direction transverse to longitudinal axis (BLA). Interconnection (B660) has a maximum width (BWi) in the direction transverse to longitudinal axis (BLA). Maximum width (BWp) of engagement protrusion (B630d) is greater than maximum width (BWi) of interconnection (B660). Cartridge pocket (B628) has a maximum width (BWc) defined by a distance between first and second lateral sides (B670, B672) of cartridge pocket (B628) in the direction transverse to longitudinal axis (BLA). Maximum width (BWc) of cartridge pocket (B628) is greater than maximum width (BWi) of interconnection (B660). First and second end portions (B676, B678) have a maximum width (BWep) in the direction transverse to longitudinal axis (BLA) that is greater than maximum width (BWi) of interconnection (B660).

K. Eleventh Example of a Cartridge Body

Figure 39:
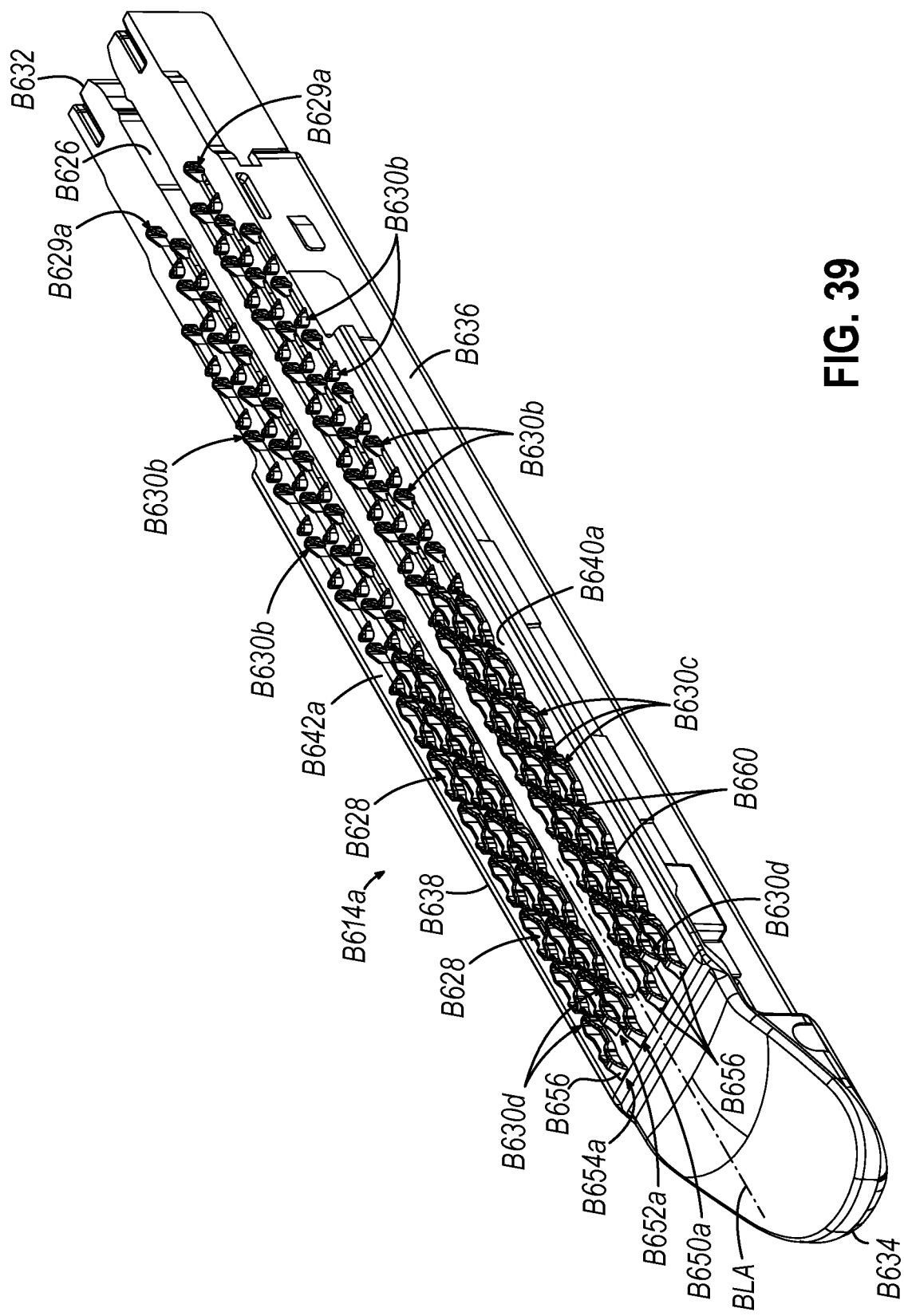
FIG. 39 depicts a perspective view of another example of a cartridge body configured to be incorporated into the staple cartridge of FIG. 7 and the end effector of FIG. 2.
Figure 40:
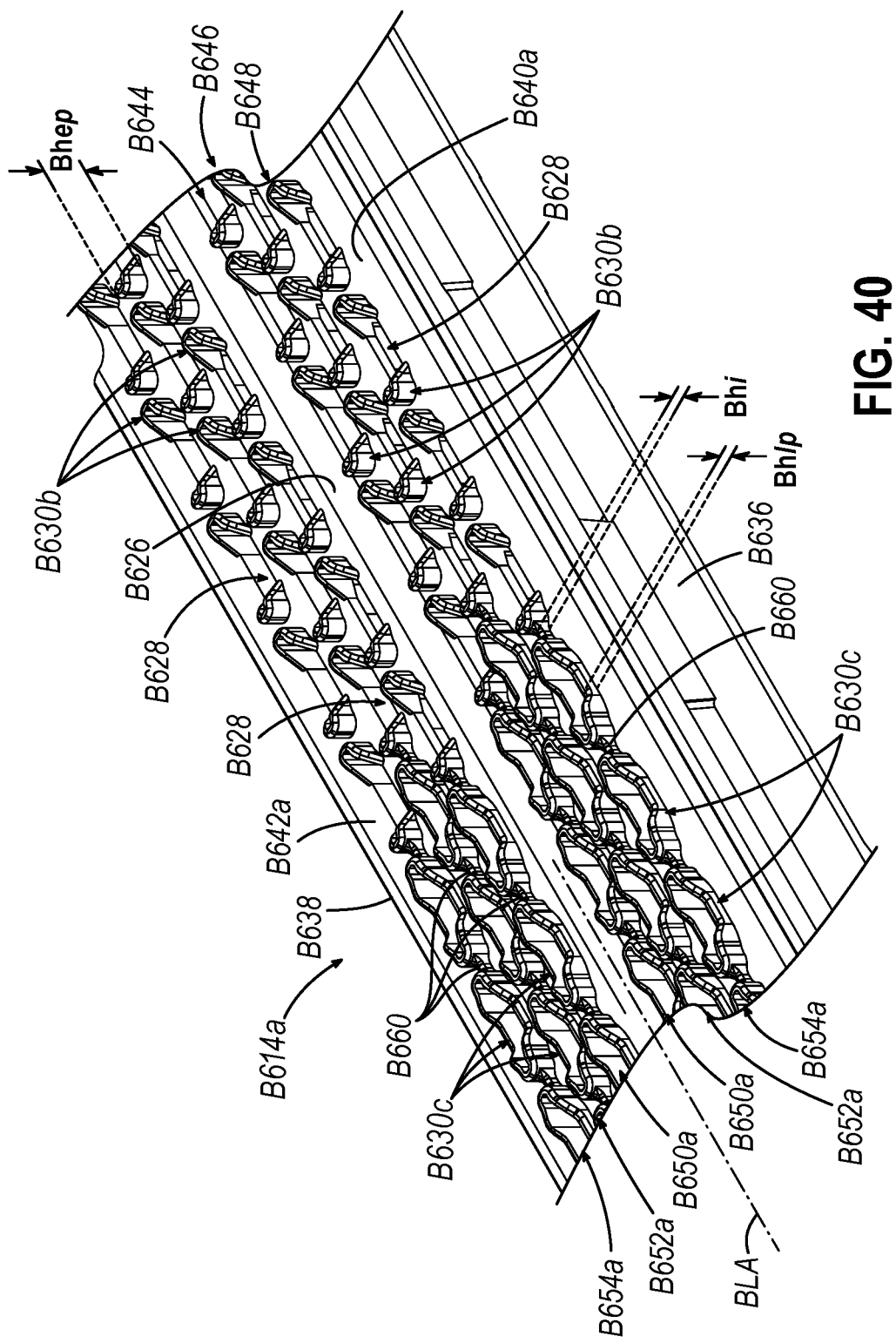
FIG. 40 depicts an enlarged perspective view of a portion of the cartridge body of FIG. 39.
Figure 41:
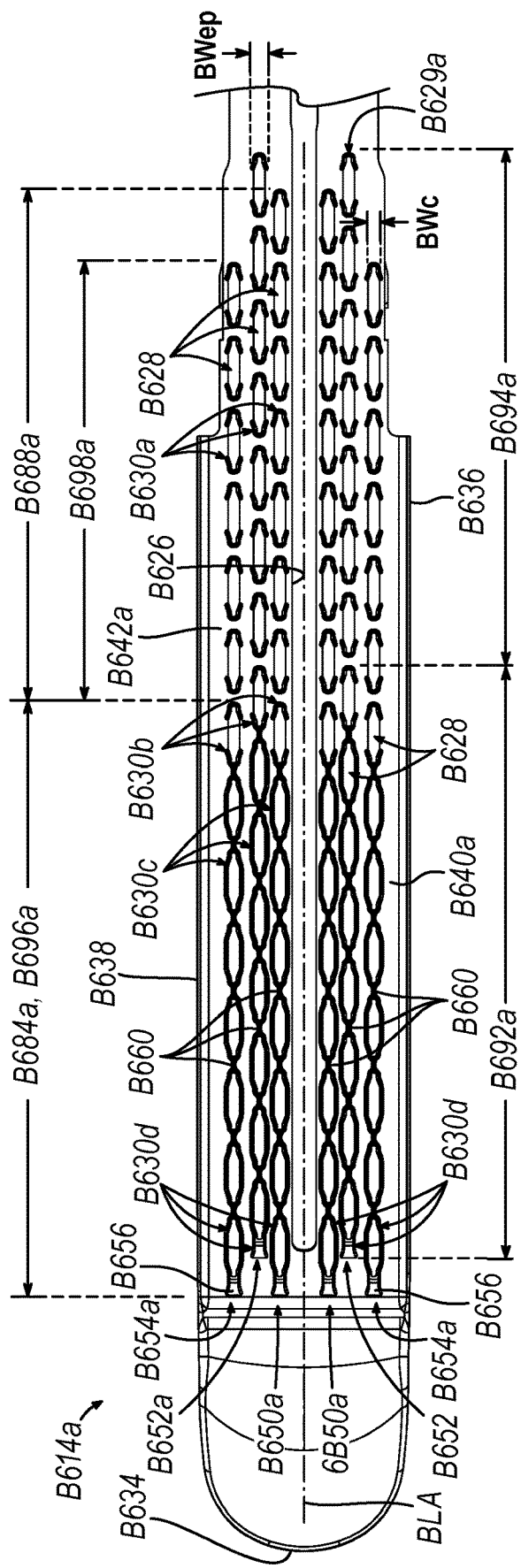
FIG. 41 depicts a top plan view of the cartridge body of FIG. 38.

FIGS. 39-41 show another example of a cartridge body (B614a) configured to be incorporated into staple cartridge (B110) of FIG. 7 for use with end effector (40) of FIG. 2. Similar to cartridge body (B614), cartridge body (B614a) includes a deck (B624a), an elongate slot (B626) formed in deck (B624a), a plurality of cartridge pockets (B628) formed in deck (B624a), and a plurality of engagement protrusions (B630b-d) extending outwardly from deck (B624a). Engagement protrusions (B630a-c) collectively form an array (B629a). Each cartridge pocket (B628) is configured to slidably house an unformed staple (not shown) but similar to staple (B116) and a respective staple driver (not shown) but similar to staple driver (B118). Similar to cartridge body (B614), cartridge body (B614a) include inner rows (B644), middle rows (B646), and outer rows (B648) of cartridge pockets (B628). Similar to cartridge body (B614), cartridge body (B614a) includes engagement protrusions (B630a-d) extending from deck (B624a) that are configured to grip tissue (T) or an adjunct material (e.g., a buttress) positioned thereon. Second deck side (B642a) is a mirror image of first deck side (B640a). Longitudinal rows of engagement protrusions include inner rows (B650a), middle rows (B652a), and outer rows (B654a) that generally correspond to inner rows (B644), middle rows (B646), and outer rows (B648), respectively.

Inner rows (B650a) include a first portion (B684a) of longitudinally adjacent engagement protrusions (B630b-d) joined by interconnections (B660), and a second portion (B688a) of adjacent engagement protrusions (B630b) that are not linked by interconnections (B660). Instead, longitudinally adjacent engagement protrusions (B630b) of second portion (B688a) are spaced apart from each other. Moving proximally, first portion (B684a) of inner rows (B650a) includes one engagement protrusions (B630d), six longitudinally adjacent engagement protrusions (B630c), and one engagement protrusion (B630b) linked by interconnections (B660). As shown, second portion (B688a) of inner rows (B650a) includes six longitudinally adjacent engagement protrusions (B630b) not linked together. In other words, first portion (B684a) extends longitudinally along about 53% of inner rows (B650a), and second portion (B688a) extends longitudinally along about 47% of inner rows (B650a). Unlike first and second portions (B684, B688) of FIGS. 35-37, first portion (B684a) is positioned entirely distal to second portion (B688a).

Middle rows (B652a) include a first portion (B692a) of longitudinally adjacent engagement protrusions (B630b-d) joined by interconnections (B660), and a second portion (B694a) of adjacent engagement protrusions (B630b) that are not linked by interconnections (B660). Instead, longitudinally adjacent engagement protrusions (B630b) of second portion (B694a) are spaced apart from each other. Moving proximally, first portion (B692a) of middle rows (B652a) includes one engagement protrusions (B630d), six longitudinally adjacent engagement protrusions (B630c), and one engagement protrusion (B630b) linked by interconnections (B660). As shown, second portion (B688a) of middle rows (B652a) includes seven longitudinally adjacent engagement protrusions (B630b) not linked together. In other words, first portion (B692a) extends longitudinally along about 53% of middle rows (B652a), and second portion (B694a) extends longitudinally along about 47% of middle rows (B652a). Unlike first and second portions (B692, B694) of FIGS. 35-37, first portion (B692a) is positioned entirely distal to second portion (B694a).

Outer rows (B654a) include a first portion (B696a) of longitudinally adjacent engagement protrusions (B630b-d) joined by interconnections (B660), and a second portion (B698a) of adjacent engagement protrusions (B630b) that are not linked by interconnections (B660). Instead, longitudinally adjacent engagement protrusions (B630b) of second portion (B698a) are spaced apart from each other. Moving proximally, first portion (B696a) of outer rows (B654a) includes one engagement protrusions (B630d), six longitudinally adjacent engagement protrusions (B630c), and one engagement protrusion (B630b) linked by interconnections (B660). As shown, second portion (B698a) of outer rows (B654a) includes seven longitudinally adjacent engagement protrusions (B630b) not linked together. In other words, first portion (B696a) extends longitudinally along about 57% of outer rows (B654a), and second portion (B698a) extends longitudinally along about 43% of outer rows (B654a). Unlike first and second portions (B696, B698) of FIGS. 35-37, first portion (B692a) is positioned entirely distal to second portion (B694a). First portions (B684, B692, B696) each form continuous non-linear raised cross-sectional areas, except along engagement protrusions (B630b) that do not include a lateral portion. First portions (B684a, B692a, B696a) selectively apply greater compression along a distal portion as compared to second portions (B686a, B694a, B698a) along a proximal portion. Similar to cartridge body (B614), maximum height (Bhep) of first and second end portions (B676, B678) is greater than .maximum height (Bhi) of interconnections (B660) and maximum height of (Bhlp) of lateral portions (B680). Similar to cartridge body (B614), first and second end portions (B676, B678) have a maximum width (BWep) that is greater than maximum width (BWc) of cartridge pocket (B628).

L. Twelfth Example of a Cartridge Body

FIGS. 42-45C show another example of a cartridge body (B80100) configured to be incorporated into stapler cartridge (B110) of FIG. 7 for use with end effector (40) of FIG. 2. Cartridge body (B80100) comprises a proximal end (B80102) and a distal end (B80104), a deck surface (B80106) that extends between proximal end (B80102) and distal end (B80104) and is configured to oppose an anvil of the end effector. The cartridge body further comprises a base surface (B80108) that is opposite the deck surface (B80106). A longitudinal slot (B80110) is defined in cartridge body (B80100). Longitudinal slot (B80110) extends from the proximal end (B80102) toward the distal end (B80104) and is sized to receive a sled driver, or firing actuator, to eject staples out of cartridge body (B80100) during a staple firing stroke. Various aspects of staple cartridges are described in greater detail in U.S. Pat. No. 9,844,369, the disclosure of which is herein incorporated by reference in its entirety.

Figure 42:
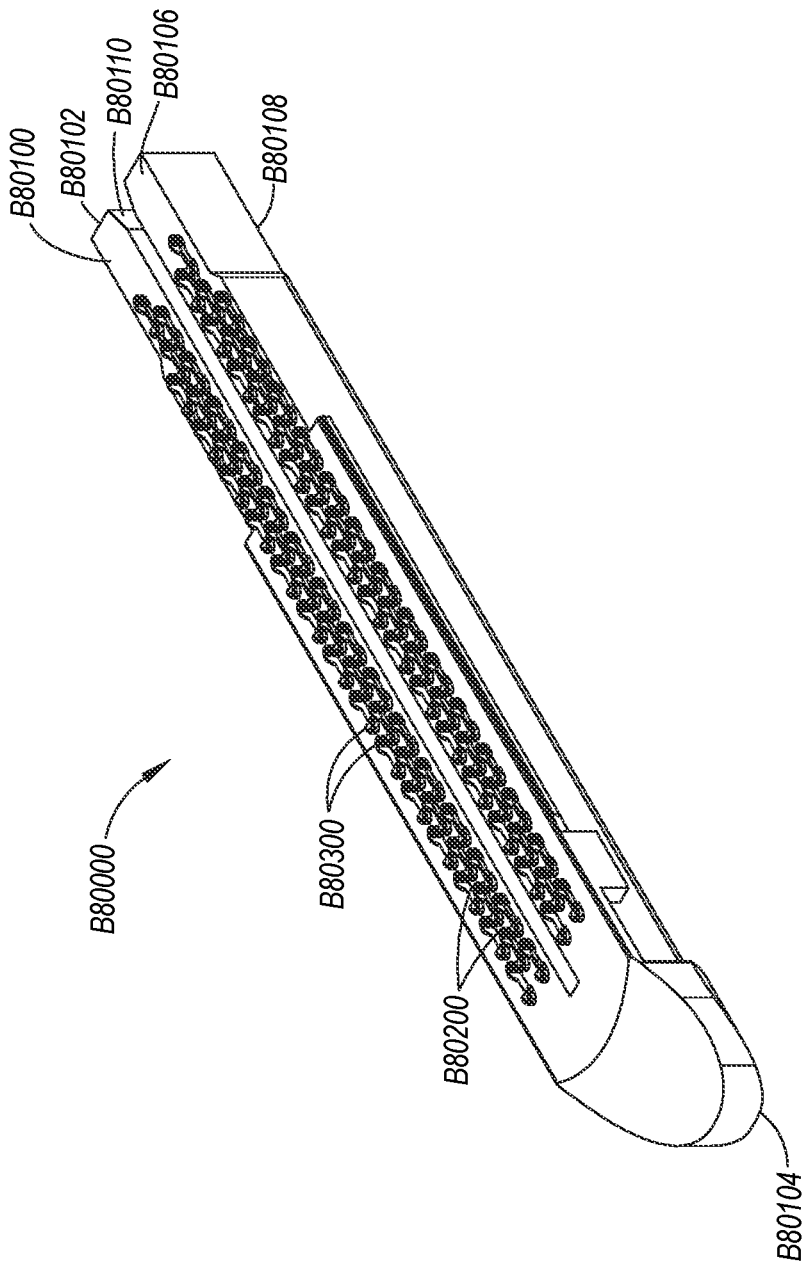
FIG. 42 depicts a perspective view of another example of a cartridge body configured to be incorporated into the staple cartridge of FIG. 7 and the end effector of FIG. 2.

Staples are removably stored in staple cavities (B80200) (also referred to as cartridge pockets) defined in the cartridge body (B80100). As illustrated in FIG. 42, six longitudinal rows of staple cavities are defined in the cartridge body (B80100); however, any suitable number of staple cavity rows and/or staple cavities is envisioned and can be selected based on the particular surgical procedure, for example. Out of the six longitudinal rows of staple cavities shown in FIG. 42, three longitudinal rows are defined on each side of the longitudinal slot (B80110).

As can be seen in FIG. 42, projections (B80300) (also referred to as engagement protrusions) are integrated, or integrally-formed, with the cartridge body (B80100) and extend away from the deck surface (B80106). Multiple, discrete projections (B80300) surround at least a portion of the staple cavities (B80200) defined in the cartridge body (B80100). As described in greater detail herein, various features of the projections (B80300) including projection width, height, and/or overall geometry (sometimes referred to herein as "projection configuration") can be modified to maximize a gripping strength of staple cartridge (B110) while also minimizing any damage to an adjacent article, such as patient tissue or an adjunct material. A geometry of proximal projections may comprise a sharp tissue-facing interface to prevent the adjacent article from unintentional displacement while a geometry of distal projections may comprise a smooth tissue-facing interface to prevent damage to the adjacent article as the adjacent article is positioned adjacent the cartridge deck.

Projections (B80300) allow for numerous benefits including gripping an adjacently positioned article, such as an adjunct layer or patient tissue, against the deck surface (B80106). The placement of the projections (B80300) around at least a portion of the staple cavities (B80200) secures the adjacent article in place, or otherwise prevents unwanted movement of the adjacent article, as staples are ejected from the cavities and/or the adjacent article is severed during a staple firing and tissue cutting stroke. An additional benefit realized by the placement of the projections (B80300) around at least a portion of the staple cavities includes guidance for the staples as the staples are fired, or otherwise ejected, from the cartridge body (B80100) and formed against an anvil during a staple firing stroke. The support provided by the projections (B80300) may also help to maintain a desired, upright orientation of the staples as the staples exit the staple cavities (B80200) during the firing stroke.

Maintenance of the adjacent article or adjunct material in its desired position by the staple cavities (B80200) is desirable to achieve a uniform staple line. In instances where the adjacent article slips or otherwise moves out of its desired position alongside the staple cavities (B80200), the staples ejected out of the staple cavities (B80200) may fail to encounter the adjacent article and/or encounter a thicker adjacent article as the staples are formed. Such inconsistencies in the adjacent article can result in a non-uniform staple line having staples formed to unwanted different heights which can lead to complications such as a non-sealed tissue cut line and/or tissue trauma, for example.

Given the universal desire for optimizing the integrity retention of the adjacent article, for example, the degree of gripping strength across the deck surface need not be uniform. As such, these considerations must be weighed against one another in designing a topography of the cartridge deck. For example, portions of an adjacent article positioned nearest the longitudinal slot of the staple cartridge are subject to greater displacement forces as the sled driver, or firing actuator, is longitudinally traversed through the staple cartridge during a staple firing stroke. In such instances, to avoid having the same intensity of gripping strength across the entire deck surface, and thus, risking the integrity of the entire adjacent article, the deck surface can provide a targeted, greater degree of gripping functionality alongside the longitudinal slot. In such instances, other lateral portions of the deck surface have a decreased, or non-enhanced, gripping functionality.

Additionally, a larger force is necessarily experienced by the adjacent article as a distally-advancing sled driver initially cuts, or otherwise traverses, through the adjacent article. For example, when cutting and stapling a target tissue requiring multiple firings, a first staple cartridge is employed to cut and attach a first adjunct or adjuncts to a first portion of the target tissue. Thereafter, the spent staple cartridge is replaced with a fresh cartridge and a corresponding second adjunct or second adjuncts are positioned in the end effector. The end effector jaws are positioned so that a proximal end of the second adjunct or adjuncts is overlapped with the distal end of the stapled first adjunct or adjuncts and then the jaws are closed to clamp the remaining portion of target tissue between the second adjunct(s) and the jaws. As the sled driver or firing actuator is driven distally, the knife on the firing actuator contacts the overlapping adjunct materials. If the second adjunct materials are permitted to move during this process, the second adjuncts may bunch or "plow" which could cause the second adjuncts to detrimentally affect the staple formation process. This undesirable plowing or bunching is more likely to occur when the knife of the firing actuator or sled driver initially contacts the second adjunct and somewhat diminishes as the sled driver proceeds through the staple cartridge. Thus, it is desirable for the projections located at the proximal end of the staple cartridge to be more aggressive than those in the middle and distal portion of the cartridge. For example, as will be discussed in further detail below, the proximal projections may be higher than the projections in a middle portion of the cartridge and the middle projections may extend higher than the distal projections located in the distal portion of the cartridge. The proximal projections may also be more robust than the middle and distal projections which can address such problem and prevent movement of the adjunct(s) during such stapling operations. As such, the deck surface can provide a greater degree of gripping strength in proximal portions of the deck surface. Given the location-specific benefits of having gripping strength across the cartridge deck, the features impacting the degree of gripping strength can vary longitudinally and/or laterally across the deck surface. Such variances are discussed in greater detail herein.

Figure 43:
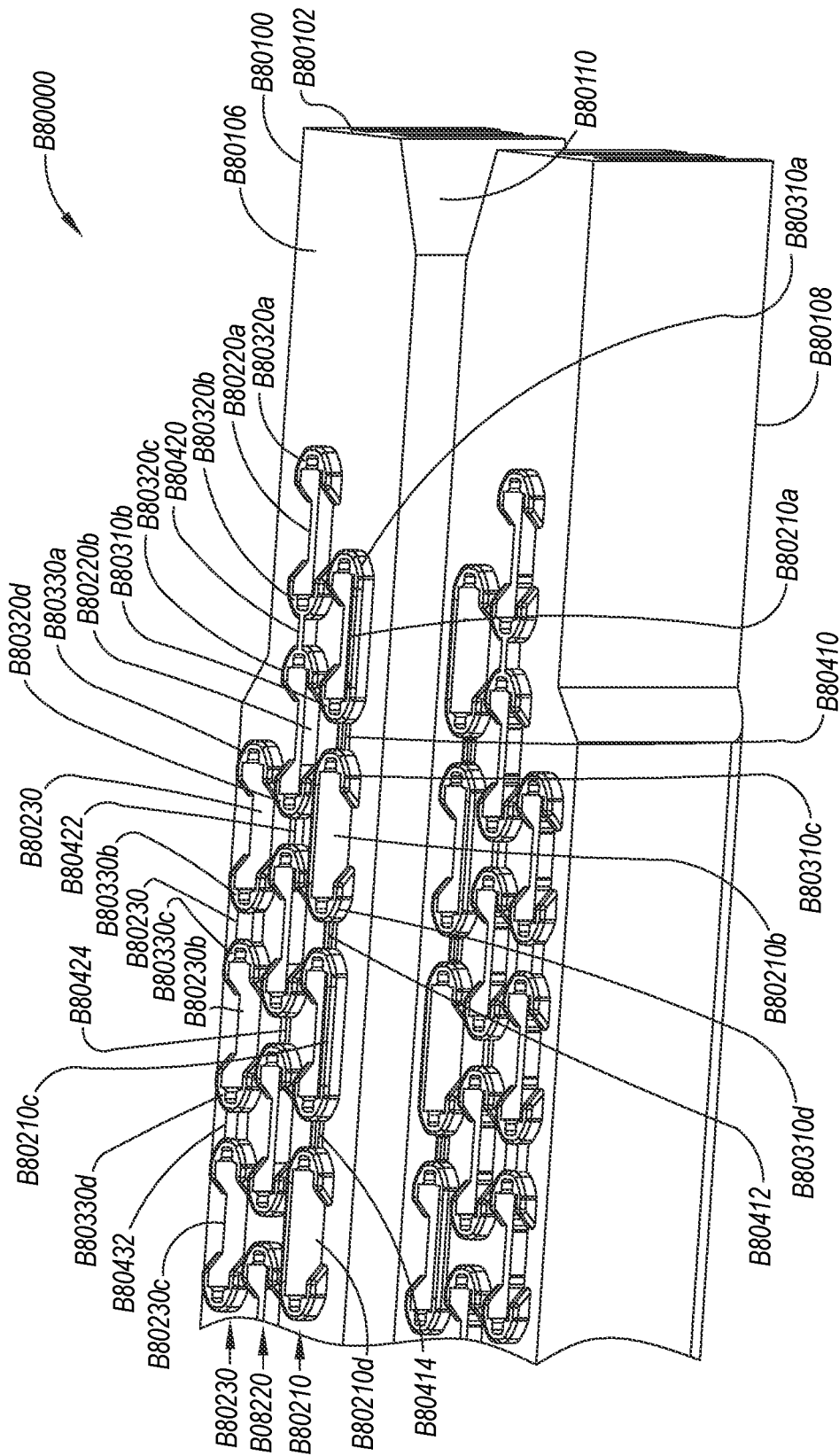
FIG. 43 depicts a partial perspective view of the cartridge body of FIG. 42, the cartridge body including a plurality of projections above a deck surface of the cartridge body.
Figure 44:
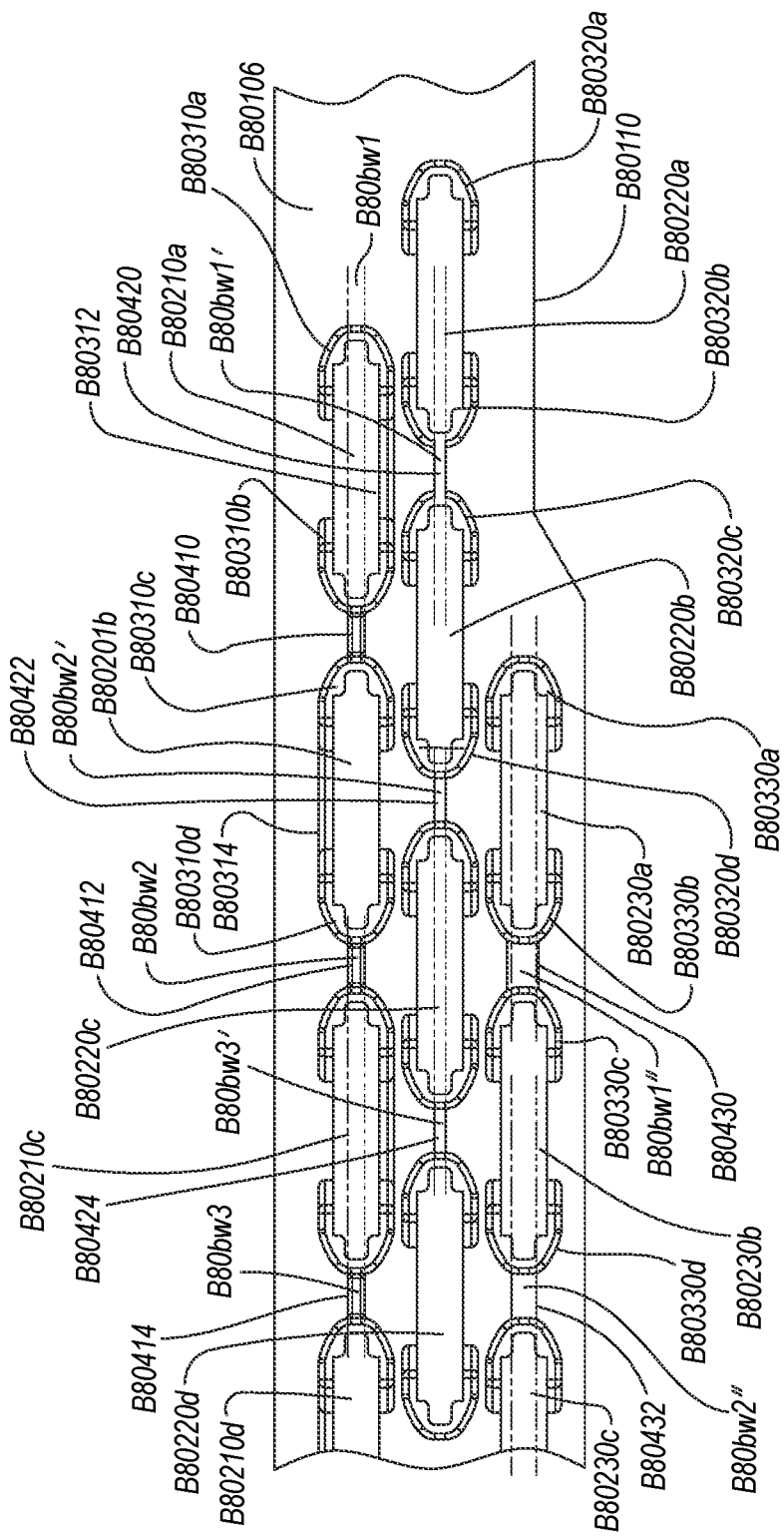
FIG. 44 depicts a partial plan view of the projections extending above the deck surface of the cartridge body of FIG. 42.

Referring now to FIGS. 43 and 44, a portion of cartridge body (B80100) is shown. As described with respect to FIG. 44, three longitudinal rows of staple cavities are defined in the cartridge body (B80100) on each side of the longitudinal slot (B80110). For brevity, the topography with respect to a first side of the longitudinal slot is discussed herein in detail; however, it is envisioned the topography of the deck surface on the first side of the longitudinal slot is mirrored onto the deck surface on the second side of the longitudinal slot. Other arrangements are contemplated wherein the topography of the deck surface on one side of the longitudinal slot differs from the topography of the deck surface on an opposite side of the longitudinal slot. As shown, a first longitudinal row of staple cavities (B80210) extends alongside the longitudinal slot (B80110), a second longitudinal row of staple cavities (B80220) extends alongside the first longitudinal row of staple cavities (B80210), and a third longitudinal row of staple cavities (B80230) extends alongside the second longitudinal row of staple cavities (B80220). The first, second, and third longitudinal rows of staple cavities (B80210, B80220, B80230) are defined on a first side of the longitudinal slot (B80110).

The first longitudinal row of staple cavities (B80210) includes a proximal-most staple cavity (B80210a). Each proximal-most staple cavity (B80210a) comprises corresponding first or proximal projection configuration (B80211a). Each first projection configuration (B80211a) comprises a first projection (B80310a) that surrounds a proximal portion of the proximal-most staple cavity (B80210a), and a second projection (B80310b) that surrounds a distal portion of the proximal-most staple cavity (B80210a). A first intermediate projection (B80312) surrounds an intermediate portion of the proximal-most staple cavity (B80210a) and extends between the first projection (B80310a) and the second projection (B80310b).

A second staple cavity (B80210b) is positioned distal to the proximal-most cavity (B80210a) in the first longitudinal row of staple cavities (B80210). Each staple cavity (B80210b) comprises a corresponding second or middle projection configuration (B80211b). Each second projection configuration (B80211b) comprises a third projection (B80310c) that surrounds a proximal portion of the second staple cavity (B80210b), and a fourth projection (B80310d) that surrounds a distal portion of the second staple cavity (B80210b). A second intermediate projection (B80314) surrounds an intermediate portion of the second staple cavity (B80210b) and extends between the third projection (B80310c) and the fourth projection (B80310d). As shown in FIG. 44, the second intermediate projection (B80314) surrounds an intermediate portion of the second staple cavity (B80210b) on a single side of the staple cavity. In other instances, the second intermediate projection (B80314) can surround an intermediate portion of the second staple cavity (B80210b) on both sides of the staple cavity. Furthermore, the second intermediate projection (B80314) is present on a side of the second staple cavity (B80210b) that is opposite from the side of the first staple cavity (B80210a) on which the first intermediate projection (B80312) is present. In such arrangement, the first projection configuration differs from the second projection configuration.

Figure 45A:
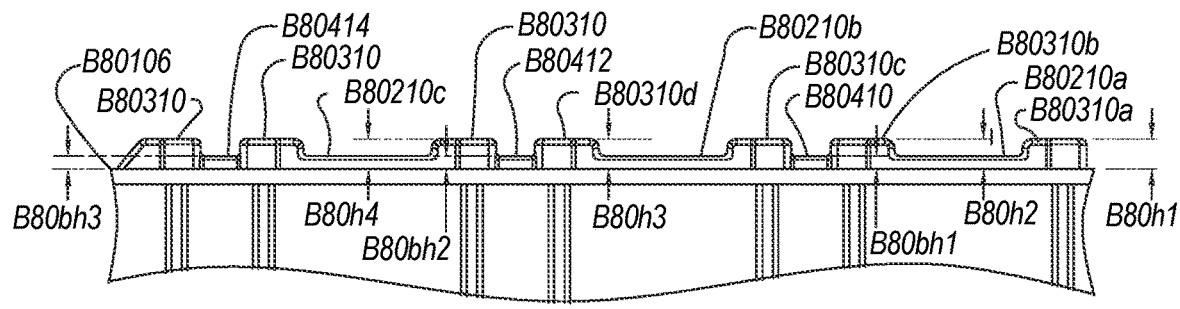
FIG. 45A depicts a partial elevational view of the projections extending above the deck surface of a first longitudinal row of staple cavities of the cartridge body of FIG. 42.

The first projection (B80310a) extends from the deck surface (B80106) to a first height (B80h1), the second projection (B80310b) extends from the deck surface (B80106) to a second height (B80h2). The third projection (B80310c) extends from the deck surface (B80106) to a third height (B80h3), and the fourth projection (B80310d) extends from the deck surface (B80106) to a fourth height (B80h4). As depicted in FIGS. 43 and 45A, the first, second, third, and fourth heights are the same.

The first intermediate projection (B80312) extends from the deck surface (B80106) to a fifth height, and the second intermediate projection (B80314) extends from the deck surface (B80106) to a sixth height. The fifth height is the same as the sixth height; however, in other instances, the heights to which the intermediate projections extend can differ across the staple cartridge.

The fifth height of the first intermediate projection (B80312) is different than the first and second heights of the first and second projections (B80310a, B80310b), respectively. In the illustrated arrangement, the fifth height is less than the first and second heights. The sixth height of the second intermediate projection (B80314) is different than the third and fourth heights of the third and fourth projections (B80310c, B80310d), respectively. In the illustrated arrangement, the sixth height is less than the third and fourth heights. In other instances, the intermediate projection can extend from the deck surface to a height that is the same as the projections between which the intermediate projection extends.

The projections surrounding adjacent staple cavities, or portions thereof, can be directly connected to one another by a bridge projection (also referred to as an interconnection). Stated another way, the second projection of the proximal-most staple cavity is connected to the third projection of the second staple cavity by a longitudinally-extending bridge projection. Connecting bridges improve the holding and/or gripping of the adjacent article to the cartridge body by providing increased surface area for the adjacent article to contact, or otherwise interact with. In the absence of such connecting bridges, the adjacent article requires application of a significant force to engage additional cartridge surfaces absent the projections. Stated another way, the adjacent article requires a significant force to become engaged with the deck surface in the crevices, or valleys, formed between surrounding projections. However, during such force application, the adjacent article is likely to move out its desired position and/or become damaged.

In particular, the second projection (B80310b) of the proximal-most staple cavity (B80210a) in the first longitudinal row of staple cavities (B80210) is directly connected to the third projection (B80310c) of the second staple cavity (B80210b) by the bridge projection (B80410). See FIGS. 44 and 45A. The bridge projection (B80410) extends from the deck surface (B80106) to a first bridge height (B80bh1) (FIG. 45A) and extends laterally a first bridge width (B80bw1) (FIG. 44). The first bridge height is different than the second and third heights of the second and third projections (B80310b, B80310c), respectively. More specifically, the first bridge height is shorter than the second and third heights of the second projection and third projection, respectively.

A second bridge projection (B80412) connects the fourth projection (B80310d) to a projection surrounding a third staple cavity (B80210c) that is distal to the second staple cavity (B80210b). Each third staple cavity (B80210c) comprises a corresponding third or distal projection configuration (B80211c). Each third projection configuration (B80211c) comprises a fifth projection (B80310e) that surrounds a proximal portion of the third staple cavity (B80210c), and a sixth projection (B80310f) that surrounds a distal portion of the third staple cavity (B80210c). The second bridge projection (B80412) extends from the deck surface (B80106) to a second bridge height (B80bh2) and extends laterally a second bridge width (b80bw2). A third bridge projection (B80414) connects a projection surrounding a distal portion of the third staple cavity (B80210c) to a projection surrounding a proximal portion of the fourth staple cavity (B80210d). The third bridge projection (B80414) extends from the deck surface (B80106) to a third bridge height (B80bh3) and extends laterally a third bridge width (B80bw3). As depicted in FIGS. 43-45A, the first bridge height, the second bridge height, and the third bridge height are the same. Furthermore as shown in FIG. 44, the first bridge width, the second bridge width, and the third bridge width are the same. While the bridge projections can continue to directly connect the projections of longitudinally-adjacent staple cavities, FIGS. 43, 44, and 45A depict bridge projections directly connecting the projections of only a proximal set of the first longitudinal row of staple cavities (B80210) (located only in a corresponding proximal portion of the staple cartridge body). Notably, no bridge projection is depicted distal to the fourth staple cavity (B80210d) in the first longitudinal row of staple cavities (B80210).

The second longitudinal row of second staple cavities (B80220) includes a second proximal-most staple cavity (B80220a). Each second proximal-most staple cavity (B80220a) comprises a corresponding second proximal projection configuration (B80221a). The second proximal projection configuration (B80221a) comprises a first projection (B80320a) that surrounds a proximal portion of the proximal-most staple cavity (B80220a), and a second projection (B80320b) that surrounds a distal portion of the proximal-most staple cavity (B80220a). A second staple cavity (B80220b) is positioned distal to the proximal-most cavity (B80220a) in the second longitudinal row of staple cavities (B80220). Each second staple cavity comprises a corresponding second projection configuration (B80221b). The second projection configuration comprises a third projection (B80320c) that surrounds a proximal portion of the second staple cavity (B80220b), and a fourth projection (B80320d) that surrounds a distal portion of the second staple cavity (B80220b).

Figure 45B:
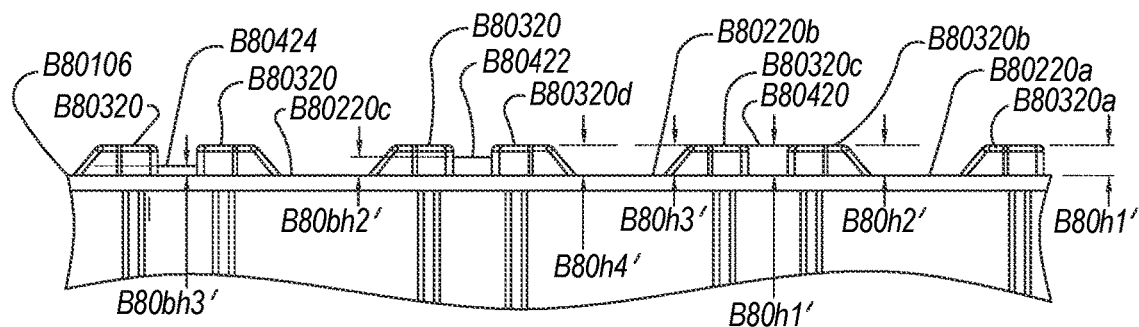
FIG. 45B depicts another partial elevational view of the projections extending above the deck surface of a second longitudinal row of staple cavities of the cartridge body of FIG. 42.

The first projection (B80320a) extends from the deck surface (B80106) to a first height (B80h1'), and the second projection (B80320b) extends from the deck surface (B80106) to a second height (B80h2'). The third projection (B80320c) extends from the deck surface (B80106) to a third height (B80h3'), and the fourth projection (B80320d) extends from the deck surface (B80106) to a fourth height (B80h4'). As depicted in FIGS. 43 and 45B, the first, second, third, and fourth heights are the same.

The second projection (B80320b) of the proximal-most staple cavity (B80220a) from the second longitudinal row of staple cavities (B80220) is directly connected to the third projection (B80320c) of the second staple cavity (B80220b) by a bridge projection (B80420). The bridge projection (B80420) extends from the deck surface (B80106) to a first bridge height (B80bh1') and extends laterally a first bridge width (B80bw1'). As depicted in FIGS. 43 and 45B, the first bridge height (B80bh1') is the same as the second and third heights (B80h1', B80h2', B80h3') of the second and third projections (B80320b, B80320c), respectively.

Still referring to FIG. 44, a third staple cavity (B80220c) is located distal to the second staple cavity (B80220b). The third staple cavity (B80220c) comprises a third projection configuration (B80221c) that is the same or similar to the second projection configuration (B80221b). In the illustrated arrangement, a second bridge projection (B80422) connects the fourth projection (B80320d) to a projection surrounding the third staple cavity (B80220c). The second bridge projection (B80422) extends from the deck surface (B80106) to a second bridge height (B80bh2') and extends laterally a second bridge width (B80bw2'). As depicted in FIGS. 43 and 45B, the second bridge height (B80bh2') is less than the first bridge height (B80bh1'), and the second bridge height (B80bh2') is less than the fourth height (B80h4') of the fourth projection (B80320d).

A fourth staple cavity (B80220d) is located distal to the third staple cavity (B80220c). The fourth staple cavity (B80220d) comprises a fourth projection configuration (B80221d) that is the same or similar to the third projection configuration (B80221c). A third bridge projection (B80424) connects a projection surrounding a distal portion of a third staple cavity (B80210c) to a projection surrounding a proximal portion of a fourth staple cavity (B80210d). The third bridge projection (B80424) extends from the deck surface (B80106) to a third bridge height (B80bh3') and extends laterally a third bridge width (B80bw3'). As depicted in FIGS. 43, 44, and 45B, the third bridge height (B80bh3') is less than the first and second bridge heights (B80bh1', B80bh2'); however, the first bridge width (B80bw1'), the second bridge width (B80bw2'), and the third bridge width (B80bw3') are the same. While the bridge projections can continue to directly connect the projections of longitudinally-adjacent staple cavities, FIGS. 43, 44, and 45B depict bridge projections directly connecting the projections of only a proximal set of the second longitudinal row of staple cavities (B80220). Notably, no bridge projection is depicted distal to the fourth staple cavity (B80220d) in the second longitudinal row of staple cavities (B80220).

The third longitudinal row of staple cavities (B80230) includes a proximal-most staple cavity (B80230a). Each staple cavity (B80230a) comprises a first projection configuration (B80231a). The first projection configuration (B80231a) comprises a first projection (B80330a) that surrounds a proximal portion of the proximal-most staple cavity (B80230a), and a second projection (B80330b) that surrounds a distal portion of the proximal-most staple cavity (B80230a). A second staple cavity (B80230b) is positioned distal to the proximal-most cavity (B80230a) in the second longitudinal row of staple cavities (B80230). Each second staple cavity (B80230b) comprises a second projection configuration (B80231b). The second projection configuration comprises a third projection (B80330c) that surrounds a proximal portion of the second staple cavity (B80230b), and a fourth projection (B80330d) that surrounds a distal portion of the second staple cavity (B80230b).

Figure 45C:
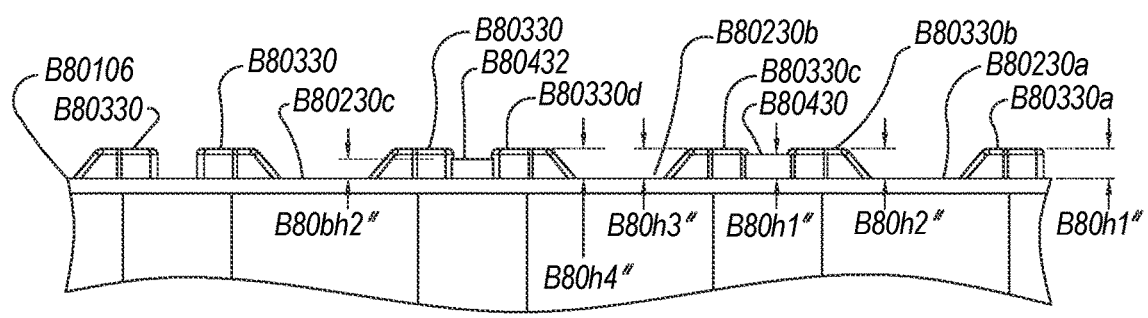
FIG. 45C depicts yet another partial elevational view of the projections extending above the deck surface of a third longitudinal row of staple cavities of the cartridge body of FIG. 42.

The first projection (B80330a) extends from the deck surface (B80106) to a first height (B80h1"), and the second projection (B80330b) extends from the deck surface (B80106) to a second height (B80h2"). The third projection (B80330c) extends from the deck surface (B80106) to a third height (B80h3"), and the fourth projection (B80330d) extends from the deck surface (B80106) to a fourth height (B80h4"). As depicted in FIGS. 43 and 45C, the first, second, third, and fourth heights are the same.

The second projection (B80330b) of the proximal-most staple cavity (B80230a) from the third longitudinal row of staple cavities (B80230) is directly connected to the third projection (B80330c) of the second staple cavity (B80230b) by a bridge projection (B80430(. The bridge projection (B80430) extends from the deck surface (B80106) to a first bridge height (B80bh1") and extends laterally a first bridge width (B80bw1"). As depicted in FIGS. 43 and 45C, the first bridge height (B80bh1") is different than the second (B80h2") and third heights (B80h3") of the second and third projections (B80320b, B80320c), respectively. More specifically, the first bridge height (B80bh1") is less than the second and third heights (B80h2", B80h3") of the second and third projections, respectively.

A third staple cavity (B80230c) is located distal to the second staple cavity (B80230b). The third staple cavity comprises a third projection configuration (B80231c). A second bridge projection (B80432) connects the fourth projection (B80330d) to a projection surrounding a third staple cavity (B80230c). The second bridge projection (B80432) extends from the deck surface (B80106) to a second bridge height (B80bh2") and extends laterally a second bridge width (B80bw2"). As depicted in FIGS. 43, 44, and 45C, the second bridge height (B80bh2") is the same as the first bridge height (B80bh1"); however, the second bridge width (B80bw2") is less than the first bridge width (B80bw1"). Varying the width of the projections and/or bridge projections provides increased surface area and/or contact area with the adjacent article which thereby increases retention. While the bridge projections can continue to directly connect the projections of longitudinally-adjacent staple cavities, FIGS. 43, 44, and 45C depict bridge projections directly connecting the projections of only a proximal set of the third longitudinal row of staple cavities (B80230). Notably, no bridge projection is depicted distal to the third staple cavity (B80230c) in the third longitudinal row of staple cavities (B80230).

While the bridge connections are shown as connecting staple cavities from within the same longitudinal row, it is envisioned that such bridge connections could also, or alternatively, connect staple cavities from different longitudinal rows. Such connections could be in the form of diagonal bridge projections, for example. The diagonal bridge projections provide an added benefit as the distance covered necessarily involves a larger surface area than bridge projections connecting staple cavities within the same longitudinal row. Bridge connections can be used in varying locations along the cartridge deck to achieve a desired retention effect.

M. Thirteenth Example of a Cartridge Body

Figure 46:
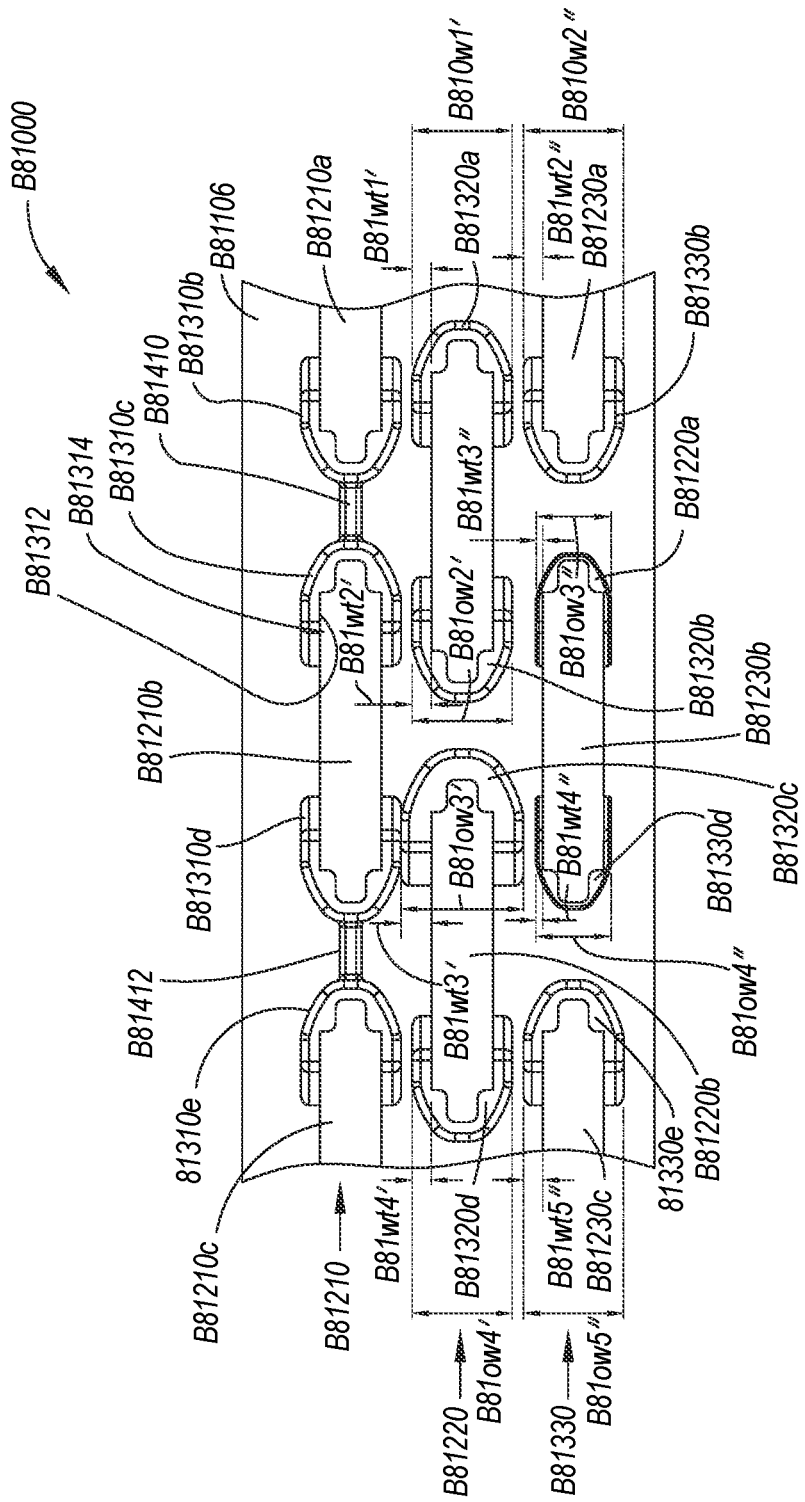
FIG. 46 depicts a partial plan view of another example of a cartridge body configured to be incorporated into the staple cartridge of FIG. 7 and the end effector of FIG. 2, the cartridge body including projections extending above a deck surface.
Figure 47:
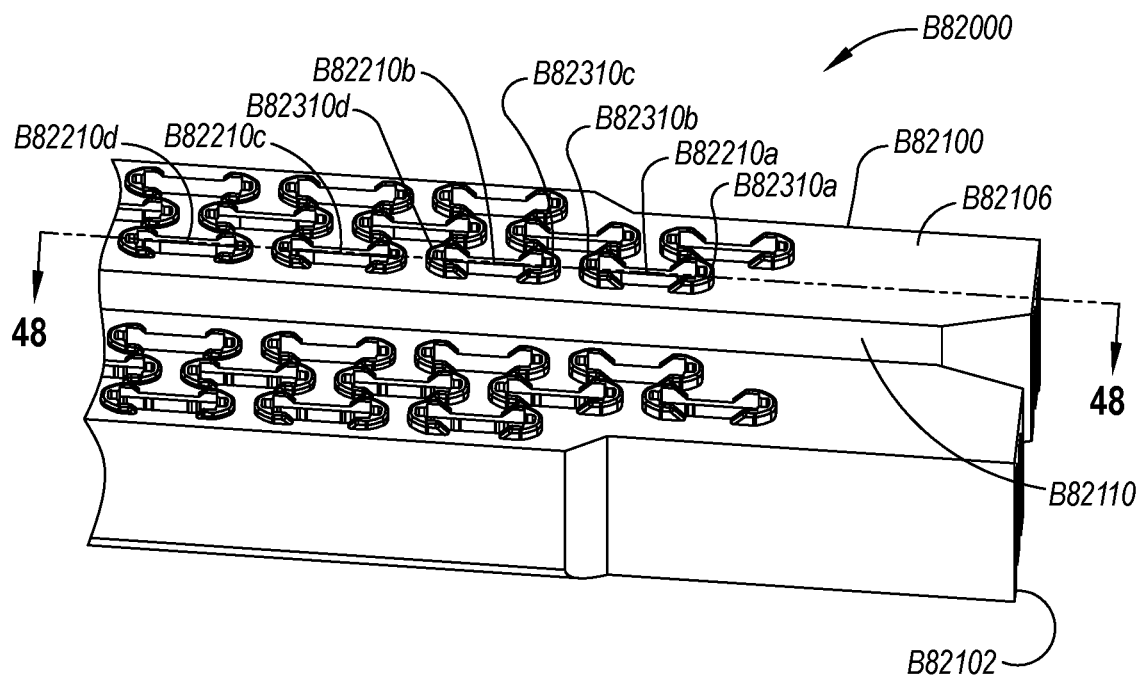
FIG. 47 depicts a partial perspective view of another example of a cartridge body configured to be incorporated into the staple cartridge of FIG. 7 and the end effector of FIG. 2, the cartridge body including projections extending above a deck surface.

FIG. 46 depicts a portion of a cartridge body (B81100) that is similar in many respects to cartridge body (B80100) described above. Cartridge body (B81100) defines a proximal end and a distal end and a deck surface (B81106) that extends therebetween. A first longitudinal row of staple cavities (B81210) extends alongside a longitudinal slot (B81110) defined in the cartridge body (B81100), a second longitudinal row of staple cavities (B81220) extends alongside the first longitudinal row of staple cavities (B81210), and a third longitudinal row of staple cavities (B81230) extends alongside the second longitudinal row of staple cavities (B81220). The first, second, and third longitudinal rows of staple cavities (B81210, B81220, B81230) are defined on a first side of the longitudinal slot.

The first longitudinal row of staple cavities (B81210) includes a first staple cavity (B81210a). A second projection (B81310b) surrounds a distal portion of the first staple cavity (B81210a) having a second overall width SW and a second projection wall thickness SPWT. The second projection wall thickness SPWT is defined by the thickness of the projection measured between a cavity-facing wall (B81312) and an opposite, external wall (B81314). A second staple cavity (B81210b) is positioned distal to the first cavity (B81210a) in the first longitudinal row of staple cavities (B81210). A third projection (B81310c) surrounds a proximal portion of the second staple cavity (B81210b), and a fourth projection (B81310d) surrounds a distal portion of the second staple cavity (B81210b). The third projection (B81310c) has a third overall width TW and a third projection wall thickness TPWT that is defined by the thickness of the projection (B81310c) measured between a cavity-facing wall (B81316) and an opposite, external wall (B81318). The fourth projection (B81310d) has a fourth overall width FW and a fourth projection wall thickness FPWT that is defined by the thickness of the fourth projection (B81310d) measured between a cavity-facing wall (B81317) and an opposite, external wall (B81319). A third staple cavity (B81210c) is positioned distal to the second cavity (B81210b) in the first longitudinal row of staple cavities (B81210). A fifth projection (B81310e) surrounds a proximal portion of the third staple cavity (B81210c). The fifth projection (81310e) has a fifth overall width FTW and a fifth projection wall thickness FTPWT. As shown in FIG. 46, the second, third, fourth, and fifth overall widths are the same, and the second, third, fourth, and fifth projection wall thicknesses are the same.

A first bridge projection (B81410) directly connects the second projection (B81310b) to the third projection (B81310c). The first bridge projection (B81410) extends to a first height above the deck surface (B81106) and has a first lateral width. A second bridge projection (B81412) directly connects the fourth projection (B81310d) to the fifth projection (B81310e). The second bridge projection (B81412) extends to a second height above the deck surface (B81106) and has a second lateral width. The first height is the same as the second height and, as shown in FIG. 46, the first lateral width is the same as the second lateral width.

The second longitudinal row of staple cavities (B81220) includes a first staple cavity (B81220a). A first projection (B81320a) surrounds a proximal portion of the first staple cavity (B81220a) having a first overall width (B81ow1') and a first projection wall thickness (B81wt1'), and a second projection (B81320b) surrounds a distal portion of the first staple cavity (B81220a) having a second overall width (B81ow2') and a second projection wall thickness (B81wt2'). As shown in FIG. 46, the first overall width (B81ow1') and the second overall width (B81ow2') are the same. Similarly, the first projection wall thickness (B81wt1') is the same as the second projection wall thickness (B81wt2').

A second staple cavity (B81220b) is positioned distal to the first cavity (B81220a) in the second longitudinal row of staple cavities (B81220). A third projection (B81320c) surrounds a proximal portion of the second staple cavity (B81220b), and a fourth projection (B81320d) surrounds a distal portion of the second staple cavity (B81220b). The third projection (B81320c) has a third overall width (B81ow3') and a third projection wall thickness (B81wt3'). The fourth projection (B81320d) has a fourth overall width (B81ow4') and a fourth projection wall thickness (B81wt4'). As shown in FIG. 46, the fourth overall width (B81ow4') is the same as the first and second overall widths (B81ow1', B81ow2') while the third overall width (B81ow3') is greater than the fourth overall width (B81ow4'). Similarly, the fourth projection wall thickness (B81wt4') is the same as the first and second projection wall thicknesses (B81wt1', B81wt2') while the third projection wall thickness (B81wt3') is greater than the fourth projection wall thickness (B81wt4').

The third longitudinal row of staple cavities (B81230) includes a first staple cavity (B81230a). A second projection (B81330b) surrounds a distal portion of the first staple cavity (B81230a) having a second overall width (B81ow2") and a second projection wall thickness (B81wt2"). A second staple cavity (B81230b) is positioned distal to the first cavity (B81230a) in the third longitudinal row of staple cavities (B81230). A third projection (B81330c) surrounds a proximal portion of the second staple cavity (B81230b), and a fourth projection (B81330d) surrounds a distal portion of the second staple cavity (B81230b). The third projection (B81330c) has a third overall width (B81ow3") and a third projection wall thickness (B81wt3"). The fourth projection (B81330d) has a fourth overall width (B81ow4") and a fourth projection wall thickness (B81wt4"). A third staple cavity (B81230c) is positioned distal to the second cavity (B81230b) in the third longitudinal row of staple cavities (B81230). A fifth projection (B81330e) surrounds a proximal portion of the third staple cavity (B81230c). The fifth projection (B81330e) has a fifth overall width (B81ow5") and a fifth projection wall thickness (B81wt5"). As shown in FIG. 46, the second and fifth overall widths are the same, and the second and fifth projection wall thicknesses are the same. However, while the third and fourth overall widths are the same, the third and fourth overall widths are less than the second and fifth overall widths. Similarly, while the third and fourth projection wall thicknesses are the same, the third and fourth projection wall thicknesses are less than the second and fifth projection wall thicknesses.

N. Fourteenth Example of a Cartridge Body

Figure 48:
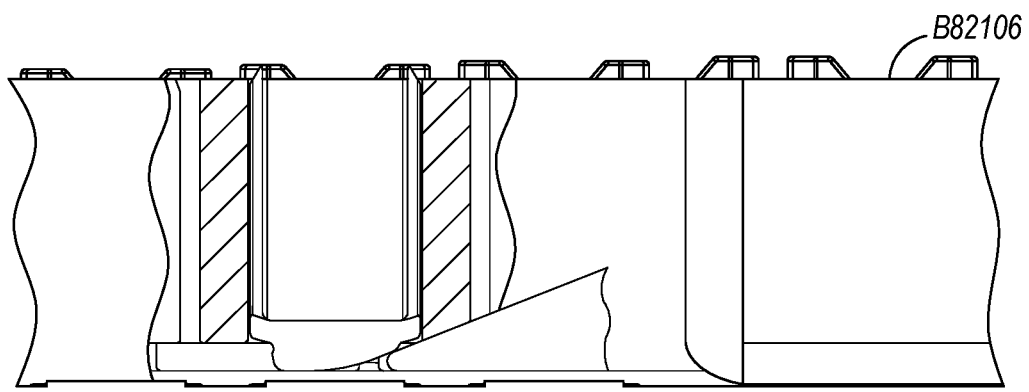
FIG. 48 depicts a partial cross-sectional view of the cartridge body of FIG. 47 taken along line 48-48 of FIG. 47.
Figure 49:
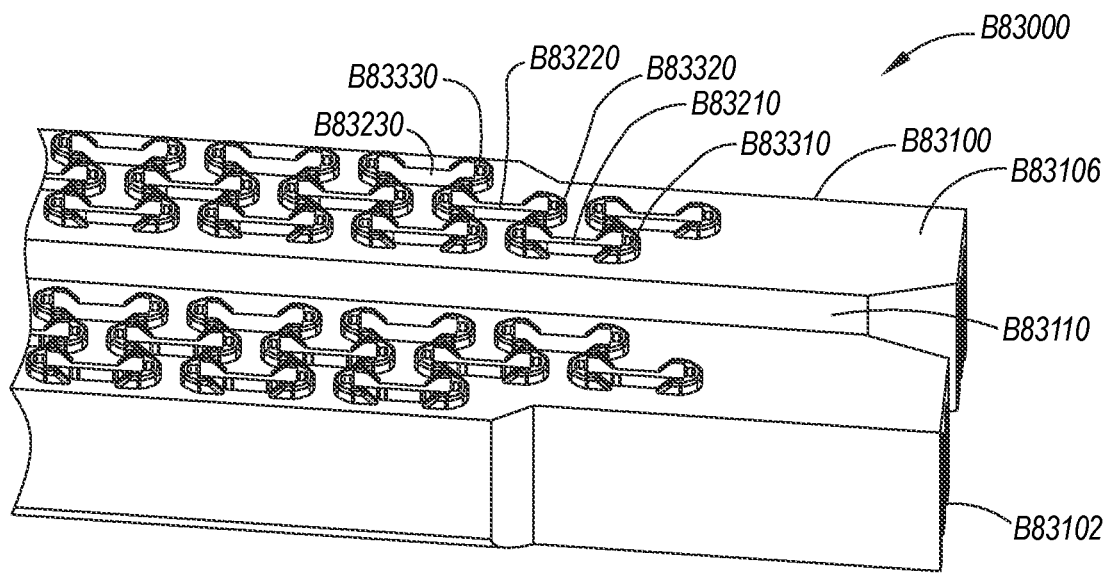
FIG. 49 depicts a partial perspective view of another example of a cartridge body configured to be incorporated into the staple cartridge of FIG. 7 and the end effector of FIG. 2, the cartridge body including projections extending above a deck surface.

FIGS. 48 and 49 show a cartridge body (B82100) that is similar in many respects to cartridge bodies (B80100, B81100) described above. Cartridge body (B82100) comprises a deck surface (B82106) and a longitudinal slot (B82110). Longitudinal slot (B82110) is defined in cartridge body (B82100) and extends from a proximal end (B82102) of the cartridge body (B82100) toward a distal end. A first longitudinal row of staple cavities (B82210) extends alongside the longitudinal slot (B82110) on a first side of the longitudinal slot (B82110). A proximal-most staple cavity (B82210a) is defined in the cartridge body (B82100) as part of the first longitudinal row of staple cavities (B82210). A first projection (B82310a) surrounds a proximal portion of the proximal-most staple cavity (B82210a), and the first projection (B82310a) extends a first height above the deck surface (B82106). A second projection (B82310b) surrounds a distal portion of the proximal-most staple cavity (B82210a), and the second projection (B82310b) extends a second height above the deck surface (B82106). As shown in FIG. 48, the first height is the same as the second height.

A second staple cavity (B82210b) is defined in the cartridge body (B82100) distal to the proximal-most staple cavity (B82210a). A third projection (B82310c) surrounds a proximal portion of the second staple cavity (B82210b), and the third projection (B82310c) extends a third height above the deck surface (B82106). A fourth projection (B82310d) surrounds a distal portion of the second staple cavity (B82210b), and the fourth projection (B82310d) extends a fourth height above the deck surface (B82106). As shown in FIG. 48, the third height is the same as the fourth height; however, the third and fourth heights are different than the first and second heights. More specifically, the third and fourth heights are less than the first and second heights.

A third staple cavity (B82210c) is defined in the cartridge body (B82100) distal to the second staple cavity (B82210b). A fifth projection (B82310e) surrounds a proximal portion of the third staple cavity (B82210c), and the fifth projection (B82310c) extends a fifth height above the deck surface (B82106). A sixth projection (B82310f) surrounds a distal portion of the third staple cavity (B82210c), and the sixth projection (B82310f) extends a sixth height above the deck surface (B82106). As shown in FIG. 48, the fifth height is the same as the fifth height; however, the fifth and sixth heights are different than the first, second, third, and fourth heights. More specifically, the fifth and sixth heights are less than the first, second, third, and fourth heights.

Although the heights of the projections associated with an individual staple cavity are illustrated as being the same, it is envisioned that the height of each projection can follow the gradient, such as a linear decrease in height, of the other projection heights. More specifically, the first height of the first projection (B82310a) could be greater than the second height of the second projection (B82310b) even though they surround portions of the same staple cavity (B82210a). When an adjunct material is used, an initial engagement of the knife with the adjunct material may tend to undesirably urge the adjunct material distally as the knife initially severs the material and continues to proceed distally through the material. Thus, by making the heights of the proximal-most projections greater than the distally-proceeding projections helps to retain the adjunct material in position during this portion of the firing procedure.

O. Fifteenth Example of a Cartridge Body

Figure 50:
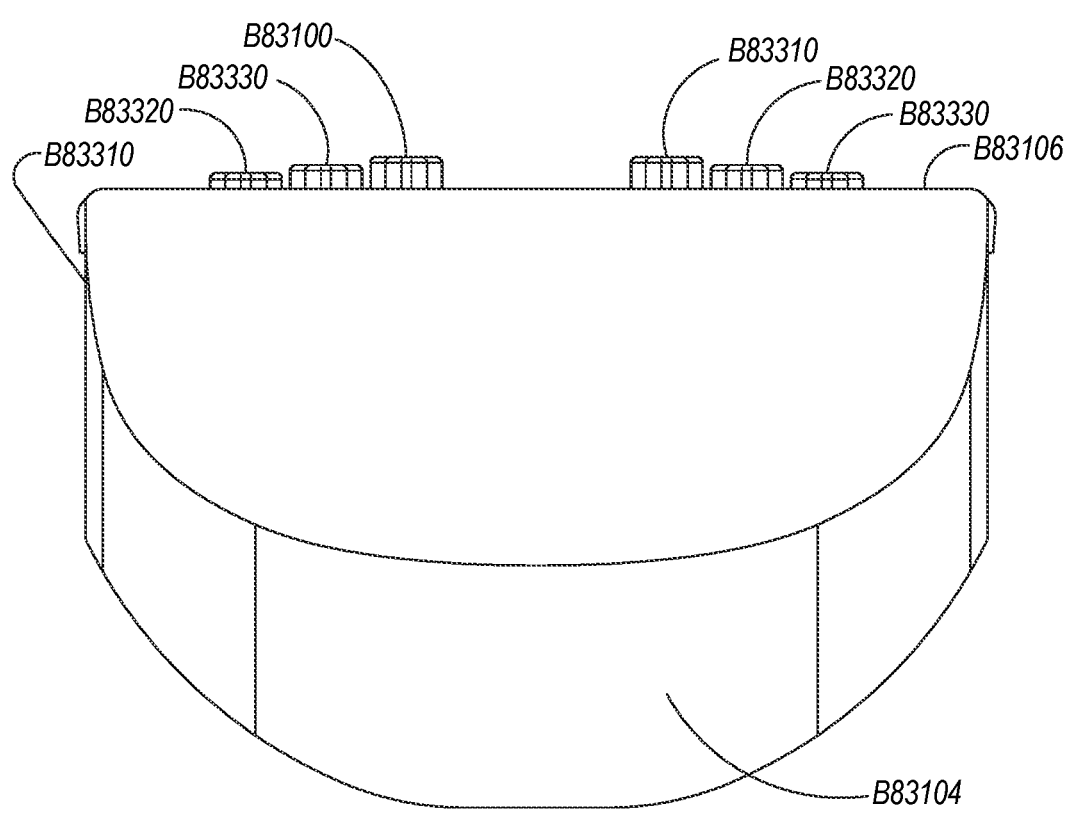
FIG. 50 depicts a front elevational view of the cartridge body of FIG. 49.

FIGS. 49 and 50 show a cartridge body (B83100) that is similar in many respects to cartridge bodies (B80100, B81100, B82100) described above. Cartridge body (B83100) comprises a deck surface (B83106) and a longitudinal slot (B83110). Longitudinal slot (B83110) is defined in the cartridge body (B83100) and extends from a proximal end (B83102) of the cartridge body (B83100) toward a distal end (B83104). A first longitudinal row of staple cavities (B83210) extends alongside the longitudinal slot (B83110) on a first side of the longitudinal slot (B83110). A first projection (B83310) surrounds at least a portion of a staple cavity (B83210) within the first longitudinal row. The first projection (B83310) extends a first height above the deck surface (B83106).

A second longitudinal row of staple cavities (B83220) extends alongside the first longitudinal row of staple cavities (B83210) on the first side of the longitudinal slot (B83110). A second projection (B83320) surrounds at least a portion of a staple cavity (B83220) within the second longitudinal row. The second projection (B83320) extends a second height above the deck surface (B83106). As shown in FIG. 50, the first height is different than the second height. More specifically, the first height is greater than the second height.

A third longitudinal row of staple cavities (B83230) extends alongside the second longitudinal row of staple cavities (B83220) on the first side of the longitudinal slot (B83110). A third projection (B83330) surrounds at least a portion of a staple cavity (B83230) within the third longitudinal row. The third projection (B83330) extends a third height above the deck surface (B83106). As shown in FIG. 50, the first projection (B83310) is discrete from or otherwise extends from the deck surface independent of the second projection (B83320) which is discrete from or otherwise extends from the deck surface independent of the third projection (B83330). The third height is different than the second height, and the third height is different than the first height. More specifically, the third height is less than the second height and the first height.

P. Sixteenth Example of a Cartridge Body

Figure 51:
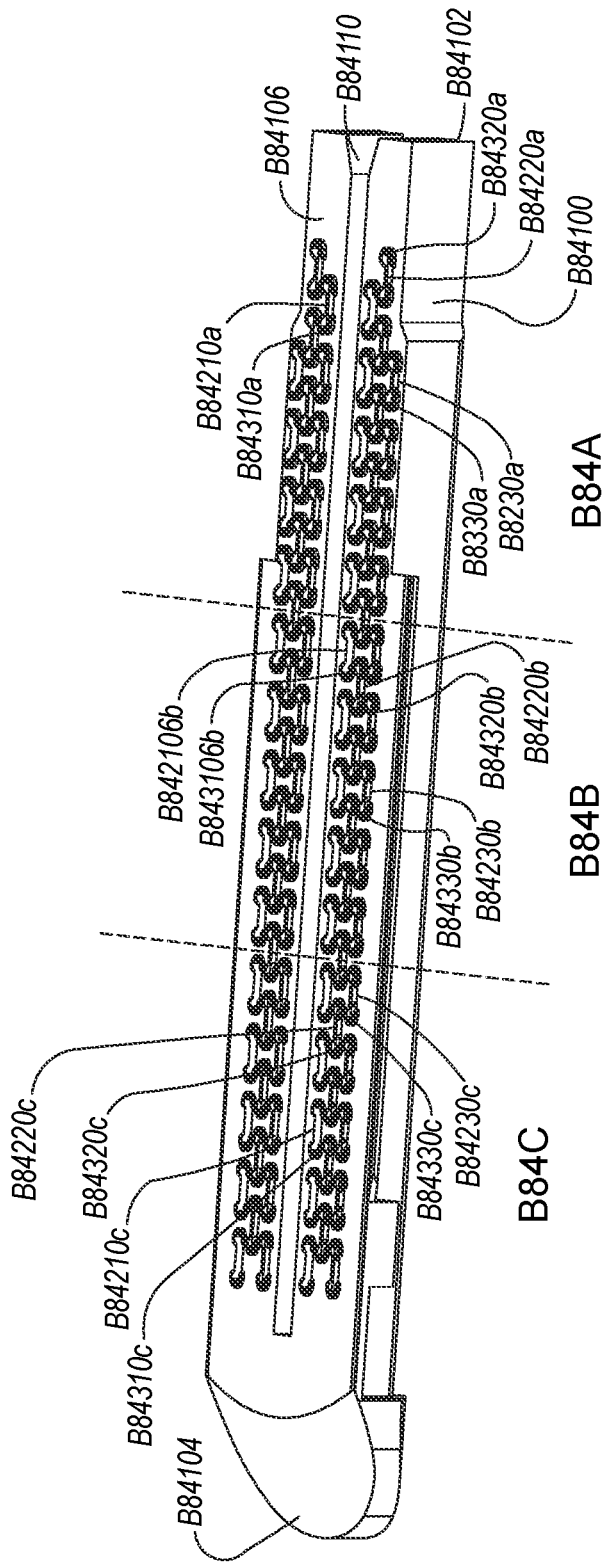
FIG. 51 depicts a perspective view of another example of a cartridge body configured to be incorporated into the staple cartridge of FIG. 7 and the end effector of FIG. 2, the cartridge body including projections extending above a deck surface.
Figure 52:
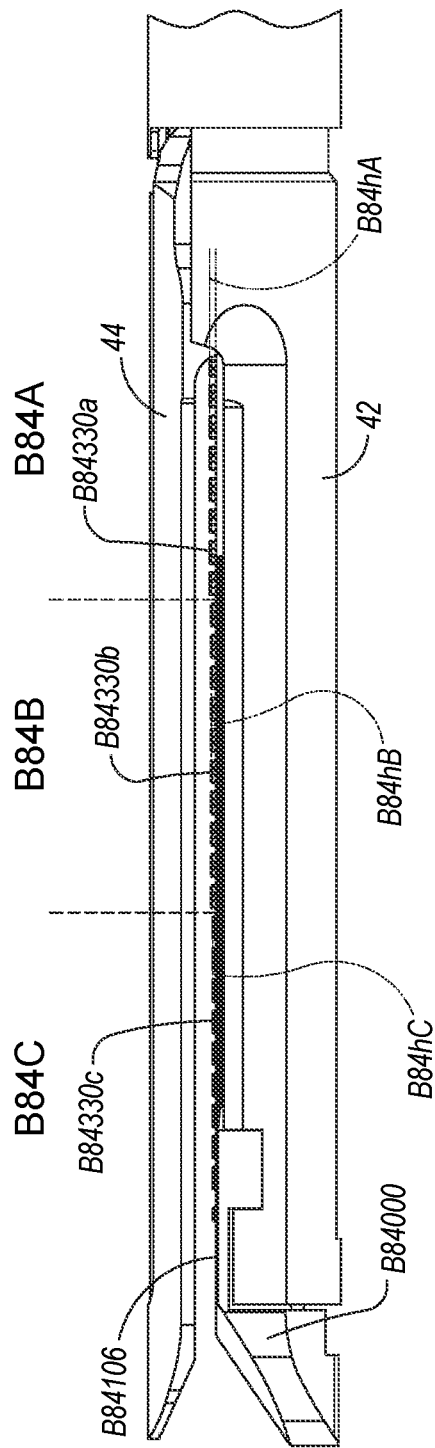
FIG. 52 depicts an elevational view of the cartridge body of FIG. 51 seated in a cartridge jaw of a surgical end effector and opposing an anvil when the surgical end effector is in a closed position.

FIGS. 51 and 52 show a cartridge body (B84100) that is similar in many respects to cartridge bodies (B80100, B81100, B82100, B83100) described above. Cartridge body (B84100) includes a deck surface (B84106) and a longitudinal slot (B84110). Longitudinal slot (B84110) is defined in the cartridge body (B84100) and extends from a proximal end (B84102) toward a distal end (B84104). A first longitudinal row (B84210) of staple cavities extends alongside the longitudinal slot (B84110), a second longitudinal row (B84220) of staple cavities extends alongside the first longitudinal row (B84210), and a third longitudinal row (B84230) of staple cavities extends alongside the second longitudinal row (B84220). The first, second, and third longitudinal rows (B84210, B84220, B84230) of staple cavities are defined on a first side of the longitudinal slot (B84110). For brevity, the topography with respect to a first side of the longitudinal slot is discussed herein in detail; however, it is envisioned that the topography of the deck surface on the first side of the longitudinal slot is mirrored onto the deck surface on the second side of the longitudinal slot. Other arrangements are contemplated wherein the topography of the deck surface on one side of the longitudinal slot differs from the topography of the deck surface on the other side of the longitudinal slot.

As shown in FIG. 51, the deck surface (B84106) has been divided into a proximal portion (B84A), a middle portion (B84B) and a distal portion (B84C). The proximal portion (B84A) of the deck surface (B84106) contains "proximal" segments of the first longitudinal row (B84210), the second longitudinal row (B84220), and the third longitudinal row (B84230). The proximal segment of the first longitudinal row (B84210) includes a plurality of proximal staple cavities (B84210a). The proximal segment of the second longitudinal row (B84220) includes a plurality of second proximal staple cavities (B84220a). The proximal segment of the third longitudinal row (B84230) includes a plurality of third proximal staple cavities (B84230a).

The middle portion (B84B) of the deck surface (B84106) contains "middle" segments of the first longitudinal row (B84210), the second longitudinal row (B84220), and the third longitudinal row (B84230) of staple cavities. The middle segment of the first longitudinal row (B84210) includes a plurality of middle staple cavities (B84210b). The middle segment of the second longitudinal row (B84220) includes a plurality of second middle staple cavities (B84220b). The middle segment of the third longitudinal row (B84230) contains a plurality of third middle staple cavities (B84230b).

The distal portion (B84C) of the deck surface (B84106) contains "distal" segments of the first longitudinal row (B84210), the second longitudinal row (B84220), and the third longitudinal row (B84230). The distal segment of the first longitudinal row (B84210) includes a plurality of distal staple cavities (B84210c). The distal segment of the second longitudinal row (B84220) includes a plurality of second distal staple cavities (B84220c). The distal segment of the third longitudinal row (B84230) includes a plurality of third distal staple cavities (B84230c).

In accordance with at least one embodiment, projections extend from the deck surface (B84106) and surround at least a portion of individual staple cavities. In the illustrated arrangement, each proximal staple cavity (B84210a) comprises a corresponding proximal projection configuration (B84211a). Each proximal projection configuration comprises a first projection (B84310a) that surrounds the corresponding proximal staple cavity (B84210a) in the proximal segment of the first longitudinal row (B84210) in the proximal portion (B84A) of cartridge body (84100). The first projection (B84310a) extends to a first height above the deck surface (B84106). Other arrangements are contemplated wherein the first projection (B84310a) only partially surrounds a corresponding staple cavity (B84210a). Each of the middle staple cavities (B84210b) comprises a corresponding middle projection configuration (B84211b). Each middle projection configuration (B84211b) comprises a second projection (B84310b) that surrounds the corresponding middle staple cavity 84210b in the middle segment of the first longitudinal row 84210 in a middle portion (B84B) of the cartridge body (B84100). The second projection (B84310b) extends to a second height above the deck surface (B84106). The second height is different than the first height. More specifically, the first height is greater than the second height. Other arrangements are contemplated wherein the second projection (B84310b) only partially surrounds a corresponding middle staple cavity (B84210b). Each, or at least a plurality of the distal staple cavities (B84210c) comprise a corresponding distal projection configuration (B84211c.). Each proximal projection configuration (B84211c) comprises a third projection (B84310c) surrounds the corresponding distal staple cavity (B84210c) in the distal segment (B84210D) of the first longitudinal row (B84210) in a distal portion (B84C) of the cartridge body (B84100). The third projection (B84310c) extends to a third height above the deck surface (B84106). The third height is different than the second height, and the third height is different than the first height. More specifically, the first height is greater than the third height, and the second height is greater than the third height. Other arrangements are contemplated wherein the third projection (B84310c) only partially surrounds a corresponding staple cavity (B84210c).

As can be further seen in FIG. 51, each second proximal staple cavity (B84220a) comprises a second proximal projection configuration (B84221a). Each second proximal projection configuration (B84221a) comprises a first projection (B84320a) that surrounds the corresponding second proximal staple cavity (B84220a) in the proximal segment of the second longitudinal row (B84220) in the proximal portion (B84A) of the cartridge body (B84100). The first projection (B84320a) extends to a first height above the deck surface (B84106). Other arrangements are contemplated wherein the first projection (B84320a) only partially surrounds a corresponding staple cavity (B84220a). Each second middle staple cavity (B84220b) comprises a second middle projection configuration (B84221b). Each second middle projection configuration (B84221b) comprises a second projection (B84320b) that surrounds the corresponding second middle staple cavity (B84220b) in the middle segment of the second longitudinal row (B84220) in a middle portion (B84B) of the cartridge body (B84100). The second projection (B84320b) extends to a second height above the deck surface (B84106). The second height is different than the first height. More specifically, the first height is greater than the second height. Other arrangements are contemplated wherein the second projection (B84320b) only partially surrounds a corresponding staple cavity (B84220b).

Each, or at least a plurality of the second distal staple cavities (B84220c), comprises a second distal projection configuration (B84221c). Each second distal projection configuration (B84221c) comprises a third projection (B84320c) that surrounds a corresponding second distal staple cavity (B84220c) in the distal segment of the second longitudinal row (B84220) in the distal portion (B84C) of the cartridge body (B84100). The third projection (B84320c) extends to a third height above the deck surface (B84106). The third height is different than the second height, and the third height is different than the first height. More specifically, the first height is greater than the third height, and the second height is greater than the third height. Other arrangements are contemplated wherein the third projection (B84320c) only partially surrounds a corresponding second distal staple cavity (B84220c).

Still referring to FIG. 51 and FIG. 52, each third proximal staple cavity (B84230a) comprises a third proximal projection configuration (B84231a). Each third proximal projection configuration (B84231a) comprises a first projection (B84330a) that surrounds the corresponding third proximal staple cavity (B84230a) in the proximal segment of the third longitudinal row (B84230) in the proximal portion (B84A) of the cartridge body (B84100). The first projection (B84330a) extends to a first height (B84hA) above the deck surface (B84106). Other arrangements are contemplated wherein the first projection (B84330a) only partially surrounds a corresponding third proximal staple cavity (B84230a). Each third middle staple cavity (B84230b) comprises a third middle projection configuration (B84231b). Each third middle projection configuration (B84231b) comprises a second projection (B84330b) that surrounds a corresponding third middle staple cavity (B84230b) in the middle segment of the third longitudinal row (B84230) in the middle portion of the cartridge body (B84100). The second projection (B84330b) extends to a second height (B84hB) above the deck surface (B84106). The second height (B84hB) is different than the first height (B84hA). More specifically, the first height (B84hA) is greater than the second height (B84hB). Other arrangements are contemplated wherein the second projection (B84330b) only partially surrounds a corresponding third middle staple cavity (B84230b). As can be further seen in FIG. 51, each third distal staple cavity (B84230c) comprises a third distal projection configuration (B84231c). Each third distal projection configuration (B84231a) comprises a third projection (B84330c) that surrounds the corresponding third distal staple cavity (B84230c) in the distal segment of the third longitudinal row (B84230) in a distal portion of the cartridge body (84100). The third projection (B84330c) extends to a third height (B84hC) above the deck surface (B84106). The third height (B84hC) is different than the second height (B84hB), and the third height (B84hC) is different than the first height (B84hA). More specifically, the first height (B84hA) is greater than the third height B84hC), and the second height (B84hB) is greater than the third height (B84hC). Other arrangements are contemplated wherein the third projection (B84330c) only partially surrounds a corresponding staple cavity (B84230c).

The first heights (B84hA) associated with the first projections (B84310a, B84320a, B84330a) of the various longitudinal rows are the same. The second heights (B84hB) associated with the second projections (B84310b, B84320b, B84330b) of the various longitudinal rows are the same. The third heights (B84hC) associated with the third projections (B84310c, B84320c, B84330c) of the various longitudinal rows are the same. Stated another way, the heights of projections decrease longitudinally across the cartridge body (B84100).

In particular, the projections in a first, proximal portion (B84A) of the cartridge body (B84100) extend closer to a tissue-facing surface of anvil (44) when the end effector (40) is in a closed position than the projections in a second, middle portion (B84B) and a third, distal portion (B84C). Due to the shortened gap between the projections (B84310a, B84310b, B84310c) and the tissue-facing surface of the anvil (44), the patient tissue and/or adjunct layer captured between the anvil (44) and the cartridge body (B84100) in the proximal portion (B84A) experiences a greater clamping, or retention, force than the contents captured therebetween in the middle portion (B84B) and distal portion (B84C). The greater retention force aids in maintaining the captured contents in a desired position. While the patient tissue and/or adjunct layer captured between the projections (B84310b, B84320b, B84320c) and the tissue-facing surface of the anvil (44) is compressed to a lesser degree in the middle portion (B84B) of the cartridge body (B84100), such captured contents are compressed to a greater degree than in the distal portion (B84C) of the cartridge body (B84100).

More specifically, a gap distance is defined between a deck surface (B84106) of cartridge body (B84100) and a tissue-facing surface of an anvil (44) when end effector (40) is in a closed position. The height of the projections in the first, proximal portion (B84A) are envisioned as being greater than or equal to 80% of the gap distance while not exceeding 100% of the gap distance.

As discussed above, in at least one embodiment, the first proximal staple cavities, the first middle staple cavities, and the first distal staple cavities are longitudinally aligned and are adjacent to the longitudinal slot. The second proximal staple cavities, the second middle staple cavities and the second distal staple cavities are longitudinally aligned and are adjacent to the first proximal staple cavities, the first middle staple cavities, and the first distal staple cavities. The third proximal staple cavities, the third middle staple cavities and the third distal staple cavities are longitudinally aligned and are adjacent to the second proximal staple cavities, the second middle staple cavities, and the second distal staple cavities as well as a longitudinal edge the cartridge body.

Other arrangements are contemplated wherein the first projection configurations adjacent the longitudinal slot have heights that are greater than the second and third projection configurations. In such arrangements, for example, all of, or at least a plurality of, the first proximal staple cavities in a proximal portion (B84A) of the staple cartridge have first proximal projection configurations that have a first proximal height that is greater than the second proximal height of each of the second proximal projection configurations associated with all of, or at least a plurality of the second proximal staple cavities in the proximal portion (B84A). The third proximal projection configurations associated with all of, or at least a plurality of the third proximal staple cavities in the proximal portion (B84A) of the cartridge have a third proximal height that is less than the second proximal height. All of, or at least a plurality of, the first middle staple cavities in a middle portion (B84B) of the staple cartridge have first middle projection configurations that have a first middle height that is greater than a second middle height of each of the second middle projection configurations associated with all of, or at least a plurality of the second middle staple cavities in the middle portion (B84B). The third middle projection configurations associated with all of, or at least a plurality of the third middle staple cavities in the middle portion (B84B) of the cartridge have a third middle height that is less than the second middle height. All of, or at least a plurality of, the first distal staple cavities in a distal portion (B84C) of the staple cartridge have first distal projection configurations that have a first distal height that is greater than a second distal height of each of the second distal projection configurations associated with all of, or at least a plurality of the second distal staple cavities in the distal portion (B84C). The third distal projection configurations associated with all of, or at least a plurality of the third distal staple cavities in the distal portion (B84C) of the cartridge have a third distal height that is less than the second distal height. Thus, in one arrangement, the heights of the projection configurations closest to the longitudinal slot are the highest and decrease in magnitude with each subsequent row laterally. In another arrangement, although the heights of the projection configurations may decrease in subsequent lateral rows going laterally away from the longitudinal slot, each projection configuration in a single row may have the same height. In other arrangements, the proximal height is greater than the middle height, which is greater than the distal height of the projection configurations in each single row. Such arrangements serve to improve the gripping and retention characteristics of the staple cartridge in areas wherein the adjacent article (tissue and/or adjunct) encounters more forces/stress during firing—adjacent the longitudinal slot as well as adjacent the proximal end of the cartridge.

As used herein, the term "projection configuration" encompasses one or more of the following characteristics: projection height, width, thickness, compositions, and overall geometry and shape. In addition to the heights of the projections varying along a cartridge body, overall geometries of the projections can vary based on a specific location of a projection on the cartridge body. For example, it is preferable for projections extending from a distal portion of the cartridge body to have a smooth, or rounded profile so as to prevent damaging an adjacent article as jaws of the end effector capture the adjacent article therebetween. Furthermore, it is preferable for projections extending from a proximal portion of the cartridge body to have a profile that causes snagging and/or friction of the adjacent article to optimize retaining the adjacent article in position. Those of ordinary skill in the art will appreciate that the staple cavities of the various surgical staple cartridges herein are configured to removably support/store therein a corresponding surgical staple or fastener therein.

In this arrangement, first projections (B84310a) are associated with each of the proximal cavities (B84210a) in the proximal segment, second projections (B84310b) are associated with each of the middle cavities (B84210b) in the middle segment, and third projections (B84310c) are associated with each of the distal cavities (B84210c) in the distal segment in the manner described herein. Other arrangements are contemplated wherein the first projections (B84310a) are not associated with all of the proximal cavities (B84210a) and/or the second projections (B84310b) are not associated with all of the middle cavities (B84210b) and/or the third projections (B84310c) are not associated with all of the distal cavities (B84210c).

Likewise, first projections (B84320a) are associated with each of the second proximal cavities (B84220a) in the proximal segment, second projections (B84320b) are associated with each of the second middle cavities (B84220b) in the middle segment, and third projections (B84320c) are associated with each of the second middle cavities (B84220c) in the distal segment in the manner described herein. Other arrangements are contemplated wherein the first projections (B84320a) are not associated with all of the second proximal cavities (B84220a) and/or the second projections (B84320b) are not associated with all of the second middle cavities (B84220b) and/or the third projections (B84320c) are not associated with all of the second distal cavities (B84220c). Further to the above, first projections (B84330a) are associated with each of the third proximal cavities (B84230a) in the proximal segment, second projections (B84330b) are associated with each of the third middle cavities (B84230b) in the middle segment, and third projections (B84330c) are associated with each of the third distal cavities (B84230c) in the distal segment in the manner described herein. Other arrangements are contemplated wherein the first projections (B84330a) are not associated with all of the third proximal cavities (B84230a) and/or the second projections (B84330b) are not associated with all of the third middle cavities (B84230b) and/or the third projections (B84330c) are not associated with all of the third distal cavities (B84230c).

In one arrangement, the number of proximal cavities (B84210a) in the proximal segment of the first longitudinal row (B84210) is equal to the number of middle cavities (B84210b) in the middle segment of the first longitudinal row (B84210), and the number of distal cavities (B84210c) in the distal segment of the first longitudinal row (B84210), respectively. Similarly, the number of second proximal cavities (B84220a) in the proximal segment of the second longitudinal row (B84220) is equal to the number of second middle cavities (B84220b) in the middle segment of the second longitudinal row (B84220), and the number of second distal cavities (B84220c) in the distal segment of the second longitudinal row (B84220), respectively. Also in this arrangement, the number of third proximal cavities (B84230a) in the proximal segment of the third longitudinal row (B84230) is equal to the number of third middle cavities (B84230b) in the middle segment of the third longitudinal row (B84230), and the number of third distal cavities (B84230c) in the distal segment of the third longitudinal row (B84210), respectively. The number of cavities in the first longitudinal row (B84210) may be the same as the number of cavities in the second longitudinal row (B84220) and the number of cavities third longitudinal row (B84230), or they may be different.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (B110) comprising: (a) a cartridge body (B114, B114a-b, B214); (b) a deck (B124, B124a-b, B224) defined by the cartridge body (B114, B114a-b, B214), wherein the deck (B124, B124a-c, B224) is configured to compress tissue (T) against an anvil (44) of a surgical stapler (10); (c) an elongate slot (B126, B226) formed in the deck (B124, B124a-b, B224), wherein the elongate slot (B126, B226) is configured to slidably receive a knife (50) progressively and longitudinally relative to the deck (B124a-b, B224) therein; (d) a plurality of pockets (B128, B228) formed in the deck (B124, B124a-b, B224), the plurality of pockets (B128, B228) configured to house a plurality of staples (B116), wherein the plurality of pockets (B128, B228) includes first and second pockets (B128, B228), each of the first and second pockets (B128, B228) comprising: (i) a first longitudinal end (B166, B266), (ii) a second longitudinal end (B168, B268) disposed opposite the first longitudinal end (B166, B266), (iii) a first lateral side (B170, B270) disposed between the first and second longitudinal ends (B166, B168, B266, B268), and (iv) a second lateral side (B172, B272) disposed between the first and second longitudinal ends (B166, B168, B266, B268) and opposite to the first lateral side (B170, B270); and (e) a plurality of engagement protrusions (B130a-f, B130h-i, B230a-1) extending from the deck (B124, B124a-b, B224) and configured to grip tissue (T) or an adjunct material (B188), the plurality of engagement protrusions (B130a-f, B130h-i, B230a-1) comprising: (i) a first engagement protrusion (B130a, B130e, B230a, B230h) associated with the first pocket (B128, B228), wherein the first engagement protrusion (B130a, B130e, B230a, B230h) includes a lateral portion (B186, B187, B286, B287) extending longitudinally along the first lateral side (B170, B270) of the first pocket (B128, B228) parallel to a longitudinal axis (BLA) of the cartridge body (B114, B114a-b, B214), wherein the lateral portion (B186, B187, B286, B287) is recessed relative to at least a portion of the first engagement protrusion (B130a, B130e, B230a, B230h), wherein the first engagement protrusion (B130a, B130e, B230a, B230h) does not extend along the second lateral side (B172, B272) of the first pocket (B128, B228) such that the second lateral side (B172, B272) opens directly to the deck (B124, B124a-b, B224), and (ii) a second engagement protrusion (B130b, B130d, B130h-i, B230b, B230g) associated with the second pocket (B128, B228).

Example 2

The apparatus (B110) of Example 1, wherein the second engagement protrusion (B130b, B130d, B130h-i, B230b, B230g) includes a lateral portion (B180, B181, B183, B189, B192, B280, B289) extending longitudinally along the second lateral side (B172, B272) of the second pocket (B128, B228).

Example 3

The apparatus (B110) of Example 2, wherein the second engagement protrusion (B130b, B130d, B230b, B230g) does not extend along the first lateral side (B170, B270) of the second pocket (B128, B228) such that the first lateral side (B170, B270) opens directly to the deck (B124, B124*a-b*, B224).

Example 4

The apparatus (B110) of any of Example 1 through 3, wherein the first and second lateral sides (B170, B172, B270, B272) of the first pocket (B128, B228) extend substantially parallel to the elongate slot (B126, B226).

Example 5

The apparatus (B110) of any of Examples 1 through 4, wherein the plurality of engagement protrusions (B130*a-f*, B130*h-i*, B230*a-1*) are arranged into at least first and second rows (B150, B152, B250, B252), wherein the first row (B150, B250) is positioned closer to the elongate slot (B126, B226) than the second row (B152, B252), wherein the first row (B150, B250) defines a length (BL), wherein the lateral portion (B180, B186, B280, B286) alternates between longitudinally adjacent pockets (B128, B228) along the length (BL) of the first row (B150, B250).

Example 6

The apparatus (B110) of Example 5, wherein longitudinally adjacent engagement protrusions (B130*f*, B230*c-d*, B230*i-j*) of the second row (B152, B252) are not linked together using an interconnection (B160, B260) extending from the deck (B124, B124*a-b*, B224), wherein the first row (B150, B250) is substantially parallel to the elongate slot (B126, B226).

Example 7

The apparatus (B110) of any of Examples 2 through 6, (i) the first engagement protrusion (B130*a*, B130*e*, B230*a*, B230*h*) comprising: (A) a first end portion (B176, B276) that wraps around the first longitudinal end (B166, B266) of the first pocket (B128, B228), (B) a second end portion (B178, B278) that wraps around the second longitudinal end (B168, B268) of the first pocket (B128, B228), and (C) the lateral portion (B186, B187, B286, B287) extending between the first and second end portions (B176, B178, B276, B278) of the first engagement protrusion (B186, B187, B286, B287), and (ii) the second engagement protrusion (B130*b*, B130*d*, B130*h-i*, B230*b*, B230*g-h*) comprising: (A) a first end portion (B176, B276) that wraps around the first longitudinal end (B166, B266) of the second pocket (B128, B228), (B) a second end portion (B178, B278) that wraps around the second longitudinal end (B168, B268) of the second pocket (B128, B228), and (C) the lateral portion (B180, B181, B183, B189, B192, B280, B286, B289) extending between the first and second end portions (B176, B178, B276, B278) of the second engagement protrusion (B130*b*, B130*d*, B130*h-i*, B230*b*, B230*g-h*).

Example 8

The apparatus (B110) of Example 7, further comprising an interconnection (B160, B260) extending between the second end portion (B178, B278) of first engagement protrusion (B130*a*, B130*e*, B230*a*, B230*h*) and the first end portion (B176, B276) of the second engagement protrusion (B130*d*, B230*g*).

Example 9

The apparatus (B110) of Example 8, wherein the first and second end portions (B176, B178, B276, B278) of the first engagement protrusion (B130*a*, B130*e*, B230*a*, B230*h*) extend from the deck (B124, B124*a-b*, B224) a first maximum height (Bhep, Bhep1), wherein the interconnection (B160, B260) extends from the deck (B124, B124*a-b*, B224) a second maximum height (Bhi), wherein the first maximum height (Bhep, Bhep1) is greater than the second maximum height (Bhi).

Example 10

The apparatus (B110) of any of Examples 7 through 9, wherein the first and second end portions (B176, B178, B276, B278) of the first engagement protrusion (B130*a*, B130*e*, B230*a*, B230*h*) extend from the deck (B124, B124*a-b*, B224) a first maximum height (Bhep, Bhep1), wherein the lateral portion (B186, B187, B286, B287) of the first engagement protrusion (B130*a*, B130*e*, B230*a*, B230*h*) extends from the deck (B124, B124*a-b*, B224) a second maximum height (Bhlp), wherein the first maximum height (Bhep, Bhep1) is greater than the second maximum height (Bhlp).

Example 11

The apparatus (B110) of Example 10, wherein the first maximum height (Bhep, Bhep1) is about double the second maximum height (Bhlp).

Example 12

The apparatus (B110) of any of Examples 1 through 3 and Examples 5 through 11, wherein the plurality of pockets (B128, B228) are arranged into at least first and second rows (B144, B146, B244, B246), wherein the first row (B144, B244) is positioned closer to the elongate slot (B126, B226) than the second row (B146, B246), wherein the first and second pockets (B128, B228) arranged in the first row (B144, B244).

Example 13

The apparatus (B110) of any of Examples 5 through 6 or Example 12, wherein the plurality of engagement protrusions (B130*a-f*, B130*h-i*, B230*a-1*) include a first row (B150, B150*a-b*, B250) of engagement protrusions associated with the first row (B144, B244) of the pockets (B128, B228).

Example 14

The apparatus (B110) of any of Examples 1 through 13, wherein each engagement protrusion (B130*a-b*, B130*d-e*, B130*h-i*, B230*a-b*, B230*g-h*) of the first row (B150, B150*a-b*, B250) of engagement protrusions at least partially surrounds a respective pocket (B128, B228) of the first row (B144, B244) of pockets.

Example 15

The apparatus (B110) of any of Examples 1 through 14, wherein the deck (B124, B124*a-b*) is substantially planar.

Example 16

An apparatus (B110) comprising: (a) a cartridge body (B114, B114*a-b*, B214) that extends along a longitudinal axis (BLA); (b) a deck (B124, B124*a-b*, B224) defined by the cartridge body (B114, B114*a-b*, B214), wherein the deck (B124, B124*a-b*, B224) is configured to compress tissue (T) against an anvil (44) of a surgical stapler (10); (c) an elongate slot (B126, B226) formed in the deck (B124, B124*a-b*, B224), wherein the elongate slot (B126, B226) is configured to slidably receive a knife (50) progressively and longitudinally relative to the deck (B124, B124*a-b*, B224) therethrough; (d) a plurality of pockets (B128, B228) formed in the deck (B124, B124*a-b*, B224), the plurality of pockets (B128, B228) configured to house a plurality of staples (B116), wherein the plurality of pockets (B128, B228) includes first and second pockets (B128, B228); (e) a plurality of engagement protrusions (B130*a-f*, B130*h-i*, B230*a*-1) extending from the deck (B124, B124*a-b*, B224) and configured to grip tissue (T) or an adjunct material (B188), the plurality of engagement protrusions (B130*a-f*, B130*h-i*, B230*a*-1) comprising: (i) a first engagement protrusion (B130*a*, B130*e*, B230*a*, B230*h*) associated with the first pocket (B128, B228), wherein the first engagement protrusion (B130*a*, B130*e*, B230*a*, B230*h*) has a first maximum width (BWp) in a direction transverse to the longitudinal axis (BLA), wherein the first engagement protrusion (B130*a*, B130*e*, B230*a*, B230*h*) includes a lateral portion (B186, B187, B286, B287) extending longitudinally along a first lateral side (B170, B270) of the first pocket (B128, B228), wherein the first engagement protrusion (B130*a*, B130*e*, B230*a*, B230*h*) does not extend along a second lateral side (B172, B272) of the first pocket (B128, B228) such that the second lateral side (B172, B272) opens directly to the deck (B124, B124*a-b*, B224), and (ii) a second engagement protrusion (B130*a-b*, B130*d-e*, B130*h-i*, B230*a-b*, B230*g-h*) associated with the second pocket (B128, B228); and (f) an interconnection (B160, B260) extending between the first and second engagement protrusions (B130*a-b*, B130*d-e*, B130*h-i*, B230*a-b*, B230*g-h*), wherein the interconnection (B160, B260) has a second maximum width (BWi) in the direction transverse to the longitudinal axis (BLA), wherein the first maximum width (BWp) is greater than the second maximum width (BWi).

Example 17

The apparatus (B110) of Example 16, wherein a third maximum width (BWc) is defined by a distance between the first and second lateral sides (B170, B172, B270, B272) of the first pocket (B128, B228) in the direction transverse to the longitudinal axis (BLA), wherein the third maximum width (BWc) is greater than the second maximum width (BWi).

Example 18

The apparatus (B110) of any of Examples 16 through 17, (i) the first pocket (B128, B228) comprising: (i) a first longitudinal end (B166, B266), (ii) a second longitudinal end (B168, B168) disposed opposite the first longitudinal end (B166, B266), wherein the first lateral side (B170, B270) is disposed between the first and second longitudinal ends (B166, B168, B266, B268), wherein the second lateral side (B172, B272) is disposed between the first and second ends (B166, B168) and opposite to the first lateral side (B170, B270), (ii) the second pocket (B128, B228) comprising: (i) a first longitudinal end (B166, B266), (ii) a second longitudinal end (B168, B268) disposed opposite the first longitudinal end (B166, B266), (iii) a first lateral side (B170, B270) disposed between the first and second longitudinal ends (B166, B168, B266, B268), and (iv) a second lateral side (B172, B272) disposed between the first and second longitudinal ends (B166, B168, B266, B268) and opposite to the first lateral side (B170, B270), (iii) the first engagement protrusion (B130*a*, B130*e*, B230*a*, B230*h*) further comprising: (A) a first end portion (B176, B276) that wraps around the first longitudinal end (B166, B266) of the first pocket (B128, B228), and (B) a second end portion (B178, B278) that wraps around the second longitudinal end (B168, B268) of the first pocket (B128, B228), and (iv) the second engagement protrusion (B130*d-e*, B230*g-h*) further comprising: (A) a first end portion (B176, B276) that wraps around a first longitudinal end (B166, B266) of the second pocket (B128, B228), and (B) a second end portion (B178, B278) that wraps around a second longitudinal end (B168, B268) of the second pocket (B128, B228), wherein the interconnection (B160, B260) extends between the second end portion (B178, B278) of first engagement protrusion (B130*a*, B130*e*, B230*a*, B230*h*) and the first end portion (B176, B276) of the second engagement protrusion (B130*d-e*, B230*g-h*).

Example 19

The apparatus (B110) of Example 18, wherein the second engagement protrusion (B130*d-e*, B230*g-h*) further comprises a lateral portion (B180, B186, B280, B286) extending between the first and second end portions (B176, B178, B276, B278) of the second engagement protrusion (B130*d-e*, B230*g-h*) on at least one of the first or second lateral sides (B170, B172, B270, B272) of the second pocket (B128, B228, B528, B628).

Example 20

The apparatus (B110) of Example 19, wherein the lateral portion (B186, B286) of the second engagement protrusion (B130*e*, B230*h*) extends on the first lateral side (B170, B270) of the second pocket (B128, B228), wherein the second engagement protrusion (B130*e*, B230*h*) does not extend longitudinally along the second lateral side (B172, B272) of the second pocket (B128, B228) such that the second lateral side (B172, B272) opens directly to the deck (B124, B124*a-b*, B224).

Example 21

The apparatus (B110) of Example 19, wherein the lateral portion (B180, B280) of the second engagement protrusion (B130*d*, B230*g*) extends on the second lateral side (B172, B272) of the second pocket (B128, B228), wherein the second engagement protrusion (B130*d*, B230*g*) does not extend longitudinally along the first lateral side (B170, B270) of the second pocket (B128, B228) such that the first lateral side (B170, B270) opens directly to the deck (B124, B124*a-b*, B224).

Example 22

The apparatus (B110) of Example 19, wherein the lateral portion (B192) of the second engagement protrusion (B130*g*) extends on both of the first and second lateral sides (B170, B172) of the second pocket (B128).

Example 23

The apparatus (B110) of any of Examples 18 through 22, wherein the first engagement protrusion (B130*a*, B130*e*, B230a, B230h) has a first maximum width (BWp) in a direction transverse to the longitudinal axis (BLA), wherein the interconnection (B160, B260) has a second maximum width (BWi) in the direction transverse to the longitudinal axis (BLA), wherein the first maximum width (BWp) is greater than the second maximum width (BWi).

Example 24

The apparatus (B110) of any of Examples 18 through 23, wherein the first and second end portions (B176, B178, B276, B278) of the first engagement protrusion (B130a, B130e, B230a, B230h) extend from the deck (B124, B124a-b, B224) a first maximum height (Bhep), wherein the interconnection (B160, B260) extends from the deck (B124, B124a-b, B224) a second maximum height (Bhi), wherein the first maximum height (Bhep) is greater than the second maximum height (Bhi).

Example 25

The apparatus (B110) of any of Examples 16 through 24, wherein the plurality of engagement protrusions (B130a-f, B130h-i, B230a-1) are arranged into at least first and second rows (B150, B150a-b, B152, B250, B252), wherein the first row (B150, B150a-b) is positioned closer to the elongate slot (B126, B226) than the second row (B152, B154, B252, B254), wherein the first and second engagement protrusions (B130a-b, B130d-e, B230a-b, B230g-h) are arranged in the first row (B150, B150a-b) and are connected by the interconnection (B160, B260).

Example 26

The apparatus (B110) of Example 25, wherein each longitudinally adjacent engagement protrusion (B130a-b, B130d-e, B230a-b, B230g-h) of the first row (B150, B150a-b) is linked together by an interconnection (B160, B260).

Example 27

The apparatus (B110) of any of Examples 25 through 26, wherein no longitudinally adjacent engagement protrusion (B130f, B230e-f, B230k-1) of the second row (B152, B252) is linked together by an interconnection (B160, B260).

Example 28

The apparatus (B110) of any of Examples 16 through 27, wherein the plurality of engagement protrusions (B130a-f, B130h-i, B230a-1) are symmetric about the elongate slot (B126, B226).

Example 29

The apparatus (B110) of any of Examples 16 through 28, wherein the deck (B124, B124a-b) is substantially planar, wherein the interconnection (B160) extends from the deck (B124, B124a-b) and terminates at a planar surface (B184c-d) that is parallel to the deck (B124, B124a-b).

Example 30

The apparatus (B110) of any of Examples 16 through 29, further comprising a plurality of staple drivers (B118), wherein each staple driver (B118) of the plurality of staple drivers (B118) is aligned with and movable vertically within a respective pocket (B128, B228) of the plurality of pockets (B128, B228) for actuating the respective staple (B116) into the tissue (T).

Example 31

An apparatus (B110) comprising: (a) a cartridge body (B514, B514a, B614, B614a) that extends longitudinally; (b) a deck (B524, B524a, B624, B624a) defined by the cartridge body (B514, B514a, B614, B614a), wherein the deck (B524, B524a, B624, B624a) is configured to compress tissue (T) against an anvil (44) of a surgical stapler (10); (c) an elongate slot (B526, B626) formed in the deck (B524, B524a, B624, B624a), wherein the elongate slot (B526, B626) is configured to slidably receive a knife (50) progressively and longitudinally relative to the deck (B524, B524a, B624, B624a) therethrough; (d) a plurality of pockets (B528, B628) formed in the deck (B524, B524a, B624, B624a) and configured to house a plurality of staples (B116); (e) an array (B529, B529a, B629, B629a) of engagement protrusions extending from the deck (B524, B524a, B624, B624a) and configured to grip tissue (T) or an adjunct material (B188), wherein each of the engagement protrusions (B530b-d, B630a-e) is associated with a respective one of the plurality of pockets (B528, B628), wherein the array (B529, B529a, B629, B629a) of engagement protrusions includes a first portion (B592, B592a, B596, B596a, B684, B684a, B692, B692a, B696, B696a) of longitudinally adjacent engagement protrusions and a second portion (B594, B594a, B598, B598a, B688, B688a, B694, B694a, B698, B698a) of longitudinally adjacent engagement protrusions, wherein the first and second portions (B592, B592a, B594, B594a, B596, B596a, B598, B598a, B684, B684a, B688, B688a, B692, B692a, B694, B694a, B696, B696a, B698, B698a) are arranged within a single longitudinal row (B552, B552a, B554, B554a, B650, B650a, B652, B652a, B654, B654a); and (f) a plurality of interconnections (B560, B660) extending from the deck (B524, B524a, B624, B624a) and linking together longitudinally adjacent engagement protrusions (B530c, B630b-d) of the first portion (B592, B592a, B596, B596a, B684, B684a, B692, B692a, B696, B696a) but not linking together longitudinally adjacent engagement protrusions (B530b, B530d, B630a-b) of the second portion (B594, B594a, B598, B598a, B688, B688a, B694, B694a, B698, B698a).

Example 32

The apparatus (B110) of Example 31, wherein the array (B529, B529a, B629, B629a) of engagement protrusions is arranged into at least first and second rows (B550, B550a, B552, B552a, B554, B554a, B650, B650a, B652, B652a, B654, B654a), wherein the first row (B550, B550a, B650, B650a) is positioned closer to the elongate slot (B526, B626) than the second row (B552, B552a, B554, B554a, B652, B652a, B654, B654a).

Example 33

The apparatus (B110) of Example 32, wherein the second row (B552, B552a, B554, B554a, B652, B652a, B654, B654a) includes the first and second portions (B592, B592a, B594, B594a, B596, B596a, B598, B598a, B692, B692a, B694, B694a, B696, B696a, B698, B698a), wherein the first portion (B592, B592a, B596, B596a, B692, B692a, B696, B696a) of longitudinally adjacent engagement protrusions of the second row (B552, B552a, B554, B554a, B652, B652a, B654, B654a) are linked together using interconnections (B560, B660) extending from the deck (B524, B524a, B624, B624a), wherein the second portion (B594, B594a, B598, B598a, B694, B694a, B698, B698a) of longitudinally adjacent engagement protrusions of the second row (B552, B552a, B554, B554a, B652, B652a, B654, B654a) are not linked together.

Example 34

The apparatus (B110) of Example 33, wherein the second portion (B594, B594a, B598, B598a, B694, B698) of longitudinally adjacent engagement protrusions of the second row (B552, B552a, B554, B554a, B652, B654) is disposed distal relative to the first portion (B592, B592a, B596, B596a, B692, B696) of longitudinally adjacent engagement protrusions of the second row (B552, B552a, B554, B554a, B652, B654).

Example 35

The apparatus (B110) of Example 33, wherein the second portion (B694a, B698a) of longitudinally adjacent engagement protrusions of the second row (B652a, B654a) is disposed proximal relative to the first portion (B692a, B696a) of longitudinally adjacent engagement protrusions of the second row (B652a, B654a).

Example 36

The apparatus (B110) of any of Examples 33 through 35, wherein the first portion (B596a, B692, B692a, B696, B696a) comprises about half of the second row (B552, B552a, B554, B554a, B652, B652a, B654, B654a) and the second portion (B598a, B694, B694a, B698, B698a) comprises about half of the second row (B554a, B652, B652a, B654, B654a).

Example 37

The apparatus (B110) of any of Examples 32 through 35, wherein the first portion (B592a) comprises about three quarters of the second row (B552) and the second portion (B594a) comprises about one quarter of the second row (B552).

Example 38

The apparatus (B110) of any of Examples 32 through 38, wherein each longitudinally adjacent engagement protrusion (B530a, B530c) of the first row (B550, B550a) is linked together using an interconnection (B560) extending from the deck (B524, B524a).

Example 39

The apparatus (B110) of any of Examples 32 through 38, wherein each engagement protrusion (B530a, B530c) of the first row (B550, B550a) of engagement protrusions completely surrounds a respective pocket (B528) of the first row (B544) of pockets.

Example 40

The apparatus (B110) of any of Examples 32 through 39, wherein the first and second rows (B550, B550a, B552, B552a, B554, B554a, B650, B650a, B652, B652a, B654, B654a) are not connected together by a feature extending from the deck (B524, B524a, B624, B624a).

Example 41

The apparatus (B110) of any of Examples 32 through 40, the first portion (B592, B592a, B596, B596a, B684, B684a, B692, B692a, B696, B696a) of the longitudinally adjacent engagement protrusions (B530c, B630c-d) of the second row (B552, B552a, B652, B652a, B654, B654a) comprising: (A) a first end portion (B576, B676) that wraps around a first longitudinal end (B566, B666) of a pocket (B528, B628) of the plurality of pockets (B528, B628), (B) a second end portion (B578, B678) that wraps around a second longitudinal end (B568, B668) of the pocket (B528, B628), and (C) a lateral portion (B580, B680) extending between the first and second end portion (B576, B578, B576, B678) of the engagement protrusion (B530c, B630c-d) on at least one of first or second lateral sides (B570, B572, B670, B672) of the pocket (B528, B628).

Example 42

The apparatus (B110) of Example 41, wherein an interconnection (B560, B660) of the plurality of the interconnections (B560, B660) extends between the second end portion (B578, B678) of a first engagement protrusion (B530a, B530c, B630c-d) of the longitudinally adjacent engagement protrusions (B530a, B530c, B630c-d) and the first end portion (B576, B676) of a second engagement protrusion (B530c, B630c-d) of the longitudinally adjacent engagement protrusions (B530a, B530c, B630c-d).

Example 43

The apparatus (B110) of any of Examples 41 through 42, wherein the lateral portion (B580, B680) extends on both of the first and second lateral sides (B570, B572, B670, B672) of the pocket (B528, B628).

Example 44

The apparatus (B110) of any of Examples 32 through 43, further comprising a third row (B554, B554a, B654, B654a) of engagement protrusions disposed further from the elongate slot (B526, B626) than either of the first and second rows (B550, B550a, B552, B552a, B650, B650a, B652, B652a) of engagement protrusions, wherein a first portion (B596, B596a, B696, B696a) of longitudinally adjacent engagement protrusions of the third row (B554, B554a, B654, B654a) are linked together using interconnections (B560, B660) extending from the deck (B524, B524a, B624, B624a), wherein a second portion (B598, B598a, B698, B698a) of longitudinally adjacent engagement protrusions of the third row (B554, B554a, B654, B654a) are not linked together.

Example 45

The apparatus (B110) of Example 44, wherein a first percentage of longitudinally adjacent engagement protrusions (B530c, B630c-d) are linked together using the interconnection (B560, B660) extending from the deck (B524, B524a, B624, B624a) in the second row (B552, B552a, B652, B652a), wherein a second percentage of longitudinally adjacent engagement protrusions are linked together using interconnections (B560, B660) extending from the deck (B524, B524a, B624, B624a) in the third row (B554, B554a, B654, B654a), wherein the first percentage is greater than the second percentage.

Example 46

An apparatus (B110) comprising: (a) a cartridge body (B114, B114a-c, B214, B514, B514a); (b) a deck (B124, B124a-c, B224, B524, B524a) defined by the cartridge body (B114, B114a-c, B214, B514, B514a), wherein the deck (B124, B124a-c, B224, B524, B524a) is configured to compress tissue (T) against an anvil (44) of a surgical stapler (10); (c) an elongate slot (B126, B226, B526, B626) formed in the deck (B124, B124a-c, B224, B524, B524a), wherein the elongate slot (B126, B226, B526) is configured to slidably receive a knife (50) progressively and longitudinally relative to the deck (B124, B124a-c, B224, B524, B524a) therethrough; (d) a plurality of pockets (B128, B228, B528) formed in the deck (B124, B124a-c, B224, B524, B524a), wherein the pockets (B128, B228, B528) are configured to house a plurality of staples (B116), wherein the pockets (B128, B228, B528) include first and second pockets (B128, B228, B528) arranged in a first row (B144, B244, B544), wherein the first row (B144, B244, B544) defines a length (BL); (e) a plurality of engagement protrusions (B130a-i, B230a-1, B530a-d) extending from the deck (B124, B124a-c, B224, B524, B524a), wherein the engagement protrusions (B130a-I, B230a-1, B530a-d) are configured to grip tissue (T) or an adjunct material (B188), wherein the engagement protrusions (B130a-b, B130d-e, B130g-I, B230a-b, B230g-h, B530a, B530c) are arranged into at least a first row (B150, B150a-c, B250, B550, B550a), wherein each engagement protrusion (B130a-b, B130d-e, B130g-I, B230a-b, B230g-h, B530a, B530c) of the first row (B150, B150a-c, B250, B550) of engagement protrusions is associated with a respective pocket (B128, B228, B528) of the first row (B144, B244, B544) of pockets; and (f) a plurality of interconnections (B160, B260, B560) extending from the deck (B124, B124a-c, B224, B524, B524a) and linking together longitudinally adjacent engagement protrusions (B130a-b, B130d-e, B130g-I, B230a-b, B230g-h, B530a, B530c) of the first row (B150, B150a-c, B250, B550) of engagement protrusions (B130a-I, B230a-1, B530a-d), wherein the engagement protrusions (B130a-I, B230a-1, B530a-d) of the first row (B150, B150a-c, B250, B550) and the interconnections (B160, B260, 360, 460, B560) collectively form a continuous non-linear raised cross-sectional area (B162, B162a-c, B164, B164a-c, B262, B264, B562, B562a, B564, B564a) extending from the deck (B124, B124a-c, B224, B524, B524a) along the length (BL) of the first row (B144, B244, B544) of pockets.

Example 47

The apparatus (B110) of Example 46, wherein the continuous non-linear raised cross-sectional area (B162, B162a-c, B164, B164a-c, B262, B264, B562, B562a, B564, B564a) has a non-uniform width.

Example 48

The apparatus (B110) of any of Examples 46 through 47, wherein the continuous non-linear raised cross-sectional area (B162, B162a-c, B164, B164a-c, B262, B264, B562, B562a, B564, B564a) is configured to provide increased stiffness to the first row (B150, B150a-c, B250, B550, B550a) of engagement protrusions.

Example 49

The apparatus (B110) of any of Examples 46 through 48, wherein the first row (B150, B150a-c, B250, B550, B550a) of engagement protrusions extend from the deck (B124, B124a-c, B224, B524, B524a) a first maximum height (Bhep), wherein the interconnection (B160, B260, B560) extends from the deck (B124, B124a-c, B224, B524, B524a) a second maximum height (Bhi), wherein the first maximum height (Bhep) is greater than the second maximum height (Bhi).

Example 50

The apparatus (B110) of any of Examples 46 through 49, wherein each engagement protrusion (B130a-b, B130d-e, B130g-I, B230a, B230g-h, B530a, B530c) of the first row (B150, B150a-c, B250, B550, B550a) of engagement protrusions surrounds a respective pocket (B128, B228, B528) of the first row (B144, B244, B544) of pockets.

Example 51

The apparatus (B110) of any of Examples 46 through 50, wherein the plurality of pockets (B128, B228, B528) further comprises a second row (B144, B244, B544) of pockets, wherein the plurality of engagement protrusions further comprises a second row (B150, B150a-c, B250, B550, B550a) of engagement protrusions, the apparatus (B110) further comprising a plurality of interconnections (B160, B260, B560) extending from the deck (B124, B124a-c, B224, B524, B524a) and linking together longitudinally adjacent engagement protrusions (B130a-I, B230a-1, B530a-d) of the second row (B150, B150a-c, B250, B550), wherein each engagement protrusion (B130a-b, B130d-e, B130g-I, B230a-b, B230g-h, B530a, B530c) of the second row (B150, B150a-c, B250, B550, B550a) of engagement protrusions is associated with a respective pocket (B128, B228, B528) of the second row (B144, B244, B544) of pockets, wherein the second row (B144, B244, B544) of pockets defines a length (BL), wherein the engagement protrusions (B130a-b, B130d-e, B130g-I, B230a-b, B230g-h, B530a, B530c) of the second row (B150, B150a-c, B250, B550, B550a) form a continuous non-linear raised cross-sectional area (B162, B162a-c, B164, B164a-c, B262, B264, B562, B562a, B564, B564a) extending from the deck (B124, B124a-c, B224, B524, B524a) along the length (BL) of the second row (B144, B244, B544) of pockets.

Example 52

The apparatus (B110) of Example 51, wherein the first row (B144, B244, B544) of pockets is disposed across the elongate slot (B126, B226, B526) from the second row (B144, B244, B544) of pockets.

Example 53

The apparatus (B110) of any of Examples 51 through 52, wherein the first and second rows (B144, B244, B544) of pockets include the closest pockets (B128, B228, B528) to the elongate slot (B126, B226, B526).

Example 54

The apparatus (B110) of any of Examples 51 through 53, wherein the first and second rows (B144, B244, B544) of engagement protrusions are symmetric about the elongate slot (B126, B226, B526).

Example 55

The apparatus (B110) of any of Examples 51 through 54, wherein the plurality of pockets (B128, B228, B528) further comprises a third row (B146, B148, B246, B248, B546, B548) of pockets positioned further from the elongate slot (B126, B226, B526) than the first and second pockets (B128, B228, B528), wherein the plurality of engagement protrusions (B130a-I, B230a-1, B530a-d) further comprises a third row (B152, B154, B252, B254, B552, B554, B552a, B554a) of engagement protrusions that do not form a continuous non-linear raised cross-sectional area extending from the deck (B124, B124a-c, B224, B524, B524a) along the length of the third row (B146, B148, B246, B248, B546, B548) of pockets.

Example 56

The apparatus (B110) of any of Examples 46 through 55, wherein the first row (B150, B150a-c, B250, B550, B550a) of engagement protrusions includes a first engagement protrusion (B130a-b, B130d-e, B130g-I, B230a, B230g-h, B530a, B530c) comprising: (A) a first end portion (B176, B276, B576) that wraps around a first longitudinal end (B166, B266, B566) of the first pocket (B128, B228, B528), (B) a second end portion (B178, B278, B578) that wraps around a second longitudinal end (B166, B266, B566) of the first pocket (B128, B228, B528), and (C) a lateral portion (B180, B181, B183, B186, B187, B189, B192, B280, B286, B287, B289, B580) extending between the first and second end portions (B178, B278, B578) of the first engagement protrusion (B130a-b, B130d-e, B130g-I, B230a, B230g-h, B530a, B530c) on at least one of first or second lateral sides (B170, B172, B270, B272, B570, B572) of the first pocket (B128, B228, B528).

Example 57

The apparatus (B110) of Example 56, wherein the first engagement protrusion (B130a-b, B130d-e, B130g-I, B230a, B230g-h, B530a, B530c) has a first maximum width (BWp) in a direction transverse to a longitudinal axis (BLA) of the cartridge body (B114, B114a-c, B214, B514, B514a), wherein the interconnections (B160, B260, B560) have a second maximum width (Bwi) in the direction transverse to the longitudinal axis (BLA), wherein the first maximum width (BWp) is greater than the second maximum width (Bwi).

Example 58

The apparatus (B110) of any of Examples 56 through 57, wherein the lateral portion (B186, B187, B286, B287) of the first engagement protrusion (B130a, B130e, B230a, B230h) extends on the first lateral side (B170, B270) of the first pocket (B128, B228), wherein the first engagement protrusion (B130a, B130e, B230a, B230h) does not extend longitudinally along the second lateral side (B172, B272) of the first pocket (B128, B228) such that the second lateral side (B172, B272) opens directly to the deck (B124, B124a-b, B224).

Example 59

The apparatus (B110) of any of Examples 56 through 57, wherein the lateral portion (B180, B189, B280, B289) of the first engagement protrusion (B130b, B130d, B230b, B230g) extends on the second lateral side (B172, B272) of the first pocket (B128, B228), wherein the first engagement protrusion (B130b, B130d, B230b, B230g) does not extend longitudinally along the first lateral side (B170, B270) of the first pocket (B128, B228) such that the first lateral side (B170, B270) opens directly to the deck (B124, B124a-b, B224).

Example 60

The apparatus (B110) of any of Examples 56 through 57, wherein the lateral portion (B192, B680) of the first engagement protrusion (B130g, B230g, B530a, B530c) extends on both of the first and second lateral sides (B170, B172, B270, B272, B570, B572) of the first pocket (B128, B228, B528).

Example 61

A surgical staple cartridge (B80000, B81000, B82000, B83000, B84000), comprising: (a) a cartridge body (B80100, B82100, B83100, B84100) comprising a deck (B80106, B81106, B82106, B83106, B84106); (b) a plurality of staple cavities in said cartridge body, wherein said plurality of staple cavities comprises: (i) a first staple cavity (B82210a, B84210a) defined in said cartridge body, wherein each first staple cavity comprises a first projection configuration (B82211a, B84210a); (ii) a second staple cavity (B82210b, B84210b) defined in said cartridge body, wherein said second staple cavity is distal to said first staple cavity and comprises a second projection configuration (B82211b, B84211b); and (iii) a third staple cavity (B82210c, B84210c) defined in said cartridge body, wherein said third staple cavity is distal to said second staple cavity and comprises a third projection configuration (B82211c, B84211c), wherein said second projection configuration differs from said first projection configuration, and wherein said third projection configuration differs from said second projection configuration and said first projection configuration; (c) a first bridge (B80410) extending between said first projection configuration and said second projection configuration; and (d) a second bridge (B80412) extending between said first projection configuration and said second projection configuration.

Example 62

The surgical staple cartridge of Example 61, wherein said first projection configuration comprises a first projection (B82310a, B82310b, B84310a) surrounding at least a portion of said first staple cavity, wherein said first projection extends from said deck to a first height, wherein said second projection configuration comprises a second projection (B82310c, B82310d, B84310b) surrounding at least a portion of said second staple cavity, wherein said second projection extends from said deck to a second height, wherein said first height is greater than said second height, wherein said third projection configuration comprises a third projection (B82310e, B82310f, B84210c) surrounding at least a portion of said third staple cavity, wherein said third projection extends from said deck to a third height, wherein said second height is greater than said third height.

Example 63

The surgical staple cartridge of Examples 61 or 62, wherein said first projection configuration comprises a first width, wherein said second projection configuration comprises a second width, and wherein said first width is different than said second width.

Example 64

The surgical staple cartridge of Example 63, wherein said first width is greater than said second width.

Example 65

The surgical staple cartridge of any of Examples 61, 62, 63, or 64, wherein said first staple cavity, said second staple cavity, and said third staple cavity are arranged in a longitudinal row (B82210, B84210).

Example 66

The surgical staple cartridge of any of Examples 61, 62, 63, 64, or 65, wherein said first bridge extends from said deck to a first bridge height; wherein said second bridge extends from said deck to a second bridge height, and wherein said second bridge height is different than said first bridge height.

Example 67

The surgical staple cartridge of Example 66, wherein said first bridge comprises a first tissue-facing surface, wherein said first tissue-facing surface comprises a first width, wherein said second bridge comprises a second tissue-facing surface, wherein said second tissue-facing surface comprises a second width, and wherein said first width is different than said second width.

Example 68

The surgical staple cartridge of Examples 66 or 67, further comprising a third bridge (B80414) extending between said second projection configuration and said third projection configuration, wherein said third bridge comprises a third tissue-facing surface comprising a third width, wherein said third width is different than said second width, and wherein said third width is different than said first width.

Example 69

The surgical staple cartridge of any of Examples 61, 62, 63, 64, 65, 66, 67, or 68, wherein said first staple cavity comprises a first proximal end and a first distal end, wherein said first projection comprises: a proximal portion (B80310a) surrounding at least a portion of said first proximal end; a distal portion (B80310b) surrounding at least a portion of said first distal end; and an intermediate portion (B80312) connecting said proximal portion and said distal portion.

Example 70

The surgical staple cartridge of Example 69, wherein said proximal portion extends from said deck to a proximal height, wherein said distal portion extends from said deck to a distal height, wherein said intermediate portion extends from said deck to an intermediate height, and wherein said intermediate height is different than said proximal height.

Example 71

The surgical staple cartridge of Example 61, wherein said first staple cavity comprises a plurality of longitudinally aligned proximal staple cavities (B84210a, B84220a, B84230a) in a proximal portion (B84A) of the deck surface, wherein said second staple cavity comprises a plurality of middle staple cavities (B84210b, B84220b, B84230b) longitudinally aligned in a middle portion (B84B) of the deck surface that is distal to the proximal portion, wherein the plurality of middle staple cavities are longitudinally aligned with the plurality of proximal staple cavities, and wherein a third staple cavity (B82210c, B84210c) defined in said cartridge body, wherein said third staple cavity comprises a plurality of distal staple cavities (B84210c, B84220c, B84230c) longitudinally aligned in a distal portion (B84C) of the deck surface that is distal to the middle portion, wherein the plurality of distal staple cavities are longitudinally aligned with the plurality of middle staple cavities and the plurality of proximal staple cavities.

Example 72

The surgical staple cartridge of Example 71, wherein the cartridge body (B84100) comprises a proximal end (B84102), a distal end (B84104) and a longitudinal slot (B84110) extending between the proximal end of the cartridge body and the distal end of the cartridge body, wherein the plurality of longitudinally aligned proximal staple cavities, plurality of middle staple cavities, and plurality of distal staple cavities are longitudinally aligned on a first side of the longitudinal slot, and wherein said surgical staple cartridge further comprises: a second plurality of longitudinally aligned second proximal staple cavities (B84220a) in the proximal portion of the deck surface, wherein each second proximal staple cavity comprises a corresponding second proximal projection configuration (B84221a) protruding above the deck surface and surrounding at least a portion of the corresponding second proximal staple cavity; a second plurality of second middle staple cavities (B84220b) longitudinally aligned in the middle portion of the deck surface, wherein the second plurality of second middle staple cavities are longitudinally aligned with the second plurality of second proximal second staple cavities, wherein each second middle staple cavity comprises a corresponding second middle projection configuration (B84221b) protruding above the middle portion of the deck surface and surrounding at least a portion of the corresponding second middle staple cavity; and a second plurality of second distal staple cavities (B84220c) longitudinally aligned in the distal portion of the deck surface, wherein the second plurality of second distal staple cavities are longitudinally aligned with the second plurality of second middle staple cavities and the second plurality of second proximal staple cavities, wherein each second distal staple cavity comprises a second distal projection configuration (B84221c) protruding above the distal portion of the deck surface and surrounding at least a portion of the corresponding second distal staple cavity, wherein the second proximal projection configuration differs from the second middle projection configuration, and wherein the second distal projection configuration differs from the second proximal projection configuration and the second middle projection configuration.

Example 73

The surgical staple cartridge of Example 72, further comprising: a third plurality of longitudinally aligned third proximal staple cavities (B84230a) in the proximal portion of the deck surface, wherein each third proximal staple cavity comprises a corresponding second proximal projection configuration (B84231a) protruding above the deck surface and surrounding at least a portion of the corresponding third proximal staple cavity; a third plurality of third middle staple cavities (B84230b) longitudinally aligned in the middle portion of the deck surface, wherein the third plurality of third middle staple cavities are longitudinally aligned with the third plurality of third proximal second staple cavities, wherein each third middle staple cavity comprises a corresponding third middle projection configuration (B84231b) protruding above the middle portion of the deck surface and surrounding at least a portion of the corresponding third middle staple cavity; and a third plurality of third distal staple cavities (B84230c) longitudinally aligned in the distal portion of the deck surface, wherein the third plurality of third distal staple cavities are longitudinally aligned with the third plurality of third middle staple cavities and the third plurality of third proximal staple cavities, wherein each third distal staple cavity comprises a third distal projection configuration (B84231c) protruding above the distal portion of the deck surface and surrounding at least a portion of the corresponding third distal staple cavity, wherein the third proximal projection configuration differs from the third middle projection configuration, and wherein the third distal projection configuration differs from the third proximal projection configuration and the third middle projection configuration.

Example 74

The surgical staple cartridge of Example 73, wherein each said first proximal projection configuration differs from each said second proximal projection and each said third proximal projection configuration.

Example 75

The surgical staple cartridge of Example 74, wherein said plurality of said longitudinally aligned proximal staple cavities are adjacent to said longitudinal slot, wherein said second plurality of said second proximal staple cavities are adjacent to said plurality of longitudinally aligned proximal staple cavities, wherein said third plurality of said third proximal staple cavities are longitudinally aligned adjacent to said second plurality of said second proximal staple cavities, wherein each said first proximal projection configuration comprises a first proximal projection height, wherein each said second proximal projection configuration comprises a second proximal projection height that is less than said first proximal projection height, and wherein each said third proximal projection configuration comprises a third proximal projection height that is less than said second proximal projection height.

Example 76

An apparatus (B110) comprising: (a) a cartridge body (B114, B114a-c, B214, B514, B514a); (b) a deck (B124, B124a-c, B224, B524, B524a) defined by the cartridge body (B114, B114a-c, B214, B514, B514a), wherein the deck (B124, B124a-c, B224, B524, B524a) is configured to compress tissue (T) against an anvil (44) of a surgical stapler (10); (c) an elongate slot (B126, B226, B526, B626) formed in the deck (B124, B124a-c, B224, B524, B524a), wherein the elongate slot (B126, B226, B526) is configured to slidably receive a knife (50) progressively and longitudinally relative to the deck (B124, B124a-c, B224, B524, B524a) therethrough; (d) a plurality of pockets (B128) formed in the deck (B124, B124a-c, B224, B524, B524a), wherein the pockets (B128) are configured to house a plurality of staples (B116), wherein the pockets (B128) are arranged in a first row (B144), a second row (B146), and a third row (B148), wherein the first row (B144) is arranged closer to the elongate slot (B126, B226, B526, B626) relative to the second row (B146) and the third row (B148); (e) a plurality of engagement protrusions (B130a-i) extending from the deck (B124, B124a-c, B224, B524, B524a), wherein the engagement protrusions (B130a-i) are configured to grip tissue (T) or an adjunct material (B188), wherein the engagement protrusions (B130a-i) are arranged into correspondence with the first row (B144), the second row (B146) and the third row (B148) of the plurality of pockets (B128); and (f) a plurality of interconnections (B160) extending from the deck (B124, B124a-c, B224, B524, B524a) and linking together longitudinally adjacent engagement protrusions (B130a-i) associated with the first row (B144) of the plurality of pockets (B128), but not longitudinally adjacent engagement protrusions (B130a-i) associated with the second row (B146) and the third row (B148) of the plurality of pockets (B128).

Example 77

The apparatus (B110) of Example 76, the interconnections (B160) and adjacent engagement protrusions (B130a-i) associated with the first row (B144) defining a daisy chained configuration.

Example 78

The apparatus (B110) of Examples 76 or 77, the interconnections (B160) being positioned relative to the first row (B144) in an alternating manner with respect to the engagement protrusions (B130a-i) associated with the first row (B144).

Example 79

The apparatus (B110) of any of Examples 76 through 78, the engagement protrusions (B130a-f) and interconnections (B160) being integrally formed together as a unitary piece with the deck (B124, B124a-c, B224, B524, B524a).

Example 80

The apparatus (B110) of any of Examples 76 through 79, the engagement protrusions (B130a-i) associated with the first row (B144) being joined by interconnections (B160) along an entire length (BL) of the first row (B144) of the plurality of pockets (B128).

Example 81

The apparatus (B110) of any of Examples 76 through 80, the engagement protrusions (B130a-i) associated with the second row (B146) and the third row (B148) of the plurality of pockets (B128) are not joined by any interconnection, thereby forming an open space defined by the deck (B124, B124a-c, B224, B524, B524a) between adjacent engagement protrusions (B130a-i).

Example 82

The apparatus (B110) of any of Examples 76 through 81, one or more engagement protrusions (B140d) associated with the first row (B144) of the plurality of pockets (B128) and adjacent interconnections (B160) defining one or more planar surfaces (B184a-e) oriented substantially parallel to the deck (B124, B124a-c, B224, B524, B524a).

Example 83

The apparatus (B110) of any of Examples 76 through 82, each engagement protrusion (B130a-i) defining a maximum width (BWep) in a direction transverse to a longitudinal axis (BLA) defined by the cartridge body (B114, B114a-c, B214, B514, B514a), each interconnection (B160) defining a maximum width (Bwi) in the direction transverse to the longitudinal axis (BLA), the maximum width (BWep) defined by each engagement protrusion (B130a-i) being greater than the maximum width (Bwi) defined by each interconnection (B160).

The following clauses also relate to various non-exhaustive ways in which the teachings herein may be combined or applied.

1. An apparatus comprising:
   (a) a cartridge body;
   (b) a deck defined by the cartridge body, wherein the deck is configured to compress tissue against an anvil of a surgical stapler;
   (c) an elongate slot, wherein the elongate slot is configured to slidably receive a knife progressively and longitudinally relative to the deck therein;
   (d) a plurality of pockets formed in the deck, the plurality of pockets configured to house a plurality of staples, wherein the plurality of pockets includes first and second pockets, each of the first and second pockets comprising:
      (i) a first longitudinal end,
      (ii) a second longitudinal end disposed opposite the first longitudinal end,
      (iii) a first lateral side disposed between the first and second longitudinal ends, and
      (iv) a second lateral side disposed between the first and second longitudinal ends and opposite to the first lateral side; and
   (e) a plurality of engagement protrusions extending from the deck and configured to grip tissue or an adjunct material, the plurality of engagement protrusions comprising:
      (i) a first engagement protrusion associated with the first pocket, wherein the first engagement protrusion includes a lateral portion extending longitudinally along the first lateral side of the first pocket parallel to a longitudinal axis of the cartridge body, wherein the lateral portion is recessed relative to at least a portion of the first engagement protrusion, wherein the first engagement protrusion does not extend along the second lateral side of the first pocket such that the second lateral side opens directly to the deck, and
      (ii) a second engagement protrusion associated with the second pocket.

2. The apparatus of Clause 1, wherein the second engagement protrusion includes a lateral portion extending longitudinally along the second lateral side of the second pocket.

3. The apparatus of Clause 2, wherein the second engagement protrusion does not extend along the first lateral side of the second pocket such that the first lateral side opens directly to the deck.

4. The apparatus of Clause 1, wherein the first and second lateral sides of the first pocket extend substantially parallel to the elongate slot.

5. The apparatus of Clause 1, wherein the plurality of engagement protrusions are arranged into at least first and second rows, wherein the first row is positioned closer to the elongate slot than the second row, wherein the first row defines a length, wherein the lateral portion alternates between longitudinally adjacent pockets along the length of the first row.

6. The apparatus of Clause 5, wherein longitudinally adjacent engagement protrusions of the second row are not linked together using an interconnection extending from the deck, wherein the first row is substantially parallel to the elongate slot.

7. The apparatus of Clause 2,
   (i) the first engagement protrusion comprising:
      (A) a first end portion that wraps around the first longitudinal end of the first pocket,
      (B) a second end portion that wraps around the second longitudinal end of the first pocket, and
      (C) the lateral portion extending between the first and second end portions of the first engagement protrusion, and
   (ii) the second engagement protrusion comprising:
      (A) a first end portion that wraps around the first longitudinal end of the second pocket,
      (B) a second end portion that wraps around the second longitudinal end of the second pocket, and
      (C) the lateral portion extending between the first and second end portions of the second engagement protrusion.

8. The apparatus of Clause 7, further comprising an interconnection extending between the second end portion of first engagement protrusion and the first end portion of the second engagement protrusion.

9. The apparatus of Clause 8, wherein the first and second end portions of the first engagement protrusion extend from the deck a first maximum height, wherein the interconnection extends from the deck a second maximum height, wherein the first maximum height is greater than the second maximum height.

10. The apparatus of Clause 7, wherein the first and second end portions of the first engagement protrusion extend from the deck a first maximum height, wherein the lateral portion of the first engagement protrusion extends from the deck a second maximum height, wherein the first maximum height is greater than the second maximum height.

11. The apparatus of Clause 10, wherein the first maximum height is about double the second maximum height.

12. The apparatus of Clause 1, wherein the plurality of pockets are arranged into at least first and second rows, wherein the first row is positioned closer to the elongate slot than the second row, wherein the first and second pockets arranged in the first row.

13. The apparatus of Clause 5, wherein the plurality of engagement protrusions include a first row of engagement protrusions associated with the first row of the pockets.

14. The apparatus of Clause 1, wherein each engagement protrusion of the first row of engagement protrusions at least partially surrounds a respective pocket of the first row of pockets.

15. The apparatus of Clause 1, wherein the deck is substantially planar.

16. An apparatus comprising:
  (a) a cartridge body;
  (b) a deck defined by the cartridge body, wherein the deck is configured to compress tissue against an anvil of a surgical stapler;
  (c) an elongate slot formed in the deck, wherein the elongate slot is configured to slidably receive a knife progressively and longitudinally relative to the deck therethrough;
  (d) a plurality of pockets formed in the deck, wherein the pockets are configured to house a plurality of staples, wherein the pockets include first and second pockets arranged in a first row, wherein the first row defines a length;
  (e) a plurality of engagement protrusions extending from the deck, wherein the engagement protrusions are configured to grip tissue or an adjunct material, wherein the engagement protrusions are arranged into at least a first row, wherein each engagement protrusion of the first row of engagement protrusions is associated with a respective pocket of the first row of pockets; and
  (f) a plurality of interconnections extending from the deck and linking together longitudinally adjacent engagement protrusions of the first row of engagement protrusions, wherein the engagement protrusions of the first row and the interconnections collectively form a continuous non-linear raised cross-sectional area extending from the deck along the length of the first row of pockets.

17. The apparatus of Clause 16, wherein the continuous non-linear raised cross-sectional area has a non-uniform width.

18. The apparatus of Clause 16, wherein the continuous non-linear raised cross-sectional area is configured to provide increased stiffness to the first row of engagement protrusions.

19. The apparatus of Clause 16, wherein the first row of engagement protrusions extend from the deck a first maximum height, wherein the interconnection extends from the deck a second maximum height, wherein the first maximum height is greater than the second maximum height.

20. A surgical staple cartridge, comprising:
  (a) a cartridge body comprising a deck;
  (b) a plurality of staple cavities in said cartridge body, wherein said plurality of staple cavities comprises:
    (i) a first staple cavity defined in said cartridge body, wherein each first staple cavity comprises a first projection configuration;
    (ii) a second staple cavity defined in said cartridge body, wherein said second staple cavity is distal to said first staple cavity and comprises a second projection configuration; and
    (iii) a third staple cavity defined in said cartridge body, wherein said third staple cavity is distal to said second staple cavity and comprises a third projection configuration, wherein said second projection configuration differs from said first projection configuration, and wherein said third projection configuration differs from said second projection configuration and said first projection configuration;
  (c) a first bridge (B80410) extending between said first projection configuration and said second projection configuration; and
  (d) a second bridge (B80412) extending between said first projection configuration and said second projection configuration.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,175, filed Feb. 27, 2024, entitled "Surgical Stapler Cartridge Having Tissue Engagement Protrusions with Enlarged Engagement Surface," published as U.S. Pat. Pub. No. 2024/0382198 on Nov. 21, 2024; U.S. patent application Ser. No. 18/588,206, filed Feb. 27, 2024, entitled "Surgical Stapler Cartridge Having Raised Surface to Promote Buttress Adhesion," published as U.S. Pat. Pub. No. 2024/0382202 on Nov. 21, 2024; U.S. patent application Ser. No. 18/588,240, filed Feb. 27, 2024, entitled "Surgical Stapler Cartridge Having Cartridge Retention Features," issued as U.S. Pat. No. 12,285,170 on Apr. 29, 2025; U.S. patent application Ser. No. 18/588,269, filed Feb. 27, 2024, entitled "Surgical Stapler Anvil Having Staple Forming Pockets with Laterally Varying Orientations," published as U.S. Pat. Pub. No. 2024/0341761 on Oct. 17, 2024; U.S. patent application Ser. No. 18/588,684, filed Feb. 27, 2024, entitled "Method of Surgical Stapling," published as U.S. Pat. Pub. No. 2024/0350137 on Oct. 24, 2024; and/or U.S. patent application Ser. No. 18/588,094, filed Feb. 27, 2024, entitled "Incompatible Staple Cartridge Use Prevention Features for Surgical Stapler," published as U.S. Pat. Pub. No. 2024/0382201 on Nov. 21, 2024. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
  (a) a cartridge body;
  (b) a deck defined by the cartridge body, wherein the deck is configured to compress tissue against an anvil of a surgical stapler;
  (c) an elongate slot, wherein the elongate slot is configured to slidably receive a knife progressively and longitudinally relative to the deck therein;
  (d) a plurality of pockets formed in the deck, the plurality of pockets configured to house a plurality of staples, wherein the plurality of pockets includes first and second pockets, each of the first and second pockets comprising:
    (i) a first longitudinal end,
    (ii) a second longitudinal end disposed opposite the first longitudinal end,
    (iii) a first lateral side disposed between the first and second longitudinal ends, and
    (iv) a second lateral side disposed between the first and second longitudinal ends and opposite to the first lateral side; and
  (e) a plurality of engagement protrusions extending from the deck and configured to grip tissue or an adjunct material, the plurality of engagement protrusions comprising:
    (i) a first engagement protrusion associated with the first pocket, wherein the first engagement protrusion includes a lateral portion extending longitudinally along the first lateral side of the first pocket parallel to a longitudinal axis of the cartridge body, wherein the lateral portion is recessed relative to at least a portion of the first engagement protrusion, wherein the first engagement protrusion does not extend along the second lateral side of the first pocket such that the second lateral side opens directly to the deck, and
    (ii) a second engagement protrusion associated with the second pocket.

2. The apparatus of claim 1, wherein the second engagement protrusion includes a lateral portion extending longitudinally along the second lateral side of the second pocket.

3. The apparatus of claim 2,
  (i) the first engagement protrusion comprising:
    (A) a first end portion that wraps around the first longitudinal end of the first pocket,
    (B) a second end portion that wraps around the second longitudinal end of the first pocket, and
    (C) the lateral portion extending between the first and second end portions of the first engagement protrusion, and
  (ii) the second engagement protrusion comprising:
    (A) a first end portion that wraps around the first longitudinal end of the second pocket,
    (B) a second end portion that wraps around the second longitudinal end of the second pocket, and
    (C) the lateral portion extending between the first and second end portions of the second engagement protrusion.

4. The apparatus of claim 3, further comprising an interconnection extending between the second end portion of first engagement protrusion and the first end portion of the second engagement protrusion.

5. The apparatus of claim 4, wherein the first and second end portions of the first engagement protrusion extend from the deck a first maximum height, wherein the interconnection extends from the deck a second maximum height, wherein the first maximum height is greater than the second maximum height.

6. The apparatus of claim 3, wherein the first and second end portions of the first engagement protrusion extend from the deck a first maximum height, wherein the lateral portion of the first engagement protrusion extends from the deck a second maximum height, wherein the first maximum height is greater than the second maximum height.

7. The apparatus of claim 6, wherein the first maximum height is about double the second maximum height.

8. The apparatus of claim 1, wherein the second engagement protrusion does not extend along the first lateral side of the second pocket such that the first lateral side opens directly to the deck.

9. The apparatus of claim 1, wherein the first and second lateral sides of the first pocket extend substantially parallel to the elongate slot.

10. The apparatus of claim 1, wherein the plurality of engagement protrusions are arranged into at least first and second rows, wherein the first row is positioned closer to the elongate slot than the second row, wherein the first row defines a length, wherein the lateral portion alternates between longitudinally adjacent pockets along the length of the first row.

11. The apparatus of claim 10, wherein longitudinally adjacent engagement protrusions of the second row are not linked together using an interconnection extending from the deck, wherein the first row is substantially parallel to the elongate slot.

12. The apparatus of claim 10, wherein the plurality of engagement protrusions include a first row of engagement protrusions associated with the first row of the pockets.

13. The apparatus of claim 1, wherein the plurality of pockets are arranged into at least first and second rows, wherein the first row is positioned closer to the elongate slot than the second row, wherein the first and second pockets arranged in the first row.

14. The apparatus of claim 1, wherein each engagement protrusion of the first row of engagement protrusions at least partially surrounds a respective pocket of the first row of pockets.

15. The apparatus of claim 1, wherein the deck is substantially planar.

16. An apparatus comprising:
(a) a cartridge body;
(b) a deck defined by the cartridge body, wherein the deck is configured to compress tissue against an anvil of a surgical stapler;
(c) an elongate slot formed in the deck, wherein the elongate slot is configured to slidably receive a knife progressively and longitudinally relative to the deck therethrough;
(d) a plurality of pockets formed in the deck, wherein the pockets are configured to house a plurality of staples, wherein the pockets include first and second pockets arranged in a first row, wherein the first row defines a length;
(e) a plurality of engagement protrusions extending from the deck, wherein the engagement protrusions are configured to grip tissue or an adjunct material, wherein the engagement protrusions are arranged into at least a first row, wherein each engagement protrusion of the first row of engagement protrusions is associated with a respective pocket of the first row of pockets; and
(f) a plurality of interconnections extending from the deck and linking together longitudinally adjacent engagement protrusions of the first row of engagement protrusions, wherein the engagement protrusions of the first row and the interconnections collectively form a continuous non-linear raised cross-sectional area extending from the deck along the length of the first row of pockets.

17. The apparatus of claim 16, wherein the continuous non-linear raised cross-sectional area has a non-uniform width.

18. The apparatus of claim 16, wherein the continuous non-linear raised cross-sectional area is configured to provide increased stiffness to the first row of engagement protrusions.

19. The apparatus of claim 16, wherein the first row of engagement protrusions extend from the deck a first maximum height, wherein the interconnection extends from the deck a second maximum height, wherein the first maximum height is greater than the second maximum height.

20. A surgical staple cartridge, comprising:
(a) a cartridge body comprising a deck;
(b) a plurality of staple cavities in said cartridge body, wherein said plurality of staple cavities comprises:
(i) a first staple cavity defined in said cartridge body, wherein each first staple cavity comprises a first projection configuration;
(ii) a second staple cavity defined in said cartridge body, wherein said second staple cavity is distal to said first staple cavity and comprises a second projection configuration; and
(iii) a third staple cavity defined in said cartridge body, wherein said third staple cavity is distal to said second staple cavity and comprises a third projection configuration, wherein said second projection configuration differs from said first projection configuration, and wherein said third projection configuration differs from said second projection configuration and said first projection configuration;
(c) a first bridge extending between said first projection configuration and said second projection configuration; and
(d) a second bridge extending between said first projection configuration and said second projection configuration.

* * * * *